United States Patent
Herdewijn et al.

(10) Patent No.: US 9,518,066 B2
(45) Date of Patent: Dec. 13, 2016

(54) GAK MODULATORS

(71) Applicant: KATHOLIEKE UNIVERSITEIT LEUVEN, Leuven (BE)

(72) Inventors: Piet Herdewijn, Heverlee (BE); Steven De Jonghe, Tervuren (BE); Sona Kovachova, Leuven (BE); Lei Chang, Heverlee (BE); Michal Sala, Kladno (CZ)

(73) Assignee: Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 14/897,259

(22) PCT Filed: Jul. 4, 2014

(86) PCT No.: PCT/EP2014/064298
§ 371 (c)(1),
(2) Date: Dec. 10, 2015

(87) PCT Pub. No.: WO2015/001076
PCT Pub. Date: Jan. 8, 2015

(65) Prior Publication Data
US 2016/0122364 A1    May 5, 2016

(30) Foreign Application Priority Data
Jul. 5, 2013 (GB) .................. 1312059.7

(51) Int. Cl.
*A61K 31/4365* (2006.01)
*C07D 513/04* (2006.01)
*C07D 519/00* (2006.01)

(52) U.S. Cl.
CPC ........... *C07D 513/04* (2013.01); *C07D 519/00* (2013.01)

(58) Field of Classification Search
CPC .. C07D 513/04; C07D 519/00; A61K 31/4365
USPC ............................................. 514/228.5, 301
See application file for complete search history.

(56) References Cited

U.S. PATENT DOCUMENTS

2006/0105445 A1    5/2006    Godl et al.

FOREIGN PATENT DOCUMENTS

WO    2004013633 A2    2/2004
WO    2007015866 A2    2/2007

OTHER PUBLICATIONS

Gewald K et al., entitled "Synthese und Reaktionen von 4-Aminoisothiazolen," Liebigs Annalen Der Chemie, vol. 1979, No. 10, Oct. 26, 1979, pp. 1534-1546.*
PCT International Search Report dated Sep. 24, 2014 for PCT International Patent Application No. PCT/EP2014/064298, 4 pages.
PCT Written Opinion of the International Searching Authority dated Sep. 24, 2014 for PCT International Patent Application No. PCT/EP2014/064298, 6 pages.
Taurins A et al, entitled "Isothiazolopyridines. II Synthesis and Spectra of Isothiazolo [3,4-b]-, 3-Amino-isothiazolo [4,3-b]-, Isothiazolo [5,4-b]-and 3-Methylisothiazolo [5,4-c]pyridines. Preparation and Spectra of Some 2,3- and 3,4-Disubstituted Pyridines, Canadian Journal of Chemistry," vol. 51, No. 11, Nov. 1, 1973, pp. 1741-1748.
Kudek S D et al., entitled "Heterocyclic fused pyridine carboxylic acid M1 positive allosteric modulators," Bioorganic and Medicinal Chemistry Letters, vol. 20, Mar. 3, 2010, pp. 2533-2537.
PCT Notification Concerning Transmittal of International Preliminary Report on Patentability and Written Opinion of the International Searching Authority, date of issuance Jan. 5, 2016 in connection with PCT International Patent Application No. PCT/EP2014/064298, 8 pages.

* cited by examiner

*Primary Examiner* — Kamal Saeed
*Assistant Examiner* — Janet L Coppins
(74) *Attorney, Agent, or Firm* — Amster, Rothstein & Ebenstein LLP

(57) ABSTRACT

The present invention relates to a class of novel isothiazolo [4,3-b]pyridine derivatives and a method for their preparation, as well as to pharmaceutical compositions comprising one or more of said isothiazolo[4,3-b]pyridine derivatives and one or more pharmaceutically acceptable excipients. The present invention further relates to the use of said novel isothiazolo[4,3-b]pyridine derivatives as biologically active ingredients, more specifically as medicaments for the treatment of disorders and pathologic conditions such as, but not limited to, cell-proliferative and neurodegenerative diseases.

12 Claims, No Drawings

GAK MODULATORS

CROSS-REFERENCE TO RELATED APPLICATIONS

This application is a U.S. national stage entry under 35 U.S.C. §371 of PCT International Patent Application No. PCT/EP2014/064298, filed Jul. 4, 2014, which claims priority to Great Britain Patent Application No. 1312059.7, filed Jul. 5, 2013, the contents of which are incorporated herein by reference in their entirety.

FIELD OF THE INVENTION

The present invention relates to a class of novel isothiazolo[4,3-b]pyridine derivatives and a method for their preparation, as well as to pharmaceutical compositions comprising one or more of said isothiazolo[4,3-b]pyridine derivatives and one or more pharmaceutically acceptable excipients. The present invention further relates to the use of said novel isothiazolo[4,3-b]pyridine derivatives as biologically active ingredients, more specifically as medicaments for the treatment of disorders and pathologic conditions such as, but not limited to, cell-proliferative and neurodegenerative diseases.

BACKGROUND OF THE INVENTION

The ubiquitously expressed kinase GAK (cyclin G-associated kinase, also known as auxilin 2) is a 160 kDa serine/threonine protein kinase that was first identified as a cyclin G1-binding protein. GAK is composed of a N-terminal kinase domain that phosphorylates the µ-subunits of adaptor proteins 1 and 2, a clathrin binding domain, and a C-terminal J-domain that interacts with a heat shock cognate 70 (Hsc70).

As suggested by its strong homology (43%) to the neuronal-specific protein auxilin, a heat shock cognate 70 (Hsc70) cochaperone with a role in uncoating clathrin vesicles, GAK regulates clathrin-mediated membrane trafficking as an essential cofactor for the Hsc70-dependent uncoating of clathrin-coated vesicles. Moreover, down-regulation of GAK by a small hairpin RNA enhanced the levels of expression and tyrosine kinase activity of EGFR and altered the spectrum of downstream signaling, at least partly due to alterations in receptor trafficking.

GAK forms a complex with Cyclin G and the protein phosphatase 2A (PP2A) B'γ subunit, which suggests that it may play yet unidentified roles in cellular events other than membrane trafficking. In support of this hypothesis, GAK acts as a transcriptional coactivator of the androgen receptor (AR; a ligand-dependent transcription factor), and GAK expression was significantly increased in hormone refractory prostate cancer. Moreover, both GAK and its association partner clathrin heavy chain (CHC), localize to both the cytoplasm and nucleus with distinct association modes, and CHC colocalizes with GAK in the nucleus, while Cyclin G and PP2A B'γ are also present in the nucleus. Moreover, siRNA-mediated GAK knockdown caused cell-cycle arrest at metaphase, which revealed two novel functions of GAK: maintenance of proper centrosome stability and of mitotic chromosome congression.

High-throughput screening of the kinome is a powerful tool with which one can identify multiple kinases related to the survival of cancer cells. Kinase shRNA screening revealed that the loss of function of GAK, among others, resulted in marked growth inhibition of osteosarcoma cells (*Mol. Cancer Ther.* 2010, 9 (12), 3342-3350).

In contrast to the high expression of GAK in osteosarcomas, normal human osteoblasts expressed only low quantity of the protein. The result of kinase shRNA screening was further confirmed by siRNA knockdown of GAK on several osteosarcoma cell lines. Although 100 nmol/L of nonspecific siRNA did not have any cytotoxic activity on osteosarcoma cell lines, a concentration of as low as 10 nmol/L of GAK siRNA was enough to inhibit the proliferation of osteosarcoma cells. Importantly, it had similar effects on both drug-sensitive and drug-resistant osteosarcoma cell lines, which implicate that it exerts its effects independently of ATP-binding cassette transporters such as P-gp. This was further confirmed by Western blot analysis of P-gp, which did not show any effect on Pgp trafficking. Therefore, GAK has the potential to be a target for the treatment of drug-naive osteosarcomas as well as multidrug-resistant osteosarcomas.

In addition, recent genome wide association studies (GWAS) have been performed to identify genetic risk factors in sporadic, non-familial forms of disease. The GWAS showed an association for a few genes previously identified in the linkage studies (alpha-synuclein, LRRK2) and also identified new genetic risk factors for Parkinson's disease, such as glucocerebrosidase (GBA), microtubule associated protein tau (MAPT), PARK16, the human leukocyte antigen (HLA) locus, bone marrow stromal antigen 1 (BST1) and GAK (*The Application of Clinical Genetics* 2011, 4, 67-80). GAK has been labeled as the PARK17 gene. Later studies confirmed an association between Parkinson's disease and GAK (*Hum. Genet.* 2009, 124, 593-605; *Nature Genet.* 2010, 42, 781-785; *Hum. Mol. Genet.* 2011, 20, 345-353; *Neurology* 2012, 79, 659-667; *Ann. Hum. Genet.* 2011, 75, 195-200). A systematic meta-analysis in Parkinson's disease genetics confirms overall probability values showing robust association of genetic markers in the GAK gene with Parkinson's disease (*PLoS Genet.* 2012, 8, e1002548). Therefore, multiple genetic studies confirm a role for GAK in Parkinson's disease.

Hypoxia induces changes to cancer cells that facilitate their survival, make them more resistant to classical drug treatments and increases the metastatic potential of tumor cells. Researchers from Wyeth have therefore carried out a kinome wide siRNA screening in order to identify kinase genes that affect hypoxic colon cancer cells (*J Biomol Screen.* 2013 18, 782-796.). Hits identified in the screen were characterized for effects on different molecular responses to hypoxia. The hits were validated by short hairpin RNA studies. These studies led to the observation that GAK plays in important role in the adaptation of cancer cells to hypoxia. Therefore, GAK can be considered as a promising drug target for the treatment of cancer cells within the hypoxic regions of a solid tumor.

The synthesis of a very limited number of isothiazolo[4,3-b]pyridine has been described in literature. The synthesis of 3-aminoisothiazolo[4,3-b]pyridine from 3-aminopicolinonitrile via 3-aminothiopicolinamide, followed by a subsequent oxidative cyclization with $H_2O_2$ to give 3-aminoisothiazolo[4,3-b]pyridine has been described in *Can. J. Chem.* 1973, 51(11), 1741-1748. Isothiazolo[4,3-b]pyridines have also been synthesized also as M1 positive allosteric modulators (*Bioorg. Med. Chem. Lett.* 2010, 20, 2533-2537).

However none of these documents teaches or suggests isothiazolo[4,3-b]pyridine derivatives having the substitution pattern disclosed by the present invention.

However there is a continuous need in the art for specific and highly therapeutically active compounds, that act as GAK inhibitors and possess anti-tumor cell proliferation activity, and as such, are useful for treating hyperproliferative disorders.

SUMMARY OF THE INVENTION

The present invention is based on the unexpected finding that certain combinations of substituents at positions 3 and 6 of the isothiazolo[4,3-b]pyridine ring system, said combinations not being suggested by the prior art, show unexpected biological properties, in particular have significant GAK inhibitory activity.

Numbered statements of this invention are:
1. An isothiazolo[4,3-b]pyridine derivative having the general formula I:

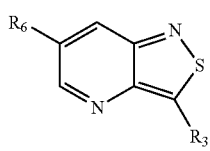

wherein
  $R_3$ is selected from the group consisting of halogen, amino, morpholinyl, thiomorpholinyl, pyrrolidinyl, piperazinyl, homopiperazinyl, piperidinyl, (mono- or di-) $C_{1-12}$ alkylamino, (mono- or di-) $C_{2-12}$ alkenylamino, (mono- or di-) $C_{2-12}$ alkynylamino, monoarylamino; diarylamino; (mono- or di-) $C_{3-10}$ cycloalkylamino, $C_{3-10}$ cycloalkyl$C_{1-4}$ alkylamino, (mono- or di-) $C_{3-10}$ cycloalkenylamino, (mono- or di-) hydroxy $C_{1-7}$ alkylamino, (mono- or di-) $C_{1-4}$ alkylarylamino, (mono- or di-) aryl$C_{1-4}$ alkylamino, mercapto $C_{1-7}$ alkyl, $C_{1-7}$ alkoxy, $C_{1-4}$ alkoxy$C_{1-4}$ alkylamino, alkoxyaryl, $C_{3-10}$ cycloalkoxy, heterocyclic-substituted alkylamino, heterocyclic-substituted arylamino, heterocyclic amino, hydroxy-alkylamino, mercaptoalkylamino, hydroxypiperidinyl, aryl and heteroaryl groups, and, wherein said morpholinyl, thiomorpholinyl, pyrrolidinyl, piperazinyl, piperidinyl, heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, and, wherein one or more carbon atoms in any ring group may be replaced with —C(=O)—;
  $R_6$ is selected from the group consisting of halogen, heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino;

and/or a pharmaceutical acceptable addition salt thereof and/or a stereoisomer thereof and/or a solvate thereof.

2. An isothiazolo[4,3-b]pyridine derivative according to statement 1, wherein $R^6$ is selected from the group consisting of 3,4-dimethoxyphenyl; 3-thienyl; phenyl; 2-thienyl; 4-methoxycarbonyl-3-methoxy-phenyl; 4-acetoxy-3-methoxyphenyl; 3-acetoxy-4-methoxyphenyl; 3-methoxyphenyl; 4-methoxyphenyl; 3-furanyl; N-methylbenzamide; 3-methoxy-4-hydroxyphenyl; 3,5-dimethoxyphenyl; 3,4,5-trimethoxyphenyl, 2,5-dimethoxyphenyl, 2-bromo-4,5-dimethoxyphenyl and 4-amino-3-methoxyphenyl.

3. An isothiazolo[4,3-b]pyridine derivative according to statement 1 or 2, wherein $R^6$ is selected from the group consisting of 3,4-dimethoxyphenyl; 3-thienyl; phenyl; 2-thienyl; 4-methoxycarbonyl-3-methoxy-phenyl; 4-acetoxy-3-methoxyphenyl; 3,5-dimethoxyphenyl; 3,4,5-trimethoxyphenyl, 2,5-dimethoxyphenyl, 2-bromo-4,5-dimethoxyphenyl and 4-amino-3-methoxyphenyl.

4. An isothiazolo[4,3-b]pyridine derivative according to any one of statements 1, 2 or 3, wherein $R^3$ is selected from the group consisting of morpholinyl, ethanolamino, thiomorpholinyl, piperidinyl, 4-piperidinone, 4-hydroxypiperidinyl, 3-hydroxypiperidinyl, n-pentanolamino, tetrahydropyranyl-4-amino, diethanolamino, 2,3-dihydroxypropanylamino, pyrrolidinyl, methoxyethylamino, cyclopropylmethylamino, dimethylamino, diethylamino, 2,6-dimethylmorpholinyl, phenyl, pyridinyl, thienyl and ethoxy.

5. An isothiazolo[4,3-b]pyridine derivative selected from the group consisting of:
3-morpholino-6-phenyl-isothiazolo[4,3-b]pyridine;
3-morpholino-6-(4-fluoro-phenyl)isothiazolo[4,3-b]pyridine;
3-morpholino-6-(3-pyridyl))-isothiazolo[4,3-b]pyridine;
3-morpholino-6-(3,4-dimethoxyphenyl)-isothiazolo[4,3-b]pyridine;
3-morpholino-6-(3-thienyl)-isothiazolo[4,3-b]pyridine;
3-ethanolamino-6-(3-pyridyl)-isothiazolo[4,3-b]pyridine;
3-ethanolamino-6-(3,4-dimethoxyphenyl)-isothiazolo[4,3-b]pyridine;
3-ethanolamino-6-(3-thienyl)-isothiazolo[4,3-b]pyridine;
3-ethanolamino-6-(3-phenyl)-isothiazolo[4,3-b]pyridine;
3-methoxy-6-phenyl-isothiazolo[4,3-b]pyridine;
3-methoxy-6-(4-fluoro-phenyl)isothiazolo[4,3-b]pyridine;
3-methoxy-6-(3-pyridyl)-isothiazolo[4,3-b]pyridine;
3-methoxy-6-(3,4-dimethoxyphenyl)-isothiazolo[4,3-b]pyridine;
3-methoxy-6-(3-thienyl)isothiazolo[4,3-b]pyridine;
3-(N-Me-piperazinyl)-6-phenyl-isothiazolo[4,3-b]pyridine;
3-(N-Me-piperazinyl)-6-(3-pyridyl)-isothiazolo[4,3-b]pyridine;
3-(N-Me-piperazinyl)-6-(3,4-dimethoxyphenyl)-isothiazolo[4,3-b]pyridine;
3-(N-Me-piperazinyl)-6-(3-thienyl)isothiazolo[4,3-b]pyridine;
3-(N-Me-piperazinyl)-6-(4-fluorophenyl)-isothiazolo[4,3-b]pyridine;
3-amino-6-phenyl-isothiazolo[4,3-b]pyridine;
3-amino-6-(3-pyridyl)-isothiazolo[4,3-b]pyridine;
3-amino-6-(3,4-dimethoxyphenyl)-isothiazolo[4,3-b]pyridine;
3-amino-6-(4-fluorophenyl)-isothiazolo[4,3-b]pyridine;
3-amino-6-(3-thienyl)-isothiazolo[4,3-b]pyridine;
4-(6-(Thiophen-2-yl)isothiazolo[4,3-b]pyridin-3-yl)morpholine;

4-(6-(2,5-Dimethoxyphenyl)isothiazolo[4,3-b]pyridin-3-yl)morpholine;
4-(6-(2,4-Dimethoxyphenyl)isothiazolo[4,3-b]pyridin-3-yl)morpholine;
Methyl 2-methoxy-4-(3-morpholinoisothiazolo[4,3-b]pyridin-6-yl)benzoate;
2-Methoxy-4-(3-morpholinoisothiazolo[4,3-b]pyridin-6-yl)phenyl acetate;
4-(6-(3,5-Dimethoxyphenyl)isothiazolo[4,3-b]pyridin-3-yl)morpholine;
4-(6-(3,4,5-Trimethoxyphenyl)isothiazolo[4,3-b]pyridin-3-yl)morpholine;
2-Methoxy-4-(3-morpholinoisothiazolo[4,3-b]pyridin-6-yl)aniline;
4-(6-(Benzo[d][1,3]dioxol-5-yl)isothiazolo[4,3-b]pyridin-3-yl)morpholine;
4-(6-(Furan-3-yl)isothiazolo[4,3-b]pyridin-3-yl)morpholine;
Methyl 4-(3-morpholinoisothiazolo[4,3-b]pyridin-6-yl)benzoate;
N-Methyl-4-(3-morpholinoisothiazolo[4,3-b]pyridin-6-yl)benzamide;
6-bromo-3-(piperidin-1-yl)isothiazolo[4,3-b]pyridine;
6-bromo-3-thiomorpholinoisothiazolo[4,3-b]pyridine;
3-morpholino-6-aryl-isothiazolo[4,3-b]pyridines;
6-(3,4-dimethoxyphenyl)-3-(piperidin-1-yl)isothiazolo[4,3-b]pyridine;
6-(3,4-dimethoxyphenyl)-3-thiomorpholinoisothiazolo[4,3-b]pyridine;
3-bromo-6-(2-bromo-4,5-dimethoxyphenyl)isothiazolo[4,3-b]pyridine;
4-(6-(2-bromo-4,5-dimethoxyphenyl)isothiazolo[4,3-b]pyridin-3-yl)morpholine;
4-(6-(3-methoxyphenyl)isothiazolo[4,3-b]pyridin-3-yl)morpholine;
2-methoxy-5-(3-morpholinoisothiazolo[4,3-b]pyridin-6-yl)phenyl acetate;
4-(6-(4-methoxyphenyl)isothiazolo[4,3-b]pyridin-3-yl)morpholine;
1-(6-(3,4-dimethoxyphenyl)isothiazolo[4,3-b]pyridin-3-yl)piperidin-4-one;
1-(6-(3,4-dimethoxyphenyl)isothiazolo[4,3-b]pyridin-3-yl)piperidin-4-ol;
5-(6-(3,4-dimethoxyphenyl)isothiazolo[4,3-b]pyridin-3-ylamino)pentan-1-ol;
1-(6-(3,4-dimethoxyphenyl)isothiazolo[4,3-b]pyridin-3-yl)piperidin-3-ol;
6-(3,4-dimethoxyphenyl)-N-(tetrahydro-2H-pyran-4-yl)isothiazolo[4,3-b]pyridin-3-amine;
2,2'-(6-(3,4-dimethoxyphenyl)isothiazolo[4,3-b]pyridin-3-ylazanediyl)diethanol;
3-(6-(3,4-dimethoxyphenyl)isothiazolo[4,3-b]pyridin-3-ylamino)propane-1,2-diol;
ethyl-4-(6-(3,4-dimethoxyphenyl)isothiazolo[4,3-b]pyridin-3-ylamino)piperidine-1-carboxylate;
6-(3,4-dimethoxyphenyl)-3-(pyrrolidin-1-yl)isothiazolo[4,3-b]pyridine;
6-(3,4-dimethoxyphenyl)-N-phenethylisothiazolo[4,3-b]pyridin-3-amine;
6-(3,4-dimethoxyphenyl)-N-(2-methoxyethyl)isothiazolo[4,3-b]pyridin-3-amine;
N-(cyclopropylmethyl)-6-(3,4-dimethoxyphenyl)isothiazolo[4,3-b]pyridin-3-amine;
6-(3,4-dimethoxyphenyl)-N,N-dimethylisothiazolo[4,3-b]pyridin-3-amine;
6-(3,4-dimethoxyphenyl)-N,N-diethylisothiazolo[4,3-b]pyridin-3-amine;
(2R,6S)-4-(6-(3,4-dimethoxyphenyl)isothiazolo[4,3-b]pyridin-3-yl)-2,6-dimethylmorpholine;
8-(6-(3,4-dimethoxyphenyl)isothiazolo[4,3-b]pyridin-3-yl)-1,4-dioxa-8-azaspiro[4.5]decane;
6-(3,4-dimethoxyphenyl)-3-phenylisothiazolo[4,3-b]pyridine;
6-(3,4-dimethoxyphenyl)-3-(pyridin-4-yl)isothiazolo[4,3-b]pyridine;
6-(3,4-dimethoxyphenyl)-3-(thiophen-3-yl)isothiazolo[4,3-b]pyridine;
6-(3,4-dimethoxyphenyl)isothiazolo[4,3-b]pyridine;
6-(2-bromo-4,5-dimethoxyphenyl)-3-(4-methylpiperidin-1-yl)isothiazolo[4,3-b]pyridine; and
6-(2-bromo-4,5-dimethoxyphenyl)-3-ethoxyisothiazolo[4,3-b]pyridine.

6. An isothiazolo[4,3-b]pyridine derivative according to any of statements 1 to 5 for use as a medicine.

7. An isothiazolo[4,3-b]pyridine derivative according to any of statements 1 to 6 for use as a medicine for the prevention or treatment of cell-proliferative diseases in an animal.

8. An isothiazolo[4,3-b]pyridine derivative according to statement 7, wherein said cell-proliferative disease is cancer.

9. An isothiazolo[4,3-b]pyridine derivative according to statements 8, wherein said cell-proliferative disease is osteosarcoma or prostate cancer.

10. An isothiazolo[4,3-b]pyridine derivative according to any of statements 1 to 6 for use as a medicine for the prevention or treatment of a neurodegenerative disease in an animal.

11. An isothiazolo[4,3-b]pyridine derivative according to statement 10, wherein said neurodegenerative disease is Parkinson's disease.

12. An isothiazolo[4,3-b]pyridine derivative according to any of statements 7 to 11, wherein said animal is a human being.

13. A pharmaceutical composition comprising a therapeutically effective amount of an isothiazolo[4,3-b]pyridine derivative according to any of statements 1 to 5 and one or more pharmaceutically acceptable excipients.

14. A method of prevention or treatment of a cell-proliferative diseases in an animal, comprising the administration of a therapeutically effective amount of an isothiazolo[4,3-b]pyridine derivative according to any of statements 1 to 5, optionally in combination with one or more pharmaceutically acceptable excipients.

15. An isothiazolo[4,3-b]pyridine derivative according to any one of statements 1 to 4, wherein $R^6$ is a dimethoxyphenyl or a trimethoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl.

16. An isothiazolo[4,3-b]pyridine derivative according to any one of statements 1 to 4, wherein $R^6$ is a thienyl, for example 3-thienyl or 2-thienyl.

17. An isothiazolo[4,3-b]pyridine derivative according to any one of statements 1 to 4, wherein $R^6$ is a methoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl.

18. An isothiazolo[4,3-b]pyridine derivative according to any one of statements 1 to 4, or 17, wherein $R^6$ is a 3-methoxyphenyl or 4-methoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl.

19. An isothiazolo[4,3-b]pyridine derivative according to any one of statements 1 to 4, wherein $R^6$ is selected from 3,4-dimethoxyphenyl, 4-methoxycarbonyl-3-methoxyphenyl, 4-amino-3-methoxyphenyl, 3-methoxy-4-hydroxyphenyl, 3,5-dimethoxyphenyl, 2-bromo-4,5-dimethoxyphenyl, 3,4,5-trimethoxyphenyl and 4-amino-3-methoxyphenyl.

20. An isothiazolo[4,3-b]pyridine derivative according to any one of statements 1 to 4, 17, wherein $R^6$ is acetoxymethoxyphenyl, such as 4-acetoxy-3-methoxyphenyl and 3-acetoxy-4-methoxyphenyl.

21. An isothiazolo[4,3-b]pyridine derivative according to any one of statements 1 to 4, 15, wherein $R^6$ is 2,5-dimethoxyphenyl; 3,4-dimethoxyphenyl, 3,5-dimethoxyphenyl, or 4,5-dimethoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl, such as 2-bromo-4,5-dimethoxyphenyl.

22. An isothiazolo[4,3-b]pyridine derivative according to any one of statements 1 to 4, wherein $R^6$ is furanyl, such as 3-furanyl.

23. An isothiazolo[4,3-b]pyridine derivative according to any one of statements 1 to 4, wherein $R^6$ is N-methylbenzamide, for example 4-(N-methylaminocarbonyl)phenyl.

24. An isothiazolo[4,3-b]pyridine derivative according to any one of statements 1 to 4, 15 to 23, wherein $R^3$ is a morpholinyl, optionally substituted with one or more substituents selected from the group consisting of a halogen, $C_{1-4}$ alkyl, amino, trifluoromethyl, hydroxyl, sulfhydryl, nitro, methoxy, acetoxy, and methoxycarbanoyl, such as 2,6-dimethylmorpholinyl.

25. An isothiazolo[4,3-b]pyridine derivative according to any one of statements 1 to 4, 15 to 24, wherein $R^3$ is a (mono- or di-) $C_{1-4}$ alkyl substituted morpholinyl or a (mono- or di-) $C_{1-2}$ alkyl substituted morpholinyl.

26. An isothiazolo[4,3-b]pyridine derivative according to any one of statements 1 to 4, 15 to 23, wherein $R^3$ is thiomorpholinyl.

27. An isothiazolo[4,3-b]pyridine derivative according to any one of statements 1 to 4, 15 to 23, wherein $R^3$ is piperidinyl optionally substituted with one or more substituents selected from the group consisting of a halogen, $C_{1-2}$ alkyl, amino, trifluoromethyl, hydroxyl, sulfhydryl, nitro, methoxy, acetoxy, and methoxycarbanoyl, such as 4-hydroxypiperidinyl or 3-hydroxypiperidinyl.

28. An isothiazolo[4,3-b]pyridine derivative according to any one of statements 1 to 4, 15 to 23, wherein $R^3$ is 4-piperidinone.

29. An isothiazolo[4,3-b]pyridine derivative according to any one of statements 1 to 4, 15 to 23, wherein $R^3$ is (mono- or di-)$C_{1-7}$ alkylamino, such as dimethylamino and diethylamino.

30. An isothiazolo[4,3-b]pyridine derivative according to any one of statements 1 to 4, 15 to 23, wherein $R^3$ is (mono- or di-) hydroxy $C_{1-7}$ alkylamino, such as ethanolamino, n-pentanolamino, diethanolamino and 2,3-dihydroxy-propanylamino.

31. An isothiazolo[4,3-b]pyridine derivative according to any one of statements 1 to 4, 15 to 23, wherein $R^3$ is $C_{1-4}$ alkoxy$C_{1-4}$ alkyl amino such as methoxyethylamino.

32. An isothiazolo[4,3-b]pyridine derivative according to any one of statements 1 to 4, 15 to 23, wherein $R^3$ is $C_{3-10}$ cycloalkyl$C_{1-4}$ alkylamino, such as cyclopropylmethylamino.

33. An isothiazolo[4,3-b]pyridine derivative according to any one of statements 1 to 4, 15 to 23, wherein $R^3$ is $C_{1-7}$alkoxy, or $C_{1-4}$ alkoxy, such as ethoxy.

34. An isothiazolo[4,3-b]pyridine derivative according to any one of statements 1 to 4, 15 to 23, wherein $R^3$ is an aryl such as a phenyl.

35. An isothiazolo[4,3-b]pyridine derivative according to any one of statements 1 to 4, 15 to 23, wherein $R^3$ is a heteroaryl, such as pyridinyl and thienyl.

36. An isothiazolo[4,3-b]pyridine derivative according to any one of statements 1 to 4, 15 to 23, wherein when $R^3$ is an unsubstituted or substituted thiomorpholinyl, morpholinyl, pyrrolidinyl, piperazinyl or piperidinyl said $R^3$ is attached in formula I via its nitrogen atom.

One embodiment of the present invention concerns a compound according to the invention, including the isothiazolo[4,3-b]pyridine of formula (I), wherein $R^6$ is a dimethoxyphenyl or a trimethoxyphenyl. Another embodiment of the present invention concerns a compound according to the invention, including the isothiazolo[4,3-b]pyridine of formula (I), wherein $R^6$ is a thienyl. Another embodiment of the present invention concerns a compound according to the invention, including the isothiazolo[4,3-b]pyridine of formula (I), wherein $R^6$ is a methoxyphenyl, more specifically a 3-methoxyphenyl or 4-methoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl, such as 3,4-dimethoxyphenyl, 4-methoxycarbonyl-3-methoxy-phenyl, 4-amino-3-methoxyphenyl, 3-methoxy-4-hydroxyphenyl, 3,5-dimethoxyphenyl, 2-bromo-4,5-dimethoxyphenyl, 3,4,5-trimethoxyphenyl and 4-amino-3-methoxyphenyl.

DETAILED DESCRIPTION OF THE INVENTION AND DEFINITIONS

Scheme 1 schematically shows a method for making 3,6-disubstituted isothiazolo[4,3-b]pyridine derivatives.

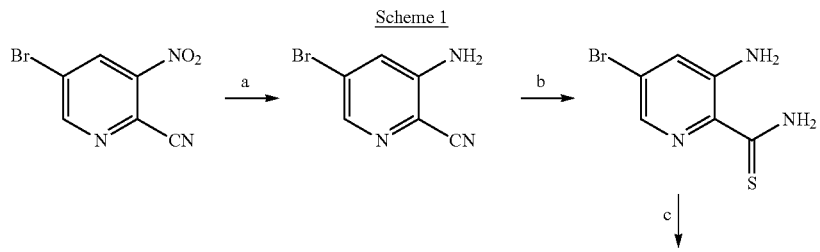

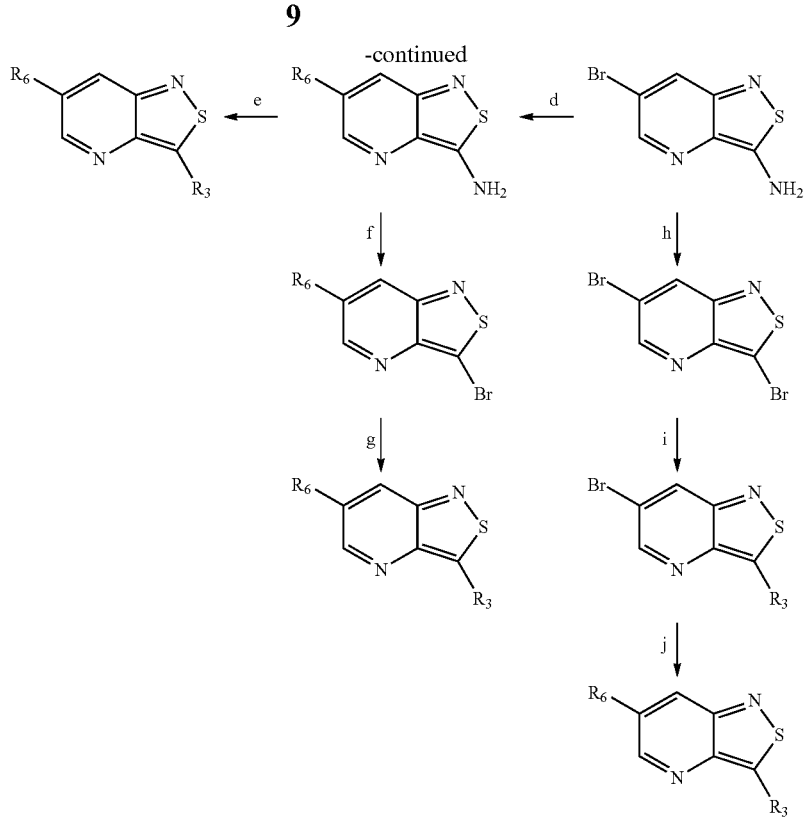

The nitro group of 3-nitro-5-bromopyridine-2-carbonitrile is reduced in step (a) either catalytically (e.g. by using platinum or palladium under an atmosphere of hydrogen) or chemically (e.g. by using iron or tin under acidic conditions). The aromatic thioamide can then be obtained by treatment of the corresponding nitrile with gaseous hydrogen sulfide in the presence of alkali metal sulfide or ammonium sulfide in alcohols. Alternatively, thionation agents (such as phosphorus pentasulfide or Lawesson's reagent) can be used in step (b). An oxidative ring closure using hydrogen peroxide, yields then the isothiazolo[4,3-b]pyridine scaffold in step (c). The bromine on the pyridine moiety can be used as leaving group for a variety of palladium-catalyzed reactions such as, but not limited to, a Suzuki reaction (by reaction with an arylboronic acid), a Heck reaction (by reaction with a terminal alkene), a Sonogashira reaction (by reaction with a terminal alkyne), a Buchwald-Hartwig coupling (by reaction with amines) in step (d), yielding 3-amino-6-substituted isothiazolo[4,3-b]pyridine analogues. The amino group can be used for further derivatisation by coupling with acid chlorides (yielding amides), by reaction with iso(thio)cyanates affording (thio)urea analogues, by coupling with sulfonyl chlorides (furnishing sulfonamides), by reaction with chloroformates (yielding carbamates) in step (e). Alternatively, reductive amination with aldehydes in step (e) is also feasible, yielding 3-alkylamino-6-substituted isothiazolo[4,3-b]pyridine derivatives. In step (f), a diazotation reaction furnished the 3-bromo-6-substituted-isothiazolo[4,3-b]pyridine analogue. This bromo derivative can be used in step (g) for a wide variety of palladium-catalyzed cross-coupling reactions yielding 3,6-disubstituted isothiazolo[4,3-b]pyridine analogues. Alternatively, a diazotation reaction in step (h) afforded the 3,6-dibromo-isothiazolo[4,3-b]pyridine. Treatment with a suitable nucleophile, bearing the general formula $R_3H$ (amines, thiols or alkoxides) yielded a 3-$R_3$-substituted-6-bromo-isothiazolo[4,3-b]pyridine analogue in step (i). Palladium-catalyzed reactions allow to introduce structural variety in step (j) at position 6 of the isothiazolo[4,3-b]pyridine scaffold.

According to one embodiment, the present invention encompasses the isothiazolo[4,3-b]pyridine derivatives of the general formula I:

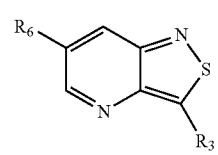

I wherein
$R_3$ is selected from the group consisting of halogen, amino, morpholinyl, thiomorpholinyl, pyrrolidinyl, piperazinyl, homopiperazinyl, piperidinyl, (mono- or di-) $C_{1-12}$ alkylamino, (mono- or di-) $C_{2-12}$ alkenylamino, (mono- or di-) $C_{2-12}$ alkynylamino, monoarylamino; diarylamino; (mono- or di-) $C_{3-10}$ cycloalkylamino, $C_{3-10}$cycloalkyl$C_{1-4}$ alkylamino, (mono- or di-) $C_{3-10}$ cycloalkenylamino, (mono- or di-) hydroxy $C_{1-7}$ alkylamino, (mono- or di-) $C_{1-4}$ alkylarylamino, (mono- or di-) aryl$C_{1-4}$ alkylamino, mercapto $C_{1-7}$ alkyl, $C_{1-7}$ alkoxy, $C_{1-4}$ alkoxy$C_{1-4}$ alkylamino, alkoxyaryl, $C_{3-10}$ cycloalkoxy, heterocyclic-substituted alkylamino, heterocyclic-substituted arylamino, heterocyclic amino, hydroxy-alkylamino, mercaptoalkylamino, hydroxypiperidinyl, aryl and heteroaryl groups, and, wherein said morpholinyl, thiomorpholinyl, pyrrolidinyl, piperazinyl, piperidinyl, heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$alkoxy, and, wherein one or more carbon atoms in any ring group may be replaced with —C(=O)—;

$R_6$ is selected from the group consisting of halogen, heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino;

and/or a pharmaceutical acceptable addition salt thereof and/or a stereoisomer thereof and/or a solvate thereof.

One embodiment of the present invention concerns a compound according to the invention, including the isothiazolo[4,3-b]pyridine of formula (I), wherein $R^6$ is a dimethoxyphenyl or a trimethoxyphenyl. Another embodiment of the present invention concerns a compound according to the invention, including the isothiazolo[4,3-b]pyridine of formula (I), wherein $R^6$ is a thienyl. Another embodiment of the present invention concerns a compound according to the invention, including the isothiazolo[4,3-b]pyridine of formula (I), wherein $R^6$ is a methoxyphenyl, more specifically a 3-methoxyphenyl or 4-methoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl, such as 3,4-dimethoxyphenyl, 4-methoxycarbonyl-3-methoxy-phenyl, 4-amino-3-methoxyphenyl, 3-methoxy-4-hydroxyphenyl, 3,5-dimethoxyphenyl, 2-bromo-4,5-dimethoxyphenyl, 3,4,5-trimethoxyphenyl and 4-amino-3-methoxyphenyl.

One embodiment of the present invention concerns a compound according to the invention, including the isothiazolo[4,3-b]pyridine of formula (I), wherein $R^6$ is selected from the group consisting of 3,4-dimethoxyphenyl; 3-thienyl; phenyl; 2-thienyl; 4-methoxycarbonyl-3-methoxy-phenyl; 4-acetoxy-3-methoxyphenyl; 3-acetoxy-4-methoxyphenyl; 3-methoxyphenyl; 4-methoxyphenyl; 3-furanyl; N-methylbenzamide; 3-methoxy-4-hydroxyphenyl; 3,5-dimethylphenyl; 2,5-dimethoxyphenyl; 2-bromo-4,5-dimethoxyphenyl; 3,4,5-trimethoxyphenyl and 4-amino-3-methoxyphenyl. In an embodiment said $R^6$ is 3,4-dimethoxyphenyl. In another embodiment said $R^6$ is 3-thienyl. In another embodiment said $R^6$ is phenyl. In another embodiment said $R^6$ is 2-thienyl. In another embodiment said $R^6$ is 4-methoxycarbonyl-3-methoxy-phenyl. In another embodiment said $R^6$ acetoxymethoxyphenyl, such as 4-acetoxy-3-methoxyphenyl and 3-acetoxy-4-methoxyphenyl. In another embodiment said $R^6$ 2,5-dimethoxyphenyl or 3,5-dimethoxyphenyl. In another embodiment said $R^6$ is a dimethoxyphenyl, such as 2,5-dimethoxyphenyl; 3,4-dimethoxyphenyl, 3,5-dimethoxyphenyl, or 4,5-dimethoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl, such as 2-bromo-4,5-dimethoxyphenyl. In another embodiment said $R^6$ is trimethoxyphenyl, such as 3,4,5-trimethoxyphenyl. In another embodiment said $R^6$ is 4-amino-3-methoxyphenyl. In another embodiment said $R^6$ is furanyl, such as 3-furanyl. In another embodiment said $R^6$ is N-methylbenzamide. One embodiment of the present invention concerns a compound according to the invention, including the isothiazolo[4,3-b] pyridine of formula (I), wherein $R^3$ is selected from the group consisting of morpholinyl, ethanolamino, thiomorpholinyl, piperidinyl, 4-piperidinone, 4-hydroxypiperidinyl, 3-hydroxypiperidinyl, n-pentanolamino, tetrahydropyranyl-4-amino, diethanolamino, 2,3-dihydroxy-propanylamino, pyrrolidinyl, methoxyethylamino, cyclopropylmethylamino, dimethylamino, diethylamino, 2,6-dimethylmorpholinyl, phenyl, pyridinyl, thienyl and ethoxy. In an embodiment said $R^3$ is morpholinyl. In certain embodiments $R^3$ is a substituted morpholinyl, wherein said morpholinyl is substituted with one or more substituents selected from the group consisting of a halogen, $C_{1-4}$ alkyl, amino, trifluoromethyl, hydroxyl, sulfhydryl, nitro, methoxy, acetoxy, and methoxycarbanoyl, such as 2,6-dimethylmorpholinyl. In another embodiment said $R^3$ is a (mono- or di-) $C_{1-4}$ alkyl substituted morpholinyl or a (mono- or di-) $C_{1-2}$ alkyl substituted morpholinyl. In another embodiment said $R^3$ is thiomorpholinyl. In another embodiment said $R^3$ is piperidinyl. In another embodiment said $R^3$ is a piperidinyl, optionally substituted with one or more substituents selected from the group consisting of a halogen, $C_{1-2}$ alkyl, amino, trifluoromethyl, hydroxyl, sulfhydryl, nitro, methoxy, acetoxy, and methoxycarbanoyl, such as 4-hydroxypiperidinyl or 3-hydroxypiperidinyl. In another embodiment said $R^3$ is 4-piperidinone. In another embodiment said $R^3$ is (mono- or di-)$C_{1-7}$alkylamino, such as dimethylamino and diethylamino. In another embodiment said $R^3$ is (mono- or di-) hydroxy $C_{1-7}$ alkylamino, such as ethanolamino, n-pentanolamino, diethanolamino and 2,3-dihydroxy-propanylamino. In another embodiment said $R^3$ is tetrahydropyran-4-amino. In another embodiment said $R^3$ is pyrrolidinyl. In another embodiment said $R^3$ is $C_{1-4}$alkoxy$C_{1-4}$ alkyl amino such as methoxyethylamino. In another embodiment said $R^3$ is $C_{3-10}$ cycloalkyl$C_{1-4}$ alkylamino, such as cyclopropylmethylamino. In another embodiment said $R^3$ is $C_{1-7}$alkoxy, or $C_{1-4}$ alkoxy, such as ethoxy. In another embodiment said $R^3$ is an aryl such as a phenyl. In another embodiment said $R^3$ is a heteroaryl, such as pyridinyl and thienyl.

In a particular embodiment, when $R^3$ is an unsubstituted or substituted thiomorpholinyl, morpholinyl, pyrrolidinyl, piperazinyl or piperidinyl said $R^3$ is attached in formula I via its nitrogen atom.

In a particular embodiment, the present invention also relates to the isothiazolo[4,3-b]pyridine derivatives of formula I, being selected from the group consisting of:

3-morpholino-6-phenyl-isothiazolo[4,3-b]pyridine;
3-morpholino-6-(4-fluoro-phenyl)isothiazolo[4,3-b]pyridine;
3-morpholino-6-(3-pyridyl))-isothiazolo[4,3-b]pyridine;
3-morpholino-6-(3,4-dimethoxyphenyl)-isothiazolo[4,3-b]pyridine;
3-morpholino-6-(3-thienyl)-isothiazolo[4,3-b]pyridine;
3-ethanolamino-6-(3-pyridyl)-isothiazolo[4,3-b]pyridine;

3-ethanolamino-6-(3,4-dimethoxyphenyl)-isothiazolo[4,3-b]pyridine;
3-ethanolamino-6-(3-thienyl)-isothiazolo[4,3-b]pyridine;
3-ethanolamino-6-(3-phenyl)-isothiazolo[4,3-b]pyridine;
3-methoxy-6-phenyl-isothiazolo[4,3-b]pyridine;
3-methoxy-6-(4-fluoro-phenyl)isothiazolo[4,3-b]pyridine;
3-methoxy-6-(3-pyridyl)-isothiazolo[4,3-b]pyridine;
3-methoxy-6-(3,4-dimethoxyphenyl)-isothiazolo[4,3-b]pyridine;
3-methoxy-6-(3-thienyl)isothiazolo[4,3-b]pyridine;
3-(N-Me-piperazinyl)-6-phenyl-isothiazolo[4,3-b]pyridine;
3-(N-Me-piperazinyl)-6-(3-pyridyl)-isothiazolo[4,3-b]pyridine;
3-(N-Me-piperazinyl)-6-(3,4-dimethoxyphenyl)-isothiazolo[4,3-b]pyridine;
3-(N-Me-piperazinyl)-6-(3-thienyl)isothiazolo[4,3-b]pyridine;
3-(N-Me-piperazinyl)-6-(4-fluorophenyl)-isothiazolo[4,3-b]pyridine;
3-amino-6-phenyl-isothiazolo[4,3-b]pyridine;
3-amino-6-(3-pyridyl)-isothiazolo[4,3-b]pyridine;
3-amino-6-(3,4-dimethoxyphenyl)-isothiazolo[4,3-b]pyridine;
3-amino-6-(4-fluorophenyl)-isothiazolo[4,3-b]pyridine;
3-amino-6-(3-thienyl)-isothiazolo[4,3-b]pyridine;
4-(6-(Thiophen-2-yl)isothiazolo[4,3-b]pyridin-3-yl)morpholine;
4-(6-(2,5-Dimethoxyphenyl)isothiazolo[4,3-b]pyridin-3-yl)morpholine;
4-(6-(2,4-Dimethoxyphenyl)isothiazolo[4,3-b]pyridin-3-yl)morpholine;
Methyl 2-methoxy-4-(3-morpholinoisothiazolo[4,3-b]pyridin-6-yl)benzoate;
2-Methoxy-4-(3-morpholinoisothiazolo[4,3-b]pyridin-6-yl)phenyl acetate;
4-(6-(3,5-Dimethoxyphenyl)isothiazolo[4,3-b]pyridin-3-yl)morpholine;
4-(6-(3,4,5-Trimethoxyphenyl)isothiazolo[4,3-b]pyridin-3-yl)morpholine;
2-Methoxy-4-(3-morpholinoisothiazolo[4,3-b]pyridin-6-yl)aniline;
4-(6-(Benzo[d][1,3]dioxol-5-yl)isothiazolo[4,3-b]pyridin-3-yl)morpholine;
4-(6-(Furan-3-yl)isothiazolo[4,3-b]pyridin-3-yl)morpholine;
Methyl 4-(3-morpholinoisothiazolo[4,3-b]pyridin-6-yl)benzoate;
N-Methyl-4-(3-morpholinoisothiazolo[4,3-b]pyridin-6-yl)benzamide;
6-bromo-3-(piperidin-1-yl)isothiazolo[4,3-b]pyridine;
6-bromo-3-thiomorpholinoisothiazolo[4,3-b]pyridine;
3-morpholino-6-aryl-isothiazolo[4,3-b]pyridines;
6-(3,4-dimethoxyphenyl)-3-(piperidin-1-yl)isothiazolo[4,3-b]pyridine;
6-(3,4-dimethoxyphenyl)-3-thiomorpholinoisothiazolo[4,3-b]pyridine;
3-bromo-6-(2-bromo-4,5-dimethoxyphenyl)isothiazolo[4,3-b]pyridine;
4-(6-(2-bromo-4,5-dimethoxyphenyl)isothiazolo[4,3-b]pyridin-3-yl)morpholine;
4-(6-(3-methoxyphenyl)isothiazolo[4,3-b]pyridin-3-yl)morpholine;
2-methoxy-5-(3-morpholinoisothiazolo[4,3-b]pyridin-6-yl)phenyl acetate;
4-(6-(4-methoxyphenyl)isothiazolo[4,3-b]pyridin-3-yl)morpholine;
1-(6-(3,4-dimethoxyphenyl)isothiazolo[4,3-b]pyridin-3-yl)piperidin-4-one;
1-(6-(3,4-dimethoxyphenyl)isothiazolo[4,3-b]pyridin-3-yl)piperidin-4-ol;
5-(6-(3,4-dimethoxyphenyl)isothiazolo[4,3-b]pyridin-3-ylamino)pentan-1-ol;
1-(6-(3,4-dimethoxyphenyl)isothiazolo[4,3-b]pyridin-3-yl)piperidin-3-ol;
6-(3,4-dimethoxyphenyl)-N-(tetrahydro-2H-pyran-4-yl)isothiazolo[4,3-b]pyridin-3-amine;
2,2'-(6-(3,4-dimethoxyphenyl)isothiazolo[4,3-b]pyridin-3-ylazanediyl)diethanol;
3-(6-(3,4-dimethoxyphenyl)isothiazolo[4,3-b]pyridin-3-ylamino)propane-1,2-diol;
ethyl-4-(6-(3,4-dimethoxyphenyl)isothiazolo[4,3-b]pyridin-3-ylamino)piperidine-1-carboxylate;
6-(3,4-dimethoxyphenyl)-3-(pyrrolidin-1-yl)isothiazolo[4,3-b]pyridine;
6-(3,4-dimethoxyphenyl)-N-phenethylisothiazolo[4,3-b]pyridin-3-amine;
6-(3,4-dimethoxyphenyl)-N-(2-methoxyethyl)isothiazolo[4,3-b]pyridin-3-amine;
N-(cyclopropylmethyl)-6-(3,4-dimethoxyphenyl)isothiazolo[4,3-b]pyridin-3-amine;
6-(3,4-dimethoxyphenyl)-N,N-dimethylisothiazolo[4,3-b]pyridin-3-amine;
6-(3,4-dimethoxyphenyl)-N,N-diethylisothiazolo[4,3-b]pyridin-3-amine;
(2R,6S)-4-(6-(3,4-dimethoxyphenyl)isothiazolo[4,3-b]pyridin-3-yl)-2,6-dimethylmorpholine;
8-(6-(3,4-dimethoxyphenyl)isothiazolo[4,3-b]pyridin-3-yl)-1,4-dioxa-8-azaspiro[4.5]decane;
6-(3,4-dimethoxyphenyl)-3-phenylisothiazolo[4,3-b]pyridine;
6-(3,4-dimethoxyphenyl)-3-(pyridin-4-yl)isothiazolo[4,3-b]pyridine;
6-(3,4-dimethoxyphenyl)-3-(thiophen-3-yl)isothiazolo[4,3-b]pyridine;
6-(3,4-dimethoxyphenyl)isothiazolo[4,3-b]pyridine;
6-(2-bromo-4,5-dimethoxyphenyl)-3-(4-methylpiperidin-1-yl)isothiazolo[4,3-b]pyridine; and
6-(2-bromo-4,5-dimethoxyphenyl)-3-ethoxyisothiazolo[4,3-b]pyridine.

In another particular embodiment, the invention relates to a group isothiazolo[4,3-b]pyridine derivatives, including the ones represented by the above mentioned structural formula (I), as well as pharmaceutical compositions comprising such isothiazolo[4,3-b]pyridine derivatives as active principle, represented by the above mentioned structural formula (I) and being in the form of a pharmaceutically acceptable salt. The latter include any therapeutically active nontoxic addition salt which compounds represented by structural formula (I) are able to form with a salt-forming agent. Such addition salts may conveniently be obtained by treating the isothiazolo[4,3-b]pyridine derivatives of the invention with an appropriate salt-forming acid or base. For instance, isothiazolo[4,3-b]pyridine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphthoate, hydroxyethanesulfonate, mandelate, methylsulfate, pantothenate, stearate, as well as salts derived from ethanedioic, propanediol, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like. Isothiazolo[4,3-b]pyridine derivatives of this invention, including the ones represented by the structural formula (I), having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, $N^1N^1$-dibenzylethylenediamine, chloroprocaine, choline, diethanolamine, ethylene-diamine, N-methylglucamine, procaine and the like.

Reaction conditions for treating the isothiazolo[4,3-b]pyridine derivatives of this invention, including the ones represented by the structural formula (I), with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the isothiazolo[4,3-b]pyridine derivative of this invention.

The present invention further provides the use of isothiazolo[4,3-b]pyridine derivatives of this invention, including the ones represented by the structural formula (I), or a pharmaceutically acceptable salt or a solvate thereof, as a biologically active ingredient, i.e. active principle, especially as a medicine or a diagnostic agent or for the manufacture of a medicament or a diagnostic kit. In a particular embodiment, said medicine or medicament may be for the prevention or treatment of cell-proliferative diseases. In another particular embodiment, said medicine or medicament may be for the prevention or treatment of neurodegenerative diseases.

The present invention also concerns the isothiazolo[4,3-b]pyridine derivatives of formula (I), any subgroup thereof, for use as a medicine.

The present invention also concerns the isothiazolo[4,3-b]pyridine derivatives of formula (I), any subgroup thereof, for use as a medicine for the prevention or treatment of cell-proliferative diseases in an animal.

In particular embodiments of the present invention, said cell-proliferative disease is cancer. In another particular embodiment, said cell-proliferative disease is osteosarcoma. In yet another particular embodiment said cell-proliferative disease is prostate cancer. In a yet more particular embodiment said cell-proliferative disease is hormone refractory prostate cancer.

The present invention also concerns the isothiazolo[4,3-b]pyridine derivatives of formula (I), any subgroup thereof, for use as a medicine for the prevention or treatment of cell-neurodegenerative diseases in an animal. In particular embodiments of the present invention, said neurodegenerative disease is Parkinson's disease.

In particular embodiments of the present invention, said animal is a mammal. In another, more particular embodiment, said animal is a human being.

The pathologic conditions and disorders concerned by the said use, and the corresponding methods of prevention or treatment, are detailed hereinbelow. Any of the uses mentioned with respect to the present invention may be restricted to a nonmedical use (e.g. in a cosmetic composition), a non-therapeutic use, a non-diagnostic use, a non-human use (e.g. in a veterinary composition), or exclusively an in-vitro use, or a use with cells remote from an animal. The invention further relates to a pharmaceutical composition comprising: (a) one or more isothiazolo[4,3-b]pyridine derivatives of this invention, including the ones represented by the structural formula (I), and (b) one or more pharmaceutically acceptable carriers.

The pathological conditions contemplated by this invention are cell-proliferative disorders or proliferative disorders of any kind, including cancer; other pathological conditions contemplated by this invention are neurodegenerative disorders, including Parkinson's disease.

As used herein and unless otherwise stated, the term "proliferative disorder" includes cancer or carcinoma's of any type, including soft tissue cancers and solid tissue cancers.

The term "cancer" or "tumor formation" refers to a mass of abnormal tissue that arises without obvious cause from pre-existing body cells, has no purposeful function, and is characterized by a tendency to autonomous and unrestrained growth. Examples of tumors or cancers envisaged in the context of the present invention include non-hematological cancers and hematological malignancies and such cancers/malignancies include but are not limited to cancer of the prostate, lung, breast, rectal, colon, lymph node, bladder, kidney, pancreatic, liver, ovarian, uterine, brain, skin, sarcoma, meningioma, glioblastoma, multiforme, skin, stomach, including all kinds of neuroblastoma, gastric carcinoma, renal cell carcinoma, neuroblastoma, gastric carcinoma, renal cell carcinoma, uterine cancer, muscle cancer or other tumors such as leukemia. The term "solid tumor" refers to non-metastased cancers or benign cancers (for a detailed description see below).

Particularly envisaged by the present invention are osteosarcomas and prostate cancer. The term "osteosarcomas" refers to any cancer types of the bone. Said osteosarcomas and the symptoms accompanied with said diseases or disorders are well known in the art and described in detail in medical text books such as Stedman or Pschyrembel. Accordingly, the clinician can determine without further ado whether a patient suffers from osteosarcoma.

One aspect of the disclosure relates to treatment or prevention of a prostate disease, including prostate cancer. In some embodiments, the compounds of this invention are used as a medicament for treatment or prevention of abnormal prostatic growths in an animal. The growths may be benign, such as benign prostatic hyperplasia, or may be associated with prostate cancer, for example, as an early or precursor stage of prostate cancer. One exemplary condition associated with development of prostate cancer is prostatic intraepithelial neoplasia.

In certain embodiments, the compounds of this invention, including the isothiazolo[4,3-b]pyridine derivatives of formula (I) and any subgroup thereof are used as a medicament for treatment or prevention of prostate cancer. In certain embodiments, the prostate cancer is a metastatic and/or aggressive form of prostate cancer. In some embodiments, the prostate cancer is adenocarcinoma. Adenocarcinoma is the most common form of prostate cancer, and is typically characterized by its origin in the peripheral zone (main glandular zone) of the prostate, and its development from epithelial cells. In further embodiments, the prostate cancer is a basal cell carcinoma, small cell carcinoma, squamous cell carcinoma, sarcoma, transitional cell carcinoma, or any combination of these. In addition, the prostate cancer may have developed from primary tumors that arose in other locations such as the bladder or urethra, and spread to the prostate. In some embodiments, the prostate cancer is in stage T1 or T2, according to the four-stage Tumor/Nodes/Metastasis (TNM) system. In certain embodiments, the prostate cancer may have spread outside of the prostate, and may be a stage T3 or T4 cancer. For example, a prostate cancer may have spread to the lymph nodes, bladder, urethra, rectum, bones, or other organs. In some embodiments, the medicaments described herein may prevent and/or slow a prostate cancer's progression to the next stage. In some embodiments, the prostate cancer has taken a form that does not respond to treatment and/or has become refractory. Often, prostate cancer is treated by administering compounds that disrupt the androgen signaling pathways essential for growth and survival of prostate cancer cells. For example, androgen receptor (AR) antagonists, also called anti-androgens, are administered in order to block binding of testosterone (T) and dihydrotestosterone (DHT) to the AR on prostate cancer cells. Initially, treatment with AR antagonists can prove successful in reducing the growth of prostate cancer cells. However, the prostate cancer can become refractive, and resume growth in spite of the treatment. When this occurs, the prostate cancer is known as a castration-resistant prostate cancer. This form of prostate cancer has also been previously termed "hormone refractory prostate cancer" and "androgen-independent prostate cancer." Castration-resistant prostate cancer may emerge at any time after initiating treatment of prostate cancer. In some embodiments, the castration-resistant prostate cancer emerges within at least 3, 4, 5, 6, 7, 8, 9, 10, or 11 months of treatment, or may emerge within 12, 13, 14, 15, 16, 17, 18, 19, 20, 21, 22 months, or within 2, 3, 4, or 5 years of treatment.

Thus, in certain embodiments, the compounds of this invention, including the isothiazolo[4,3-b]pyridine derivatives of formula (I) and any subgroup thereof are used as a medicament for treatment or prevention of castration-resistant prostate cancer. In some embodiments, the castration-resistant prostate cancer was previously treated with at least one AR antagonist, for example, at least one steroidal and/or at least one nonsteroidal AR antagonist. Exemplary nonsteroidal AR antagonists include but are not limited to Bicalutamide (Bic), Hydroxyflutamide (HOFI), Nilutamide, MDV3100, or its variant RD-162, and ARN-509. Accordingly, the prostate cancer may no longer respond to the dosages of an AR antagonist such as Bic, HOFI, Nilutamide, MDV3100, RD-162 and/or ARN-509 that had been therapeutically effective in the past.

The compounds of this invention, including the isothiazolo[4,3-b]pyridine derivatives of formula (I) and any subgroup thereof, are useful to inhibit cancer or tumor formation. Current research suggests that each tumor arises from a single cell that has been transformed by one or more events. Such events include the activation of oncogenes and the absence or inactivation of specific tumor-suppressor genes. These transformed cells can form small clones, initially co-opting normal host vessels, growing to only several millimeters in size before their supply of nutrients becomes limited. At this point, the tumor may lie dormant for prolonged periods (from months to years) until ultimately undergoing destruction by the immune system or switching to an angiogenic phenotype. This "switch" involves a shift in the local equilibrium between negative and positive endogenous regulators of angiogenesis. The tumor cells may achieve this shift in several ways, including the overexpression of angiogenic factors, the recruitment of host cells (such as macrophages) that can produce their own angiogenic factors, the mobilization of angiogenic proteins from the extracellular matrix (ECM), or a combination of these processes. If the production of proangiogenic factors is sufficiently robust, neighboring endothelial cells will be activated, leading to the sprouting of new capillaries.

Tumors are quite different from inflammatory or other swellings because the cells in tumors are abnormal in their appearance and other characteristics. Abnormal cells—the kind that generally make up tumors—differ from normal cells in having undergone one or more of the following alterations: (1) hypertrophy, or an increase in the size of individual cells; this feature is occasionally encountered in tumors but occurs commonly in other conditions; (2) hyperplasia or an increase in the number of cells within a given zone; in some instances it may constitute the only criterion of tumor formation; (3) anaplasia, or a regression of the physical characteristics of a cell toward a more primitive or undifferentiated type; this is an almost constant feature of malignant tumors, though it occurs in other instances both in health and in disease. In some instances the cells of a tumor are normal in appearance and are faithful reproductions of their parent types so that the differences between them and normal body cells are difficult to discern. Such tumors are also often benign. Other tumors are composed of cells that appear different from normal adult types in size, shape, and structure. They usually belong to tumors that are malignant. Such cells may be bizarre in form or be arranged in a distorted manner. In more extreme cases, the cells of malignant tumors are described as primitive, or undifferentiated, because they have lost the appearance and functions of the particular type of (normal) specialized cell that was their predecessor. As a rule, the less differentiated malignant tumor cells are, the more quickly that tumor may grow. Malignancy refers to the ability of a tumor to ultimately cause death. Any tumor, either benign or malignant in type, may produce death by local effects.

The common and more specific definition of malignancy implies an inherent tendency of the tumor's cells to metastasize (invade the body widely and become disseminated by subtle means) and eventually to kill the patient unless all the malignant cells can be eradicated. Metastasis is thus the outstanding characteristic of malignancy. Metastasis is the tendency of tumor cells to be carried from their site of origin by way of the circulatory system and other channels, which may eventually establish these cells in almost every tissue and organ of the body. The amount of new blood vessel growth can correlate with poor prognosis in several tumor types. Since the shedding of large numbers of tumor cells from the primary tumor may not begin until after the tumor has a sufficient network of blood vessels, angiogenesis may also correlate with metastatic potential. Destruction of the ECM is probably necessary to initiate the metastatic process.

Microvessel density has been correlated with cancer invasion and metastasis in a number of human tumors including breast, prostate, lung, esophageal, colorectal, endometrial and cervical.

In contrast to malignant tumor cells, the cells of a benign tumor invariably remain in contact with each other in one solid mass centered on the site of origin ("solid tumors"). Because of the physical continuity of benign tumor cells, they may be removed completely by surgery if the location is suitable. But the dissemination of malignant cells, each one individually possessing (through cell division) the ability to give rise to new masses of cells (new tumors) in new and distant sites, precludes complete eradication by a single surgical procedure in all but the earliest period of growth. A benign tumor may undergo malignant transformation, but the cause of such change is unknown. It is also possible for a malignant tumor to remain quiescent, mimicking a benign one clinically, for a long time. All benign tumors tend to remain localized at the site of origin. Many benign tumors are encapsulated. The capsule consists of connective tissue derived from the structures immediately surrounding the tumor.

Well-encapsulated tumors are not anchored to their surrounding tissues. These benign tumors enlarge by accretion, pushing aside the adjacent tissues without involving them intimately.

Among the major types of benign tumors are the following: lipomas, which are composed of fat cells; angiomas, which are composed of blood or lymphatic vessels; osteomas, which arise from bone; chondromas, which arise from cartilage; and adenomas, which arise from glands. For malignant tumors, examples comprise carcinomas (occur in epithelial tissues, which cover the body (the skin) and line the inner cavitary structures of organs (such as the breast, the respiratory and gastrointestinal tracts, the endocrine glands, and the genitourinary system). Sarcomas develop in connective tissues, including fibrous tissues, adipose (fat) tissues, muscle, blood vessels, bone, and cartilage. A cancer can also develop in both epithelial and connective tissue and is called a carcinosarcoma. Cancers of the blood-forming tissues (such as leukemias and lymphomas), tumors of nerve tissues (including the brain), and melanoma (a cancer of the pigmented skin cells) are classified separately.

The invention further relates to a method of prevention or treatment of a cell-proliferative disease in an animal, comprising the administration of a therapeutically effective amount of an isothiazolo[4,3-b]pyridine derivative according to this invention, including the isothiazolo[4,3-b]pyridine derivatives of formula (I) and any subgroup thereof, optionally in combination with one or more pharmaceutically acceptable excipients.

Certain compounds in accordance with this invention are potent inhibitors when measured in the in vitro cancer screen assays as described in the example section of this invention.

The term "pharmaceutically acceptable carrier or excipient" as used herein in relation to pharmaceutical compositions and combined preparations means any material or substance with which the active principle, i.e. the isothiazolo [4,3-b]pyridine derivative of this invention, including the ones represented by the structural formula (I), and optionally the antitumor compound may be formulated in order to facilitate its application or dissemination to the locus to be treated, for instance by dissolving, dispersing or diffusing said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders. Suitable pharmaceutical carriers for use in said pharmaceutical compositions and their formulation are well known to those skilled in the art. There is no particular restriction to their selection within the present invention although, due to the usually low or very low water-solubility of the isothiazolo[4,3-b]pyridine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents, may also be prepared by micronisation, for instance in view to obtain them in the form of microspheres usually having a diameter of about 1 to 10 μm, namely for the manufacture of microcapsules for controlled or sustained release of the biologically active ingredient(s). Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalenesulphonic acid or a naphthalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphosphatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals. A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants" (Chemical Publishing Co., New York, 1981). Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof. Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems including, but not limited to, liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered by way of intracavernosal injection, or may be administered topically, in an ointment, gel or the like, or transdermal, including transscrotally, using a conventional transdermal drug delivery system. Intracavernosal injection can be carried out by use of a syringe or any other suitable device. An example of a hypodermic syringe useful herein is described in U.S. Pat. No. 4,127,118, injection being made on the dorsum of the penis by placement of the needle to the side of each dorsal vein and inserting it deep into the corpora.

Another embodiment of this invention includes the various precursor or "prodrug" forms of the compounds of the present invention. It may be desirable to formulate the compounds of the present invention in the form of a chemical species which itself is not significantly biologically active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "prodrug" or "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome. The present invention will be further described with reference to certain more specific embodiments and examples, but the present invention is not limited thereto. The following examples are given by way of illustration only.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl(terbutyl), 2-methylbutyl, n-pentyl, dimethylpropyl, n-hexyl, 2-methylpentyl, 3-methylpentyl, n-heptyl and the like. By analogy, the term "$C_{1-12}$ alkyl" refers to such radicals having from 1 to 12 carbon atoms, i.e. up to and including dodecyl. By analogy, the term "$C_{1-2}$ alkyl" refers to such radicals having from 1 to 2 carbon atoms, i.e. including methyl and ethyl. By analogy, the term "$C_{1-4}$ alkyl" refers to such radicals having from 1 to 4 carbon atoms, i.e. up to and including butyl.

As used herein with respect to a substituting radical, and unless otherwise stated, the term "$C_{1-7}$ alkylene" means the divalent hydrocarbon radical corresponding to the above defined $C_{1-7}$ alkyl, such as methylene, bis(methylene), tris(methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkyl-alkyl" refers to an aliphatic saturated hydrocarbon monovalent radical (preferably a $C_{1-7}$ alkyl such as defined above) to which a $C_{3-10}$ cycloalkyl (such as defined above) is already linked such as, but not limited to, cyclohexylmethyl, cyclopentylmethyl and the like.

As used herein with respect to a substituting radical, and unless otherwise stated, the term "$C_{3-10}$ cycloalkylene" means the divalent hydrocarbon radical corresponding to the above defined $C_{3-10}$ cycloalkyl.

As used herein with respect to a substituting radical, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_4\beta$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, e.g. with respect to a substituting radical such as the combination of substituents in certain positions of isothiazolo[4,3-b]pyridine ring together with the carbon atoms in the same positions of said ring, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance said combination of substituents may form a $C_{2-6}$ alkylene radical, such as tetramethylene, which cyclizes with the carbon atoms in certain positions of the isothiazolo[4,3-b]pyridine ring.

As used herein with respect to a substituting radical (including the combination of substituents in certain positions of the isothiazolo[4,3-b]pyridine ring together with the carbon atoms in the same positions of said ring), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepine, benzodioxepinyl, benzodithiepinyl, benzoxazocinyl, benzo-thiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphtho-triazolyl, naphthopyranyl, oxabicycloheptyl, azabenzimidazolyl, azacycloheptyl, azacyclooctyl, azacyclononyl, azabicyclononyl, tetrahydrofuryl, tetrahydropyrarryl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiouraxolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazirryl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofutyl, furoyl, hydantoinyl, dioxolanyl, dioxolyl, dithianyl, dithienyl, dithiinyl, thienyl, indolyl, indazolyl, benzofutyl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimi-dazolyl, pyrazolinyl, pyrazolidinyl, pyrrolinyl, pyrrolidinyl, piperazinyl, uridinyl, thymidinyl, cytidinyl, azirinyl, aziridinyl, diazirinyi, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsulfinyl, benzylsulfanyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$alkylamino, cycloalkylamino, alkenylamino, cycloalkenylamino, alkynylamino, arylamino, arylalkylamino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, tricarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkyloxy", "oxyheterocyclic", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl or heterocyclic radical (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl, cresoxy, and the like.

As used herein with respect to a substituting atom, and unless otherwise stated, the term "halogen" or "halo" means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cyclohepta-dienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the terms "arylalkyl", "arylalkenyl" and "heterocyclic-substituted alkyl" refer to an aliphatic saturated or ethylenically unsaturated hydrocarbon monovalent radical (preferably a $C_{1-7}$alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl] ethyl, 1-amino-2-[indol-2-yl]ethyl, styryl, pyridylmethyl (including all isomers thereof), pyridylethyl, 2-(2-pyridyl) isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$alkyl, $C_{2-7}$ alkenyl or $C_{3-10}$ cycloalkyl radicals as defined above such as, but not limited to, o-toluyl, m-toluyl, p-toluyl, 2,3-xylyl, 2,4-xylyl, 3,4-xylyl, o-cumenyl, m-cumenyl, p-cumenyl, o-cymenyl, m-cymenyl, p-cymenyl, mesityl, ter-butylphenyl, lutidinyl (i.e. dimethylpyridyl), 2-methylaziridinyl, methyl-benzimidazolyl, methylbenzofuranyl, methylbenzothiazolyl, methylbenzotriazolyl, methylbenzoxazolyl and methylbenzselenazolyl.

As used herein with respect to a substituting radical, and unless otherwise stated, the term "alkoxyaryl" refers to an aryl radical (such as defined above) onto which is (are) bonded one or more $C_{1-7}$ alkoxy radicals as defined above, preferably one or more methoxy radicals, such as, but not limited to, 2-methoxyphenyl, 3-methoxyphenyl, 4-methoxyphenyl, 3,4-dimethoxyphenyl, 2,4,6-trimethoxyphenyl, methoxynaphthyl and the like.

As used herein with respect to a substituting radical, and unless otherwise stated, the terms "alkylamino", "cycloalkylamino", "alkenylamino", "cyclo-alkenylamino", "arylamino", "arylalkylamino", "heterocyclic-substituted alkylamino", "heterocyclic-substituted arylamino", "heterocyclic amino", "hydroxy-alkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic-substituted alkyl, heterocyclic-substituted aryl, heterocyclic (provided in this case the nitrogen atom is attached to a carbon atom of the heterocyclic ring), mono- or polyhydroxy $C_{1-7}$ alkyl, mono- or polymercapto $C_{1-7}$ alkyl, or $C_{2-7}$ alkynyl radical(s) (each of them as defined herein, respectively, and including the presence of optional substituents independently selected from the group consisting of halogen, amino, hydroxyl, sulfhydryl, $C_{1-7}$ alkyl, $C_{1-7}$ alkoxy, trifluoromethyl and nitro) is/are attached to a nitrogen atom through a single bond such as, but not limited to, anilino, 2-bromoanilino, 4-bromoanilino, 2-chloroanilino, 3-chloroanilino, 4-chloroanilino, 3-chloro-4-methoxyanilino, 5-chloro-2-methoxyanilino, 2,3-dimethylanilino, 2,4-dimethylanilino, 2,5-dimethylanilino, 2,6-dimethylanilino, 3,4-dimethylanilino, 2-fluoroanilino, 3-fluoroanilino, 4-fluoroanilino, 3-fluoro-2-methoxyanilino, 3-fluoro-4-methoxyanilino, 2-fluoro-4-methylanilino, 2-fluoro-5-methylanilino, 3-fluoro-2-methylanilino, 3-fluoro-4-methylanilino, 4-fluoro-2-methylanilino, 5-fluoro-2-methylanilino, 2-iodoanilino, 3-iodoanilino, 4-iodoanilino, 2-methoxy-5-methylanilino, 4-methoxy-2-methylanilino, 5-methoxy-2-methylanilino, 2-ethoxyanilino, 3-ethoxy-anilino, 4-ethoxyanilino, benzylamino, 2-methoxybenzylamino, 3-methoxybenzylamino, 4-methoxybenzylamino, 2-fluorobenzylamino, 3-fluorobenzylamino, 4-fluoro-benzylamino, 2-chlorobenzylamino, 3-chlorobenzylamino, 4-chlorobenzylamino, 2-aminobenzylamino, diphenylmethylamino, α-naphthylamino, methylamino, dimethylamino, ethylamino, diethylamino, isopropylamino, propenylamino, n-butylamino, ter-butylamino, dibutylamino, 1,2-diaminopropyl, 1,3-diaminopropyl, 1,4-diaminobutyl, 1,5-diaminopentyl, 1,6-diaminohexyl, morpholinomethylamino, 4-morpholinoanilino, hydroxymethylamino, β-hydroxyethylamino and ethynylamino; this definition also includes mixed disubstituted amino radicals wherein the nitrogen atom is attached to two such radicals belonging to two different sub-sets of radicals, e.g. an alkyl radical and an alkenyl radical, or to two different radicals within the same subset of radicals, e.g. methylethylamino; among di-substituted amino radicals, symmetrically-substituted amino radicals are more easily accessible and thus usually preferred from a standpoint of ease of preparation.

As used herein with respect to a substituting radical, and unless otherwise stated, the terms "(thio)carboxylic acid-ester", "(thio)carboxylic acid thioester" and "(thio)carboxylic acid amide" refer to radicals wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic-substituted alkylamino, heterocyclic amino, heterocyclic-substituted arylamino, hydroxyalkylamino, mercaptoalkylamino or alkynylamino (such as above defined, respectively). As used herein with respect to a substituting radical, and unless otherwise stated, the term "amino-acid" refers to a radical derived from a molecule having the chemical formula $H_2N$—CHR—$COOH_1$ wherein R is the side group of atoms characterising the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of formula (I) may possess, in particular all possible stereochemical and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a isothiazolo[4,3-b]pyridine derivative of this invention with a suitable inorganic solvent (e.g. hydrates) or organic solvent, such as but not limited to alcohols, ketones, esters, ethers, nitriles and the like.

EXAMPLES

General

For all reactions, analytical grade solvents were used. All moisture-sensitive reactions were carried out in oven-dried glass-ware (135° C.). $^1$H-NMR spectra were recorded on a Bruker Advance 300 ($^1$H-NMR: 300 MHz) using tetramethylsilane as internal standard for $^1$H-NMR spectra. Abbreviations used are: s=singlet, d=doublet, t=triplet, q=quartet, m=multiplet, br s=broad signal. Coupling constants are expressed in Hz. Precoated aluminum sheets (Fluke Silica gel/TLC-cards, 254 nm) were used for TLC. Column chromatography (CC) was performed on ICN silica gel 63-200, 60 Å.

Example 1

Synthesis of 3-amino-5-bromopyridine-2-carbonitrile

A solution of iron powder (3.36 g, 60 mmol) in acetic acid (15 ml) was stirred at 0° C. To this solution was added dropwise a solution of 3-nitro-5-bromopyridine-2-carbonitrile (2.51 g, 11 mmol) In acetic acid (15 ml). The reaction mixture was stirred at room temperature for two hours. Then, ethyl acetate (300 ml) was added and the mixture was filtered (paper filter). The filter cake was washed with ethylacetate. The filtrate was evaporated and partitioned between ethylacetate (500 ml) and water (250 ml). The organic phase was washed with a 1 N NaOH solution (ca. 200 ml). The combined organic phases were dried and evaporated in vacuo, yielding a mixture of two compounds, i.e. 3-amino-5-bromopyridine-2-carbonitrile (major compound) and 3-amino-5-bromopyridine-2-carboxamide (minor compound). This mixture was used as such in the next reaction.

Example 2

Synthesis of 3-amino-5-bromo-2-pyridinecarbothioamide

To a solution of a mixture of 3-amino-5-bromopyridine-2-carbonitrile and 3-amino-5-bromopyridine-2-carboxamide (crude from example 1) in ethanol (25 ml) was added phosphorus pentasulfide (2 eq; 4.84 g). The mixture was heated overnight at 75° C. The solvents were evaporated and the crude residue was purified by flash chromatography on silica, using a mixture of cyclohexane/ethyl acetate (in a ratio of 7:1) as mobile phase, yielding the title compound (3.36 gram crude).

Example 3

3-amino-6-bromo-Isothiazolo[4,3-b]pyridine

To a solution of 3-amino-5-bromo-2-pyridinecarbothioamide (as obtained in Example 2) in methanol (50 ml) was added dropwise a 30% $H_2O_2$ solution in water (3.5 ml) at 0° C. The reaction mixture was stirred overnight at room temperature and then cooled again to 0° C. The crystals were filtered off and washed with cold methanol yielding the title compound (1.6 g, 63%).

Examples 4-8

Synthesis of 3-amino-6-aryl-isothiazolo[4,3-b]pyridines

General Procedure

To a solution of 3-amino-6-bromo-isothiazolo[4,3-b]pyridine (166 mg, 0.72 mmol) in mixture of dioxane (10 ml) and water (1.5 ml) was added an appropriate boronic acid (2 eq), sodium carbonate (2 eq, 153 mg) and Pd(dppf)Cl$_2$ (0.1 eq, 59 mg) The reaction mixture was stirred overnight at 100° C. The reaction mixture was cooled down to room temperature and the reaction was partioned between ethylacetate (60 ml) and brine (30 ml). The aqueous phase was then extracted with ethyl acetate (40 ml). The combined organic phases were dried over MgSO$_4$ and evaporated in vacuo. The residue was purified by flash chromatography on silicagel yielding the pure title compounds. The following compounds were made according to this procedure:

Example 4

3-amino-6-phenyl-isothiazolo[4,3-b]pyridine

This compound was obtained using phenylboronic acid and the crude residue was purified by flash chromatography using a mixture of cyclohexane and ethylacetate (in a ratio of 4:1) as mobile phase, affording the title compound in 77% yield.

Example 5

3-amino-6-(3-pyridyl)-isothiazolo[4,3-b]pyridine

This compound was obtained using 3-pyridylboronic acid and the crude residue was purified by flash chromatography using a mixture of methanol and dichloromethane (in a ratio of 1:20) as mobile phase, affording the title compound in 75% yield.

$^1$H-NMR (300 MHz, DMSO-d$_6$): δ=7.52 (m, 1H, arom H), 7.95 (br s, 2H, NH$_2$), 8.02 (d, J=1.98 Hz, 1H, arom H), 8.24 (m, 1H, arom H), 8.66 (m, 2H, arom H), 9.03 (d, J=1.98 Hz, 1H, arom H) ppm.

Example 6

3-amino-6-(3,4-dimethoxyphenyl)-isothiazolo[4,3-b]pyridine

This compound was obtained using 3,4-dimethoxyphenylboronic acid and the crude residue was purified by flash chromatography using a mixture of methanol and dichloromethane (in a ratio of 1:40) as mobile phase, affording the title compound in 57% yield.

$^1$H-NMR (300 MHz, DMSO-d$_6$): δ=3.81 (s, 3H, OCH$_3$), 3.88 (s, 3H, OCH$_3$), 7.07 (d, J=8.89 Hz, 1H, arom H), 7.35 (m, 2H, arom H), 7.84 (br s, 2H, NH$_2$), 7.89 (d, J=1.92 Hz, 1H, arom H), 8.63 (d, J=1.95 Hz, 1H, arom H) ppm.

Example 7

3-amino-6-(4-fluorophenyl)-isothiazolo[4,3-b]pyridine

This compound was obtained using 4-fluorophenylboronic acid and the crude residue was purified by flash chromatography using a mixture of cyclohexane and ethylacetate (in a ratio of 4:1) as mobile phase, affording the title compound in 76% yield.

$^1$H-NMR (300 MHz, DMSO-$d_6$): δ=6.36 (br s, 2H, NH$_2$), 7.34 (m, 2H, arom H), 7.38 (d, J=3.1 Hz, 1H, arom H), 7.71 (m, 2H, arom H), 8.17 (d, J=1.92 Hz, 1H, arom H) ppm.

Example 8

3-amino-6-(3-thienyl)-isothiazolo[4,3-b]pyridine

This compound was obtained using 3-thienylboronic acid and the crude residue was purified by flash chromatography using a mixture of cyclohexane and ethylacetate (in a ratio of 3:2) as mobile phase, affording the title compound in 69% yield.

$^1$H-NMR (300 MHz, DMSO-$d_6$): δ=7.70 (m, 2H, arom H), 7.84 (br s, 2H, NH$_2$), 7.98 (d, J=1.89 Hz, 1H, arom H), 8.17 (q, J=1.32 Hz, 1H, arom H), 8.74 (d, J=1.95 Hz, 1H, arom H) ppm.

Example 9

Synthesis of 3,6-di-bromo-isothiazolo[4,3-b]pyridine

To a solution of 3-amino-6-bromo-isothiazolo[4,3-b]pyridine (115 mg, 0.5 mmol) in HBr (7 ml) at 0° C. was added portionwise sodium nitrite (3 eq, 104 mg). After 30 minutes, CuBr (2 eq, 144 mg) was added. The reaction mixture was stirred for two hours at 0° C. and then overnight at room temperature. The mixture was neutralized with solid potassium carbonate and extracted with ethyl acetate (2×15 ml). The combined organic phases were dried over MgSO$_4$ and evaporated in vacuo. The crude residue was purified by silicagel flash chromatography, the mobile phase being a mixture of cyclohexane and ethylacetate (in a ratio of 30:1), yielding the pure title compound (111 mg, 76%).

Example 10

Synthesis of 6-bromo-3-benzylamino-isothiazolo[4,3-b]pyridine

To a solution of 3,6-di-bromo-isothiazolo[4,3-b]pyridine (54 mg, 0.18 mmol) in ethanol (5 ml) was added benzylamine (3 eq, 61 μl). The reaction was stirred overnight at 75° C. The solvent was evaporated in vacuo the crude residue was purified by silicagel flash chromatography, the mobile phase being a mixture of cyclohexane and ethylacetate (in a ratio of 5:1), yielding the pure title compound (25 mg, 25%).

Examples 11-13

Synthesis of 6-bromo-3-substituted-isothiazolo[4,3-b]pyridines

General Procedure

To a solution of 3,6-di-bromo-isothiazolo[4,3-b]pyridine (150 mg, 0.51 mmol) in ethanol (10 ml) was added an appropriate nitrogen nucleophile (3 eq). The reaction was stirred overnight at 75° C. The solvent was evaporated in vacuo and the crude residue was purified by silicagel chromatography, the mobile phase being a mixture of cyclohexane and ethylacetate (in a ratio of 4:1), yielding the pure title compounds.

The following compounds were made according to this procedure:

Example 11

6-bromo-3-morpholino-isothiazolo[4,3-b]pyridine

This compound was made using morpholine as nucleophile and the crude residue was purified using a mixture of cyclohexane and ethylacetate (in a ratio of 4:1) as mobile phase, affording the title compound in 92% yield.

$^1$H-NMR (300 MHz, DMSO-$d_6$): δ=3.84 (br s, 4H, 2×NCH$_2$), 3.87 (br s, 4 H, 2×OCH$_2$), 8.15 (s, 1H, arom H), 8.37 (s, 1H, arom H) ppm.

Example 12

6-bromo-6-ethanolamino-isothiazolo[4,3-b]pyridine

This compound was made using ethanolamine as nucleophile and the crude residue was purified using a mixture of cyclohexane and ethylacetate (in a ratio gradually ranging from 1:1 to 1:4) as mobile phase, affording the title compound in 94% yield.

$^1$H-NMR (300 MHz, DMSO-$d_6$): δ=3.39 (q, J=5.75 Hz, 2H, NCH$_2$), 3.68 (q, J=5.68 Hz, 2H, OCH$_2$), 4.91 (t, J=5.57 Hz, 1H), 8.04 (d, J=2.01 Hz, 1H, arom H), 8.29 (d, J=1.98 Hz, 1H, arom H), 8.66 (t, J=5.78 Hz, 1H) ppm.

Example 13

6-bromo-3-(N-methyl-piperazino)-isothiazolo[4,3-b]pyridine

This compound was made using N-methyl-piperazine as nucleophile and the crude residue was purified using a mixture of methanol and dichloromethane (in a ratio of 3:100) as mobile phase, affording the title compound in 92% yield.

$^1$H-NMR (300 MHz, DMSO-$d_6$): δ=2.24 (s, 3H, NCH$_3$), 2.52 (m, 4H, 2×NCH$_2$), 3.88 (t, J=Hz, 4 H, 2×NCH$_2$), 8.12 (d, J=2.01 Hz, 1H, arom H), 8.36 (d, J=1.23 Hz, 1H, arom H) ppm.

Example 14

Synthesis of 3-methoxy-6-bromo-isothiazolo[4,3-b]pyridine

To a solution of 3,6-dibromo-isothiazolo[4,3-b]pyridine (700 mg, 2.38 mmol) in absolute methanol (50 ml) was added carefully at 0° C. sodium methoxide (2.5 eq, 322 mg) in small portions. The resulting reaction mixture was stirred overnight at room temperature and then heated at 55° C. for 8 hours. The reaction was cooled down to room temperature, neutralized with a 5% HCl solution and evaporated in vacuo. The residue was divided between ethyl acetate (250 ml) and water (150 ml). The organic phase was dried and evaporated. The crude residue was purified by silica gel flash chromatography, the mobile phase being a mixture of cyclohexane and ethylacetate (in a ratio gradually ranging from 5:1 to 4:1), yielding the pure title compound (558 mg, 96%).

$^1$H-NMR (300 MHz, DMSO-$d_6$): δ=4.35 (s, 3H, OCH$_3$), 8.37 (d, J=2.01 Hz, 1H, arom H), 8.60 (d, J=1.98 Hz, 1H, arom H) ppm.

Examples 23-27

Synthesis of 3-morpholino-6-aryl-isothiazolo[4,3-b]pyridines

General Procedure

To a solution of 3-morpholino-6-bromo-isothiazolo[4,3-b]pyridine (0.37 mmol) in DME (5 ml) and water (1 ml) was added an appropriate boronic acid (2 eq), sodium carbonate (2 eq, 78 mg) and Pd(dppf)Cl$_2$ (0.1 eq, 30 mg). The reaction was heated overnight at 75° C. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography, yielding the pure title compounds.

The following compounds were made according to this procedure:

Example 23

3-morpholino-6-phenyl-isothiazolo[4,3-b]pyridine

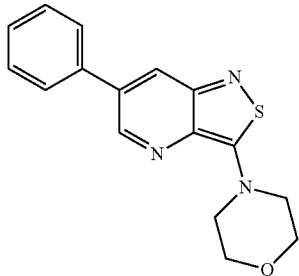 [SMILES: c1ccc(-c2cnc3c(N4CCOCC4)snc3c2)cc1]

This compound was prepared using phenylboronic acid and was purified using a mixture of cyclohexane/ethyl acetate in a ratio of 2:1, affording the title compound in 78% yield.

$^1$H-NMR (300 MHz, DMSO-d$_6$): δ=3.86 (br s, 4 H, 2×NCH$_2$), 3.90 (br s, 4H, 2×OCH$_2$), 7.50 (m, 3H, arom H), 7.82 (m, 2H, arom H), 8.01 (d, J=2.1 Hz, 1H, arom H), 8.72 (d, J=2.1 Hz, 1H, arom H) ppm.

Example 24

3-morpholino-6-(4-fluoro-phenyl)-isothiazolo[4,3-b]pyridine

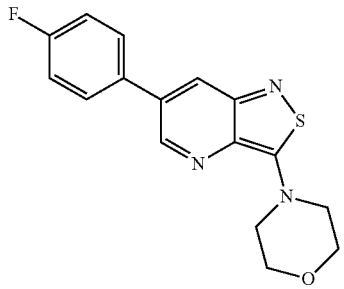 [SMILES: Fc1ccc(-c2cnc3c(N4CCOCC4)snc3c2)cc1]

This compound was prepared using 4-fluorophenylboronic acid and was purified using a mixture of cyclohexane/ethyl acetate in a ratio of 3:1, affording the title compound in 95% yield.

$^1$H-NMR (300 MHz, DMSO-d$_6$): δ=3.85 (br s, 4H, 2×NCH$_2$), 3.89 (br s, 4H, 2×OCH$_2$), 7.34 (t, J=8.82 Hz, 2H, arom H), 7.87 (m, 2H, arom H), 8.00 (d, J=2.04 Hz, 1H, arom H), 8.69 (d, J=2.04 Hz, 1H, arom H) ppm.

Example 25

3-morpholino-6-(3-pyridyl))-isothiazolo[4,3-b]pyridine

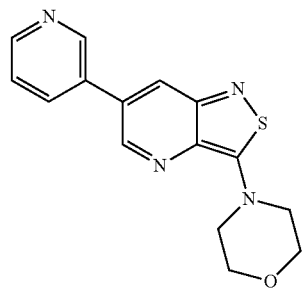 [SMILES: c1cncc(-c2cnc3c(N4CCOCC4)snc3c2)c1]

This compound was prepared using 3-pyridinyl boronic acid and was purified using a mixture of methanol/dichloromethane in a ratio of 1:25, affording the title compound in 80% yield.

$^1$H-NMR (300 MHz, DMSO-d$_6$): δ=3.86 (br s, 4H, 2×NCH$_2$), 3.91 (br s, 4H, 2×OCH$_2$), 7.55 (m, 1H, arom H), 8.15 (d, J=1.95 Hz, 2H, arom H), 8.26 (br d, 1 H, arom H), 8.65 (br d, 1H, arom H), 8.76 (d, J=1.92 Hz, 1H, arom H), 9.05 (br s, 1H, arom H) ppm.

Example 26

3-morpholino-6-(3,4-dimethoxyphenyl)-isothiazolo[4,3-b]pyridine

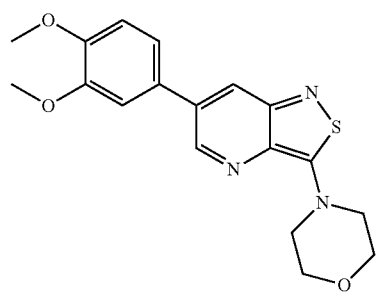 [SMILES: COc1ccc(-c2cnc3c(N4CCOCC4)snc3c2)cc1OC]

This compound was prepared using 3,4-dimethoxyphenylboronic acid and was purified using a mixture of cyclohexane/ethyl acetate in a ratio of 2:1, affording the title compound in 72% yield.

$^1$H-NMR (300 MHz, DMSO-d$_6$): δ=3.82 (s, 3H, OCH$_3$), 3.89 (br s, 11H, 2×NCH$_2$, 2×OCH$_2$ and OCH$_3$), 7.09 (d, J=8.04 Hz, 1H, arom H), 7.39 (m, 2H, arom H), 8.02 (d, J=2.01 Hz, 1 H, arom H), 8.75 (d, J=1.95 Hz, 1H, arom H) ppm.

Example 27

3-morpholino-6-(3-thienyl)-isothiazolo[4,3-b]pyridine

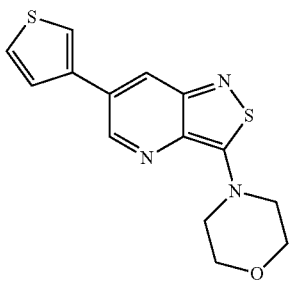

This compound was prepared using 3-thienylboronic acid and was purified using a mixture of cyclohexane/ethyl acetate in a ratio of 2:1, affording the title compound in 71% yield.

$^1$H-NMR (300 MHz, DMSO-d$_6$): δ=3.86 (br s, 4 H, 2×NCH$_2$), 3.88 (br s, 4H, 2×OCH$_2$), 7.73 (m, 1H, arom H), 7.77 (m, 1H, arom H), 8.09 (d, J=2.01 Hz, 1H, arom H), 8.21 (m, 1H, arom H), 8.84 (d, J=2.04 Hz, 1H, arom H) ppm.

Examples 28-32

Synthesis of 3-ethanolamino-6-aryl-isothiazolo[4,3-b]pyridines

General Procedure

To a solution of 3-ethanolamino-6-bromo-isothiazolo[4,3-b]pyridine (0.37 mmol) in dioxane (5 ml) and water (1 ml) was added an appropriate boronic acid (2 eq), sodium carbonate (2 eq, 78 mg) and Pd(dppf)Cl$_2$ (0.1 eq, 30 mg). The reaction was overnight at 75° C. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography yielding the pure title compounds The following compounds were made according to this procedure:

Example 28

3-ethanolamino-6-(3-pyridyl)-isothiazolo[4,3-b]pyridine

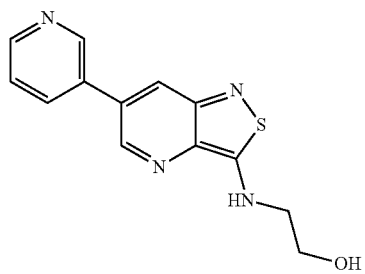 [SMILES: OCCNc1snc2cc(-c3cccnc3)cnc12]

This compound was prepared using 3-pyridyl boronic acid and was purified using a mixture of dichloromethane and methanol (in a ratio gradually ranging from 20:1 to 10:1), affording the title compound in 90% yield.

$^1$H-NMR (300 MHz, DMSO-d$_6$): δ=3.42 (q, J=5.67 Hz, 2H, NCH$_2$), 3.71 (t, J=5.64 Hz, 2H, OCH$_2$), 4.95 (br s, 1H), 7.54 (m, 1H, arom H), 8.05 (br s, 1H, arom H), 8.25 (br d, J=7.95 Hz, 1H, arom H), 8.52 (br t, 1H), 8.61 (m, 2H, arom H), 9.04 (d, J=2.13 Hz 1H, arom H) ppm.

Example 29

3-ethanolamino-6-(3,4-dimethoxyphenyl)-isothiazolo[4,3-b]pyridine

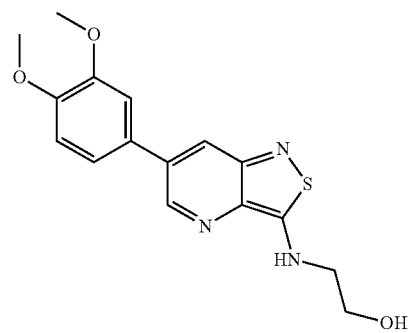 [SMILES: COc1ccc(-c2cnc3c(NCCO)snc3c2)cc1OC]

This compound was prepared using 3,4-dimethoxyphenylboronic acid and was purified using a mixture of dichloromethane and methanol (in a ratio 30:1), affording the title compound in 95% yield.

$^1$H-NMR (300 MHz, DMSO-d$_6$): δ=3.42 (q, J=5.62 Hz, 2H, NCH$_2$), 3.70 (q, J=5.42 Hz, 2H, OCH$_2$), 3.81 (s, 3H, OCH$_3$), 3.88 (s, 3H, OCH$_3$), 4.93 (t, J=5.67 Hz, 1H), 7.07 (d, J=8.34 Hz, 1H, arom H), 7.36 (m, 2H, arom H), 7.92 (s, 1H, arom H), 8.40 (t, J=5.55 Hz, 1 arom H), 8.64 (br s, 1H, arom H) ppm.

Example 30

3-ethanolamino-6-(3-thienyl)-isothiazolo[4,3-b]pyridine

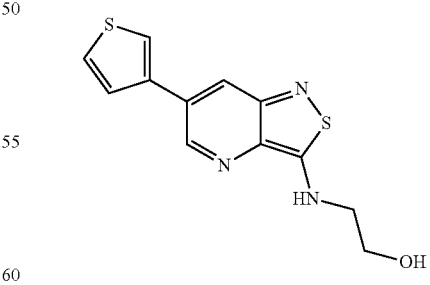

This compound was prepared using 3-thienylboronic acid and was purified using a mixture of dichloromethane and methanol (in a ratio 30:1), affording the title compound in 90% yield.

$^1$H-NMR (300 MHz, DMSO-d$_6$): δ=3.40 (q, J=5.58 Hz, 2H, NCH$_2$), 3.70 (q, J=5.64 Hz, 2H, OCH$_2$), 4.93 (t, J=5.49

Hz, 1H), 7.74 (m, 2H, arom H), 8.01 (br s, 1H, arom H), 8.19 (br s, 1 arom H), 8.42 (br t, 1H), 8.75 (br s, 1H, arom H) ppm.

Example 31

3-ethanolamino-6-phenyl-isothiazolo[4,3-b]pyridine

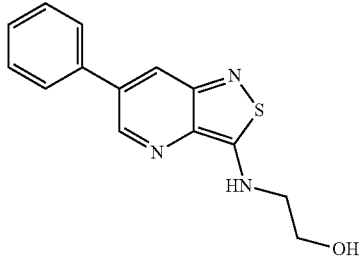 [SMILES: OCCNc1snc2cc(-c3ccccc3)cnc12]

This compound was prepared using phenylboronic acid and was purified using a mixture of dichloromethane and methanol (in a ratio 20:1), affording the title compound in 99% yield.

$^1$H-NMR (300 MHz, DMSO-$d_6$): δ=3.41 (q, J=5.80 Hz, 2H, NCH$_2$), 3.71 (q, J=5.61 Hz, 2H, OCH$_2$), 4.95 (t, J=5.52 Hz, 1H), 7.49 (m, 5H, arom H), 7.80 (br d, J=7.23 Hz, 1H, arom H), 7.91 (s, 1H, arom H), 8.50 (br t, 1H), 8.63 (d, J=1.59 Hz, 1H, arom H) ppm.

Example 32

3-ethanolamino-6-(3-(4-fluorophenyl))-isothiazolo[4,3-b]pyridine

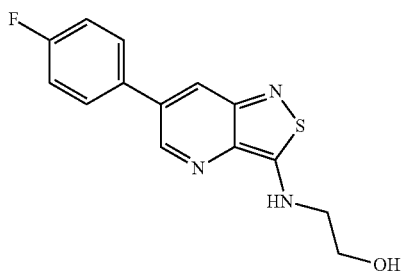 [SMILES: OCCNc1snc2cc(-c3ccc(F)cc3)cnc12]

This compound was prepared using 4-fluorophenylboronic acid and was purified using a mixture of dichloromethane and methanol (in a ratio 20:1), affording the title compound in 81% yield.

$^1$H-NMR (300 MHz, DMSO-$d_6$): δ=3.30 (2H, NCH$_2$, hidden under H$_2$O peak), 3.71 (q, J=5.61 Hz, 2H, OCH$_2$), 4.96 (t, J=5.45 Hz, 1H), 7.35 (t, J=8.64 Hz, 1H, arom H), 7.88 (m, 3H, arom H), 8.47 (br t, 1H), 8.62 (br s, 1H, arom H) ppm.

Examples 33-37

Synthesis of 3-methoxy-6-aryl-isothiazolo[4,3-b]pyridines

General Procedure

To a solution of 3-methoxy-6-bromo-isothiazolo[4,3-b]pyridine (100 mg, 0.41 mmol) in dioxane (5 ml) and water (1 ml) was added an appropriate boronic acid (2 eq), sodium carbonate (2 eq, 87 mg) and Pd(dppf)Cl$_2$ (0.1 eq, 33 mg). The reaction mixture was heated at 95° C. overnight. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography yielding the pure title compounds The following compounds were made according to this procedure:

Example 33

3-methoxy-6-phenyl-isothiazolo[4,3-b]pyridine

This compound was prepared using phenylboronic acid and the crude residue was purified using a mixture of cyclohexane and ethylacetate (in a ratio of 2:1), affording the title compound in 87% yield.

$^1$H-NMR (300 MHz, CDCl$_3$): δ=4.37 (s, 3H, OCH$_3$), 7.50 (m, 3H, arom H), 7.68 (m, 2H, arom H), 8.00 (d, J=2.01 Hz, 1H, arom H), 8.86 (d, J=1.98 Hz, 1H, arom H) ppm.

Example 34

3-methoxy-6-(4-fluoro-phenyl)-isothiazolo[4,3-b]pyridine

This compound was prepared using 4-fluoro-phenylboronic acid and the crude residue was purified using a mixture of cyclohexane and ethylacetate (in a ratio of 2:1), affording the title compound in 76% yield.

$^1$H-NMR (300 MHz, DMSO-$d_6$): δ=4.36 (s, 3H, OCH$_3$), 7.37 (t, J=8.79, 3H, arom H), 7.93 (m, 2H, arom H), 8.18 (d, J=1.98 Hz, 1H, arom H), 8.93 (d, J=1.92 Hz, 1H, arom H) ppm.

Example 35

3-methoxy-6-(3-pyridyl)-isothiazolo[4,3-b]pyridine

This compound was prepared using 3-pyridylboronic acid and the crude residue was purified using a mixture of methanol and dichloromethane (in a ratio of 1:30), affording the title compound in 55% yield.

$^1$H-NMR (300 MHz, DMSO-$d_6$): δ=4.40 (s, 3H, OCH$_3$), 7.57 (m, 1H, arom H), 8.31 (m, 2H, arom H), 8.67 (d, J=4.23 Hz, 1H, arom H), 8.99 (d, J=1.71 Hz, 1H, arom H), 9.09 (d, J=1.89 Hz, 1H, arom H) ppm.

Example 36

3-methoxy-6-(3,4-dimethoxyphenyl)-isothiazolo[4,3-b]pyridine

This compound was prepared using 3,4-dimethoxyphenylboronic acid and the crude residue was purified using a mixture of cyclohexane and ethylacetate (in a ratio of 1:1), affording the title compound in 74% yield.

$^1$H-NMR (300 MHz, DMSO-$d_6$): δ=3.82 (s, 3H, OCH$_3$), 3.89 (s, 3H, OCH$_3$), 4.35 (s, 3H, OCH$_3$), 7.09 (d, J=9 Hz, 1H, arom H), 7.42 (m, 2H, arom H), 8.16 (d, J=1.92 Hz, 1H, arom H), 8.97 (d, J=1.92 Hz, 1H, arom H) ppm.

Example 37

3-methoxy-6-(3-thienyl)-isothiazolo[4,3-b]pyridine

This compound was prepared using 3-thienyllboronic acid and the crude residue was purified using a mixture of cyclohexane and ethylacetate (in a ratio of 2:1), affording the title compound in 75% yield.

$^1$H-NMR (300 MHz, DMSO-$d_6$): δ=4.35 (s, 3H, OCH$_3$), 7.74 (m, 1H, arom H), 7.82 (m, 1H, arom H), 8.25 (d, J=1.98 Hz, 1H, arom H), 8.29 (m, 1H, arom H), 9.06 (d, J=1.95 Hz, 1H, arom H) ppm.

Examples 38-42

Synthesis of 3-(N-Me-piperazinyl)-6-aryl-isothiazolo[4,3-b]pyridines

General Procedure

To a solution of 3-(N-methylpiperazino)-6-bromo-isothiazolo[4,3-b]pyridine (100 mg, 0.32 mmol) in dioxane (6 ml) and water (2.5 ml) was added an appropriate boronic acid (2 eq), sodium carbonate (2 eq, 68 mg) and Pd(dppf)Cl$_2$ (0.1 eq, 26 mg). The reaction mixture was heated at 95° C. overnight. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography yielding the pure title compounds The following compounds were made according to this procedure:

Example 38

3-(N-Me-piperazinyl)-6-phenyl-isothiazolo[4,3-b]pyridine

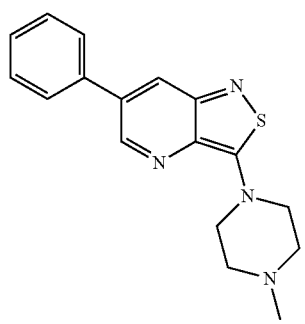 [SMILES: CN1CCN(c2snc3cc(-c4ccccc4)cnc23)CC1]

This compound was prepared using phenylboronic acid and the crude residue was purified using a mixture of methanol and dichloromethane (in a ratio of 3:100), affording the title compound in 91% yield.

$^1$H-NMR (300 MHz, CDCl$_3$): δ=2.39 (s, 3H, NCH$_3$), 2.67 (t, J=5.01 Hz, 4H, 2×NCH$_2$), 4.00 (t, J=4.99 Hz, 4H, 2×NCH$_2$), 7.47 (m, 3H, arom H), 7.65 (m, 2H, arom H), 7.89 (d, J=1.83 Hz, 1H, arom H), 8.63 (d, J=1.83 Hz, 1H, arom H) ppm.

Example 39

3-(N-Me-piperazinyl)-6-(3-pyridyl)-isothiazolo[4,3-b]pyridine

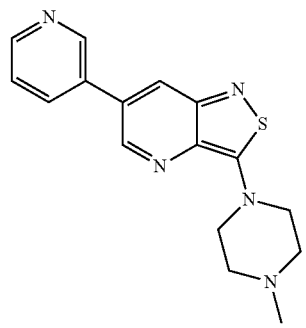 [SMILES: CN1CCN(c2snc3cc(-c4cccnc4)cnc23)CC1]

This compound was prepared using 3-pyridylboronic acid and the crude residue was purified using a mixture of methanol and dichloromethane (in a ratio of 1:20), affording the title compound in 83% yield.

$^1$H-NMR (300 MHz, DMSO-$d_6$): δ=2.26 (s, 3H, NCH$_3$), 2.55 (t, J=4.85 Hz, 4H, 2×NCH$_2$), 3.92 (t, J=4.80 Hz, 4H, 2×NCH$_2$), 7.54 (m, 1H, arom H), 8.12 (d, J=1.98 Hz, 1H, arom H), 8.24 (d, J=7.86 Hz, 1H, arom H), 8.65 (d, J=4.74 Hz, 1H, arom H), 8.75 (d, J=1.92 Hz, 1H, arom H), 9.04 (d, J=1.95 Hz, 1H, arom H) ppm.

Example 40

3-(N-Me-piperazinyl)-6-(3,4-dimethoxyphenyl)-isothiazolo[4,3-b]pyridine

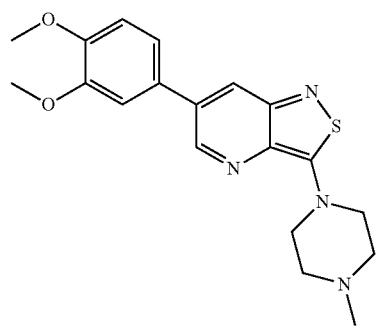 [SMILES: COc1ccc(-c2cnc3c(N4CCN(C)CC4)snc3c2)cc1OC]

This compound was prepared using 3,4-dimethoxyphenyl boronic acid and the crude residue was purified using a mixture of methanol and dichloromethane (in a ratio of 1:30), affording the title compound in 66% yield.

$^1$H-NMR (300 MHz, DMSO-$d_6$): δ=2.27 (s, 3H, NCH$_3$), 2.56 (t, J=4.91 Hz, 4H, 2×NCH$_2$), 3.82 (s, 3H, OCH$_3$), 3.88 (s, 3H, OCH$_3$), 3.92 (t, J=4.88 Hz, 4H, 2×NCH$_2$), 7.09 (d, J=8.43 Hz, 1H, arom H), 7.38 (m, 2H, arom H), 7.99 (d, J=1.98 Hz, 1H, arom H), 8.75 (d, J=2.01 Hz, 1H, arom H) ppm.

Example 41

3-(N-Me-piperazinyl)-6-(3-thienyl)-isothiazolo[4,3-b]pyridine

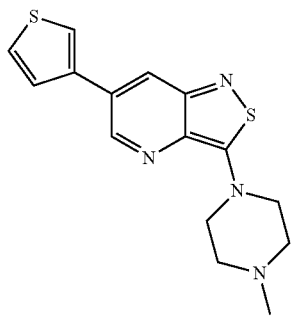 [SMILES: CN1CCN(c2snc3cc(-c4ccsc4)cnc23)CC1]

This compound was prepared using 3-thienylboronic acid and the crude residue was purified using a mixture of methanol and dichloromethane (in a ratio of 3:100), affording the title compound in 84% yield.

$^1$H-NMR (300 MHz, DMSO-d$_6$): δ=2.26 (s, 3H, NCH$_3$), 2.55 (t, J=4.91 Hz, 4H, 2×NCH$_2$), 3.91 (t, J=4.88 Hz, 4H, 2×NCH$_2$), 7.72 (m, 2H, arom H), 8.07 (br s, 1H, arom H), 8.07 (br s, 1H, arom H), 8.19 (br s, 1H, arom H), 8.83 (d, J=1.98 Hz, 1H, arom H) ppm.

Example 42

3-(N-Me-piperazinyl)-6-(4-fluorophenyl)-isothiazolo[4,3-b]pyridine

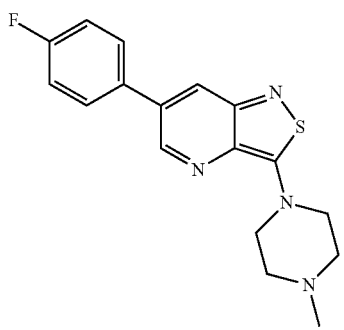 [SMILES: CN1CCN(c2snc3cc(-c4ccc(F)cc4)cnc23)CC1]

This compound was prepared using 4-fluorophenylboronic acid and the crude residue was purified using a mixture of methanol and dichloromethane (in a ratio of 3:100), affording the title compound in 96% yield.

$^1$H-NMR (300 MHz, CDCl$_3$): δ=2.40 (s, 3H, NCH$_3$), 2.68 (br s, 4H, 2×NCH$_2$), 4.00 (br s, 4H, 2×NCH$_2$), 7.19 (t, J=8.61 Hz, 1H, arom H), 7.59 (m, 2H, arom H), 7.84 (d, J=2.01 Hz, 1H, arom H), 8.57 (d, J=2.01 Hz, arom H) ppm.

Examples 43-54

Synthesis of 3-morpholino-6-aryl-isothiazolo[4,3-b]pyridines

General Procedure

To a solution of 3-morpholino-6-bromo-isothiazolo[4,3-b]pyridine in DME (2 ml) was added an appropriate boronic acid (2 eq or 1.5 eq) and potassium carbonate (2 eq, 1M solution in H$_2$O). Mixture was degassed and Pd(PPh$_3$)$_4$ (10 mol %) was added. The reaction was heated at 80° C. After the completion of reaction, solvents were evaporated. The crude residue was purified by silicagel flash chromatography, yielding the pure title compounds.

The following compounds were made according to this procedure:

Example 43

4-(6-(Thiophen-2-yl)isothiazolo[4,3-b]pyridin-3-yl)morpholine

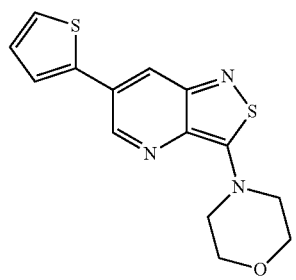 [SMILES: c1csc(-c2cnc3c(N4CCOCC4)snc3c2)c1]

This compound was prepared from 3-morpholino-6-bromo-isothiazolo[4,3-b]pyridine (90 mg, 0.3 mmol) using thiophene-2-boronic acid (0.6 mmol, 76 mg), 1M K$_2$CO$_3$ (0.6 ml) and Pd(PPh$_3$)$_4$ (0.03 mmol, 34 mg). Product was purified using a mixture of cyclohexane/ethyl acetate in a ratio of 1:1, affording the title compound in 78% yield (71 mg, 0.234 mmol).

1H-NMR (300 MHz, CDCl$_3$): δ=3.96 (m, 8H, 4×CH$_2$), 7.16 (dd, J=3.66 Hz, J=5.10 Hz, 1H, arom H), 7.42 (dd, J=1.08 Hz, J=5.10 Hz, 1H, arom H), 7.49 (dd, J=3.66 Hz, J=1.08 Hz, 1H, arom H), 7.93 (d, J=2.07 Hz, 1H, arom H), 8.69 (d, J=2.10 Hz, 1H, arom H) ppm.

Example 44

4-(6-(2,5-Dimethoxyphenyl)isothiazolo[4,3-b]pyridin-3-yl)morpholine

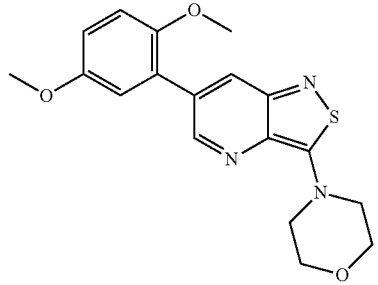 [SMILES: COc1ccc(OC)c(-c2cnc3c(N4CCOCC4)snc3c2)c1]

This compound was prepared from 3-morpholino-6-bromo-isothiazolo[4,3-b]pyridine (90 mg, 0.3 mmol) using 2,5-dimethoxyphenylboronic acid (0.6 mmol, 109 mg), 1M K$_2$CO$_3$ (0.6 ml) and Pd(PPh$_3$)$_4$ (0.03 mmol, 34 mg). Product was purified using a mixture of cyclohexane/ethyl acetate in a ratio of 2:1, affording the title compound in 69% yield (74 mg, 0.207 mmol).

1H-NMR (300 MHz, CDCl$_3$): δ=3.80 (s, 3H, OCH$_3$), 3.84 (s, 3H, OCH$_3$), 3.97 (m, 8H, 4×CH$_2$), 6.95-6.97 (m, 3H, arom H), 7.89 (d, J=1.95 Hz, 1H, arom H), 8.58 (d, J=1.92 Hz, 1H, arom H) ppm.

Example 45

4-(6-(2,4-Dimethoxyphenyl)isothiazolo[4,3-b]pyridin-3-yl)morpholine

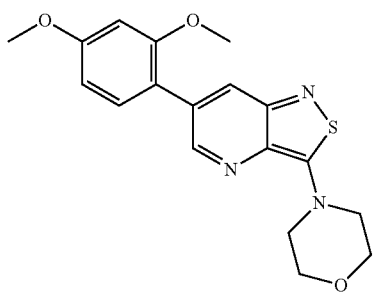 [SMILES: COc1ccc(-c2cnc3c(N4CCOCC4)snc3c2)c(OC)c1]

This compound was prepared from 3-morpholino-6-bromo-isothiazolo[4,3-b]pyridine (90 mg, 0.3 mmol) using 2,4-dimethoxyphenylboronic acid (0.6 mmol, 109 mg), 1M K$_2$CO$_3$ (0.6 ml) and Pd(PPh$_3$)$_4$ (0.03 mmol, 34 mg). Product was purified using a mixture of cyclohexane/ethyl acetate in a ratio of 2:1, affording the title compound in 73% yield (79 mg, 0.221 mmol).

1H-NMR (300 MHz, CDCl$_3$): δ=3.84 (s, 3H, OCH$_3$), 3.88 (s, 3H, OCH$_3$), 3.96 (m, 8H, 4×CH$_2$), 6.60-6.64 (m, 2H, arom H), 7.33 (d, J=8.19 Hz, 1H, arom H), 7.84 (d, J=1.95 Hz, 1H, arom H), 8.57 (d, J=1.92 Hz, 1H, arom H) ppm.

Example 46

Methyl 2-methoxy-4-(3-morpholinoisothiazolo[4,3-b]pyridin-6-yl)benzoate

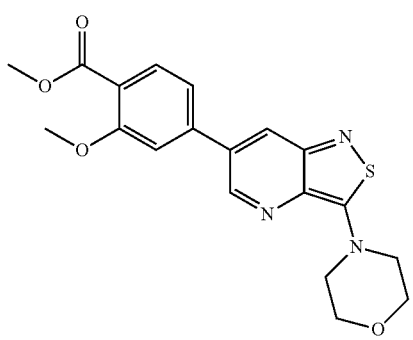 [SMILES: COC(=O)c1ccc(-c2cnc3c(N4CCOCC4)snc3c2)cc1OC]

This compound was prepared from 3-morpholino-6-bromo-isothiazolo[4,3-b]pyridine (60 mg, 0.2 mmol) using 4-methoxycarbonyl-3-methoxyphenylboronic acid (0.4 mmol, 84 mg), 1M K$_2$CO$_3$ (0.4 ml) and Pd(PPh$_3$)$_4$ (0.02 mmol, 23 mg). Product was purified using a mixture of cyclohexane/ethyl acetate in a ratio of 2:1, affording the title compound in 66% yield (51 mg, 0.132 mmol).

1H-NMR (300 MHz, CDCl$_3$): δ=3.96 (s, 3H, OCH$_3$), 3.98 (m, 8H, 4×CH$_2$), 4.00 (s, 3H, OCH$_3$(ester)), 7.23 (d, J=1.38 Hz, 1H, arom H), 7.27 (m, 1H, arom H), 7.93 (s, 1H, arom H), 7.96 (d, J=1.83 Hz, 1H, arom H), 8.64 (d, J=2.07 Hz, 1H, arom H) ppm.

Example 47

2-Methoxy-4-(3-morpholinoisothiazolo[4,3-b]pyridin-6-yl)phenyl acetate

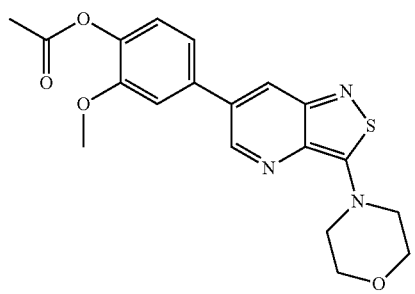 [SMILES: COc1cc(-c2cnc3c(N4CCOCC4)snc3c2)ccc1OC(C)=O]

This compound was prepared from 3-morpholino-6-bromo-isothiazolo[4,3-b]pyridine (60 mg, 0.2 mmol) using 4-acetoxy-3-methoxyphenylboronic acid pinacol ester (0.4 mmol, 116 mg), 1M K$_2$CO$_3$ (0.4 ml) and Pd(PPh$_3$)$_4$ (0.02 mmol, 23 mg). Product was purified using a mixture of cyclohexane/ethyl acetate in a ratio of 2:1, affording the title compound in 58% yield (45 mg, 0.116 mmol).

1H-NMR (300 MHz, CDCl$_3$): δ=2.37 (s, 3H, CH$_3$ (acetyl)), 3.93 (s, 3H, OCH$_3$), 3.98 (m, 8H, 4×CH$_2$), 7.16-7.28 (m, 3H, arom H), 7.91 (d, J=1.98 Hz, 1H, arom H), 8.53 (d, J=2.01 Hz, 1H, arom H) ppm.

Example 48

4-(6-(3,5-Dimethoxyphenyl)isothiazolo[4,3-b]pyridin-3-yl)morpholine

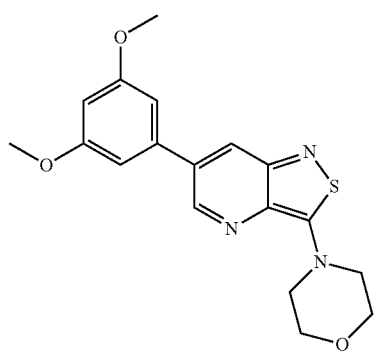 [SMILES: COc1cc(OC)cc(-c2cnc3c(N4CCOCC4)snc3c2)c1]

This compound was prepared from 3-morpholino-6-bromo-isothiazolo[4,3-b]pyridine (60 mg, 0.2 mmol) using 3,5-dimethoxyphenylboronic acid (0.4 mmol, 72 mg), 1M K$_2$CO$_3$ (0.4 ml) and Pd(PPh$_3$)$_4$ (0.02 mmol, 23 mg). Product was purified using a mixture of cyclohexane/ethyl acetate in a ratio of 2:1, affording the title compound in 70% yield (50 mg, 0.140 mmol).

1H-NMR (300 MHz, CDCl$_3$): δ=3.88 (s, 6H, 2×OCH$_3$), 3.98 (m, 8H, 4×CH$_2$), 6.55 (m, 1H, arom H), 6.80 (d, J=2.19

Hz, 2H, arom H), 7.92 (d, J=1.98 Hz, 1H, arom H), 8.63 (d, J=2.01 Hz, 1H, arom H) ppm.

Example 49

4-(6-(3,4,5-Trimethoxyphenyl)isothiazolo[4,3-b]pyridin-3-yl)morpholine

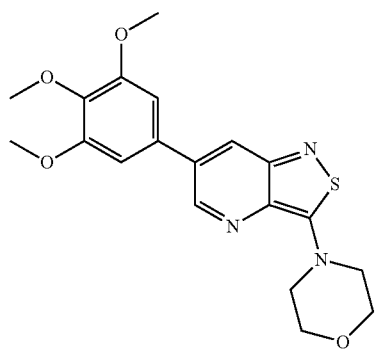 [SMILES: COc1cc(-c2cnc3c(N4CCOCC4)snc3c2)cc(OC)c1OC]

This compound was prepared from 3-morpholino-6-bromo-isothiazolo[4,3-b]pyridine (76 mg, 0.25 mmol) using 3,4,5-trimethoxyphenylboronic acid (0.5 mmol, 107 mg), 1M $K_2CO_3$ (0.5 ml) and $Pd(PPh_3)_4$ (0.025 mmol, 29 mg). Product was purified using a mixture of cyclohexane/ethyl acetate in a ratio of 2:1, affording the title compound in 56% yield (54 mg, 0.141 mmol).

1H-NMR (300 MHz, CDCl$_3$): δ=3.91 (s, 3H, OCH$_3$), 3.94 (s, 6H, 2×OCH$_3$), 3.96 (m, 8H, 4×CH$_2$), 6.85 (s, 2H, arom H), 7.88 (d, J=1.86 Hz, 1H, arom H), 8.62 (d, J=1.89 Hz, 1H, arom H) ppm.

Example 50

2-Methoxy-4-(3-morpholinoisothiazolo[4,3-b]pyridin-6-yl)aniline

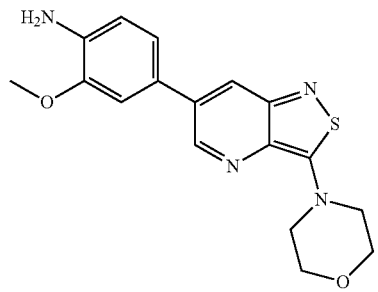 [SMILES: COc1cc(-c2cnc3c(N4CCOCC4)snc3c2)ccc1N]

This compound was prepared from 3-morpholino-6-bromo-isothiazolo[4,3-b]pyridine (60 mg, 0.2 mmol) using 4-amino-3-methoxyphenylboronic acid pinacol ester (0.4 mmol, 99 mg), 1M $K_2CO_3$ (0.4 ml) and $Pd(PPh_3)_4$ (0.02 mmol, 23 mg). Product was purified using a mixture of cyclohexane/ethyl acetate in a ratio of 2:1, affording the title compound in 58% yield (40 mg, 0.116 mmol).

1H-NMR (300 MHz, CDCl$_3$): δ=3.95 (s, 3H, OCH$_3$), 3.97 (m, 8H, 4×CH$_2$), 6.82 (d, J=7.98 Hz, 1H, arom H), 7.10 (m, 2H, arom H), 7.85 (d, J=2.04 Hz, 1H, arom H), 8.66 (d, J=2.07 Hz, 1H, arom H) ppm.

Example 51

4-(6-(Benzo[d][1,3]dioxol-5-yl)isothiazolo[4,3-b]pyridin-3-yl)morpholine

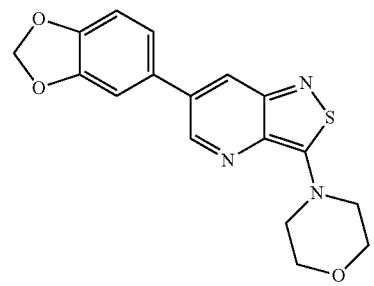 [SMILES: c1cc2c(cc1-c1cnc3c(N4CCOCC4)snc3c1)OCO2]

This compound was prepared from 3-morpholino-6-bromo-isothiazolo[4,3-b]pyridine (60 mg, 0.2 mmol) using 3,4-methylenedioxyphenylboronic acid (0.4 mmol, 66 mg), 1M $K_2CO_3$ (0.4 ml) and $Pd(PPh_3)_4$ (0.02 mmol, 23 mg). Product was purified using a mixture of cyclohexane/ethyl acetate in a ratio of 2:1, affording the title compound in 64% yield (43 mg, 0.128 mmol).

1H-NMR (300 MHz, CDCl$_3$): δ=3.96 (m, 8H, 4×CH$_2$), 6.05 (s, 2H, CH$_2$), 6.94 (d, J=7.86 Hz, 1H, arom H), 7.15 (m, 2H, arom H), 7.83 (d, J=2.01 Hz, 1H, arom H), 8.58 (d, J=2.04 Hz, 1H, arom H) ppm.

Example 52

4-(6-(Furan-3-yl)isothiazolo[4,3-b]pyridin-3-yl)morpholine

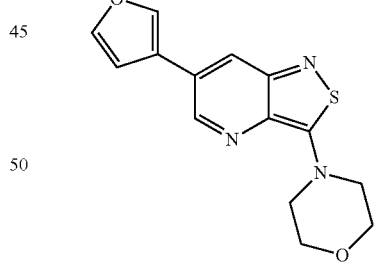

This compound was prepared from 3-morpholino-6-bromo-isothiazolo[4,3-b]pyridine (40 mg, 0.133 mmol) using furan-3-boronic acid (0.2 mmol, 23 mg), 1M $K_2CO_3$ (0.26 ml) and $Pd(PPh_3)_4$ (0.013 mmol, 36 mg). Product was purified using a mixture of cyclohexane/ethyl acetate in a ratio of 2:1, affording the title compound in 51% yield (19 mg, 0.067 mmol).

1H-NMR (300 MHz, CDCl$_3$): δ=3.96 (m, 8H, 4×CH$_2$), 6.79 (s, 1H, arom H), 7.56 (m, 1H, arom H), 7.81 (d, J=2.01 Hz, 1H, arom H), 7.90 (s, 1H, arom H), 8.56 (d, J=2.01 Hz, 1H, arom H) ppm.

Example 53

Methyl 4-(3-morpholinoisothiazolo[4,3-b]pyridin-6-yl)benzoate

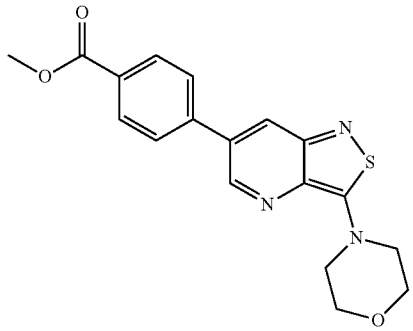 [SMILES: COC(=O)c1ccc(-c2cnc3c(N4CCOCC4)snc3c2)cc1]

This compound was prepared from 3-morpholino-6-bromo-isothiazolo[4,3-b]pyridine (40 mg, 0.133 mmol) using 3-ethoxycarbonylphenylboronic acid (0.2 mmol, 36 mg), 1M $K_2CO_3$ (0.26 ml) and $Pd(PPh_3)_4$ (0.013 mmol, 36 mg). Product was purified using a mixture of cyclohexane/ethyl acetate in a ratio of 3:1, affording the title compound in 67% yield (32 mg, 0.090 mmol).

1H-NMR (300 MHz, $CDCl_3$): δ=3.99 (m, 11H, 4×$CH_2$, $OCH_3$), 7.74 (d, J=8.1 Hz, 2H, arom H), 7.98 (d, J=1.47 Hz, 1H, arom H), 8.19 (d, J=8.1 Hz, 2H, arom H), 8.65 (d, J=1.46 Hz, 1H, arom H) ppm.

Example 54

N-Methyl-4-(3-morpholinoisothiazolo[4,3-b]pyridin-6-yl)benzamide

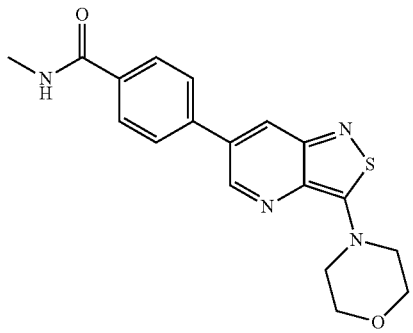

This compound was prepared from 3-morpholino-6-bromo-isothiazolo[4,3-b]pyridine (40 mg, 0.133 mmol) using 4-(N-methylaminocarbonyl)phenylboronic acid (0.2 mmol, 35 mg), 1M $K_2CO_3$ (0.26 ml) and $Pd(PPh_3)_4$ (0.013 mmol, 36 mg). Product was purified using a mixture of cyclohexane/ethyl acetate in a ratio of 2:3, affording the title compound in 31% yield (14 mg, 0.041 mmol).

1H-NMR (300 MHz, $CDCl_3$): δ=3.09 (d, J=4.71 Hz, 3H, $NCH_3$), 3.99 (m, 8H, 4×$CH_2$), 7.73 (d, J=8.25 Hz, 1H, arom H), 7.90 (d, J=8.22 Hz, 2H, arom H), 8.00 (d, J=1.89 Hz, 1H, arom H), 8.64 (d, J=1.86 Hz, 1H, arom H) ppm.

Examples 55-56

Synthesis of 3-substituted-6-bromo-isothiazolo[4,3-b]pyridines

General Procedure

These compounds were prepared according to the general procedure described for examples 11-13.

The following compounds were prepared according to this procedure:

Example 55

6-bromo-3-(piperidin-1-yl)isothiazolo[4,3-b]pyridine

This compound was made using piperidine as nucleophile and the crude residue was purified using a mixture of cyclohexane and ethylacetate (in a ratio of 4:1) as mobile phase, affording the title compound in 85% yield.

$^1$H-NMR (300 MHz, $CDCl_3$) δ=1.75 (m, 6H), 3.9 (t, J=5.22, 4H, 2×$NCH_2$), 7.89 (d, J=2.1 Hz, 1H, arom H), 8.25 (d, J=2.07 Hz, 1H, arom H) ppm.

Example 56

6-bromo-3-thiomorpholinoisothiazolo[4,3-b]pyridine

This compound was made using thiomorpholine as nucleophile and the crude residue was purified using a mixture of cyclohexane and ethylacetate (in a ratio of 4:1) as mobile phase, affording the title compound in 86% yield $^1$H-NMR (300 MHz, $CDCl_3$) δ=2.83 (m, 4H, 2×$SCH_2$), 4.82 (m, 4H, 2×$NCH_2$), 7.91 (d, J=2.07 Hz, 1H, arom H), 8.27 (d, J=2.04 Hz, 1H, arom H) ppm.

Examples 57-58

Synthesis of 3-substituted-6-aryl-isothiazolo[4,3-b]pyridines

General Procedure

These compounds were prepared according to the methods described for the synthesis of examples 23-27.

The following compounds were made according to this procedure:

Example 57

6-(3,4-dimethoxyphenyl)-3-(piperidin-1-yl)isothiazolo[4,3-b]pyridine

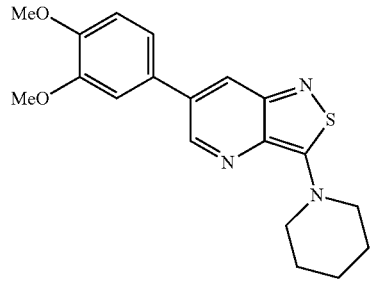 [SMILES: COc1ccc(-c2cnc3c(N4CCCCC4)snc3c2)cc1OC]

This compound was prepared using 3,4-dimethoxyphenylboronic acid and was purified using a mixture of cyclohexane and ethylacetate (in a ratio of 1:1), affording the title compound in 45% yield.

$^1$H-NMR (300 MHz, CDCl$_3$) δ=1.74 (m, 6H), 3.88 (br s, 4H, 2×NCH$_2$) 3.91 (d, J=6.78, 6H, 2×OCH$_3$), 6.95 (d, J=8.31 Hz, 1H, arom H), 7.13 (s, 1H, arom H), 7.19 (dd, J=1.93; 8.26 Hz, 1H arom H), 7.80 (d, J=1.98 Hz, 1H, arom H), 8.57 (d, J=1.98 Hz, 1H, arom H) ppm. $^{13}$C-NMR (300 MHz, CDCl$_3$), 24.0 (CH$_2$), 25.3 (CH$_2$), 51.8 (CH$_2$), 56.0 (CH$_3$), 56.0 (CH$_3$), 110.4 (CH), 111.7 (CH), 119.8 (CH), 124.6 (CH), 130.5 (C$_q$), 133.7 (C$_q$), 135.3 (C$_q$), 143.5 (CH), 149.5 (C$_q$), 156.3 (C$_q$), 173.5 (C$_q$) ppm.

Example 58

6-(3,4-dimethoxyphenyl)-3-thiomorpholinoisothiazolo[4,3-b]pyridine

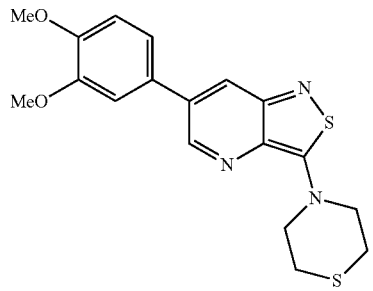 [SMILES: COc1ccc(-c2cnc3c(N4CCSCC4)snc3c2)cc1OC]

This compound was prepared using 3,4-dimethoxyphenylboronic acid and was purified using a mixture of cyclohexane and ethylacetate (in a ratio of 1:1), affording the title compound in 52% yield.

$^1$H-NMR (300 MHz, CDCl$_3$) δ=2.85 (m, 4H, 2×SCH$_2$), 3.92 (d, J=6.15, 6H, 2×OCH$_3$), 4.29 (m, 4H, 2×NCH$_2$), 6.96 (d, J=8.25 Hz, 1H, arom H), 7.13 (s, 1H, arom H), 7.20 (dd, J=1.45; 8.26 Hz, 1H, arom H), 7.81 (d, J=1.95 Hz, 1H, arom H), 8.58 (d, J=1.41 Hz, 1H, arom H) ppm. $^{13}$C-NMR (300 MHz, CDCl$_3$), 26.5 (CH$_2$), 53.2 (CH$_2$), 56.0 (CH$_3$), 56.0 (CH$_3$), 110.4 (CH), 111.7 (CH), 119.9 (CH), 124.8 (CH), 130.3 (C$_q$), 133.7 (C$_q$), 135.6 (C$_q$), 144.2 (CH), 149.5 (C$_q$), 149.6 (C$_q$), 156.6 (C$_q$), 172.3 (C$_q$) ppm.

Example 59

Synthesis of 3-bromo-6-(2-bromo-4,5-dimethoxyphenyl)isothiazolo[4,3-b]pyridine

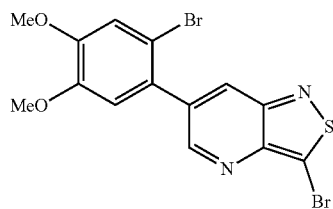 [SMILES: COc1cc(Br)c(-c2cnc3c(Br)snc3c2)cc1OC]

To a solution of 3-amino-6-(3,4-dimethoxyphenyl)-isothiazolo[4,3-b]pyridine (1 g, 3.5 mmol) in HBr (20 ml) at 0° C., was added portionwise sodium nitrite (2 eq, 0.48 g). After 30 minutes, CuBr (2 eq, 1.33 g) was added. The reaction mixture was stirred for two hours, at 0° C. and then heated to 80° C. for the other two hours. The mixture was neutralized with solid potassium carbonate and extracted with ethyl acetate (2×50 ml). The combined organic phases were dried over MgSO$_4$ and evaporated in vacuo. The crude residue was purified by silica gel flash chromatography, the mobile phase being a mixture of cyclohexane and ethylacetate (in a ratio of 9:1), yielding the pure title compound (0.93 g, 62%).

$^1$H-NMR (300 MHz, CDCl$_3$) δ=3.88 (s, 3H, OCH$_3$), 3.93 (s, 3H, OCH$_3$), 6.87 (s, 1H, arom H), 7.16 (s, 1H, arom H), 8.05 (t, J=0.96 Hz, 1H, arom H), 8.92 (t, J=0.95 Hz, 1H, arom H) ppm. $^{13}$C-NMR (300 MHz, CDCl$_3$), 56.3 (CH$_3$), 56.5 (CH$_3$), 113.0 (C$_q$), 113.9 (CH), 116.2 (CH), 129.0 (CH), 129.8 (C$_q$), 135.8 (C$_q$), 137.1 (C$_q$), 145.5 (C$_q$), 149.0 (C$_q$), 150.2 (C$_q$), 154.2 (CH), 154.7 (C$_q$) ppm.

Example 60

Synthesis of 4-(6-(2-bromo-4,5-dimethoxyphenyl)isothiazolo[4,3-b]pyridin-3-yl)morpholine

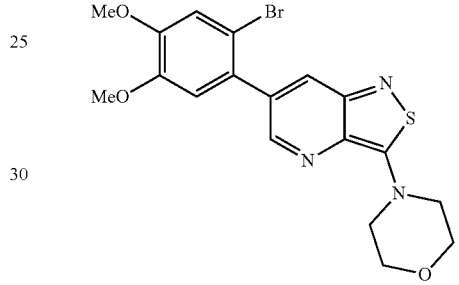

To a solution of 3-bromo-6-(2-bromo-4,5-dimethoxyphenyl)isothiazolo[4,3-b]pyridine (100 mg, 0.221 mmol) in ethanol (10 ml) was added morpholine (3 eq, 57.7 mg). The reaction was stirred overnight at 75° C. The solvent was evaporated in vacuo and the crude residue was purified by silicagel flash chromatography, the mobile phase being a mixture of cyclohexane and ethylacetate (in a ratio of 1:1), affording the title compound in 80% yield.

$^1$H-NMR (300 MHz, CDCl$_3$) δ=3.87 (s, 3H, OCH$_3$), 3.92 (s, 3H, OCH$_3$), 3.95 (s, 8H), 6.86 (s, 1H, arom H), 7.14 (s, 1H, arom H), 7.75 (d, J=1.98 Hz, 1H, arom H), 8.43 (t, J=1.95 Hz, 1H, arom H). $^{13}$C-NMR (300 MHz, CDCl$_3$), 50.5 (CH2), 56.3 (CH$_3$), 56.4 (CH$_3$), 66.3 (CH2), 112.9 (C$_q$), 113.9 (CH), 116.1 (CH), 128.5 (CH), 130.9 (C$_q$), 134.1 (C$_q$), 136.3 (C$_q$), 146.0 (CH), 148.8 (C$_q$), 149.8 (C$_q$), 155.8 (C$_q$), 173.5 (C$_q$) ppm.

Examples 61-63

Synthesis of 3-morpholino-6-aryl-isothiazolo[4,3-b]pyridines

General Procedure

To a solution of 3-morpholino-6-bromo-isothiazolo[4,3-b]pyridine (0.2 mmol, 60 mg) in DME (2 ml) was added an appropriate boronic acid (1.5 eq, 0.3 mmol) and potassium carbonate (2 eq, 400 μl, 1M solution in H$_2$O). The mixture was degassed and Pd(PPh$_3$)$_4$ (10 mol %, 0.02 mmol, 23 mg) was added. The reaction was heated at 80° C. After completion of the reaction, solvents were evaporated. The crude residue was purified by silicagel flash chromatography, yielding the pure title compounds.

The following compounds were made according to this procedure:

Example 61

4-(6-(3-methoxyphenyl)isothiazolo[4,3-b]pyridin-3-yl)morpholine

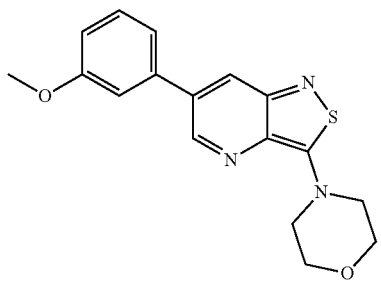 [SMILES: COc1cccc(-c2cnc3c(N4CCOCC4)snc3c2)c1]

This compound was prepared from 3-morpholino-6-bromo-isothiazolo[4,3-b]pyridine using 3-methoxyphenyl-boronic acid (46 mg). Product was purified using a mixture of cyclohexane/ethyl acetate in a ratio of 3:1, affording the title compound in 66% yield (43 mg, 0.133 mmol).

$^1$H-NMR (300 MHz, CDCl$_3$): δ=3.89 (s, 3H, OCH$_3$), 3.98 (m, 8H, 4×CH$_2$), 6.98 (dd, 1H, J=1.80 Hz, J=7.53 Hz arom H), 7.18-7.27 (m, 2H, arom H), 7.43 (t, 1H, J=7.98 Hz, arom H), 7.93 (bs, 1H, arom H), 8.65 (d, J=2.04 Hz, 1H, arom H) ppm.

Example 62

2-methoxy-5-(3-morpholinoisothiazolo[4,3-b]pyridin-6-yl)phenyl acetate

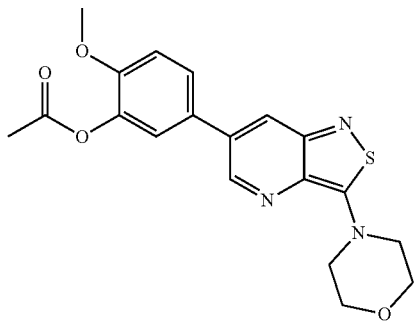 [SMILES: COc1ccc(-c2cnc3c(N4CCOCC4)snc3c2)cc1OC(C)=O]

This compound was prepared from 3-morpholino-6-bromo-isothiazolo[4,3-b]pyridine using 3-acetoxy-4-methoxyphenylboronic acid pinacol ester (87.6 mg). The crude product was purified using a mixture of cyclohexane/ethyl acetate in a ratio of 5:1, affording the title compound in 56% yield (43 mg, 0.112 mmol).

$^1$H-NMR (300 MHz, CDCl$_3$): δ=2.37 (s, 3H, CH$_3$ (acetyl)) 3.91 (s, 3H, OCH$_3$), 3.96 (m, 8H, 4×CH$_2$), 7.11 (d, J=8.58 Hz, 1H, arom H), 7.37 (d, J=2.25 Hz, 1H, arom H), 7.84 (dd, J=2.25 Hz, J=8.49 Hz, 1H, arom H), 7.87 (bs, 1H, arom H), 8.60 (d, J=2.01 Hz, 1H, arom H) ppm.

Example 63

4-(6-(4-methoxyphenyl)isothiazolo[4,3-b]pyridin-3-yl)morpholine

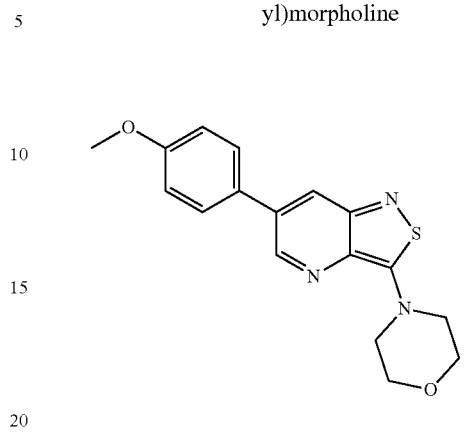

This compound was prepared from 3-morpholino-6-bromo-isothiazolo[4,3-b]pyridine using 4-methoxyphenyl-boronic acid (45.5 mg). The crude product was purified using a mixture of cyclohexane/ethyl acetate in a ratio of 5:1, affording the title compound in 73% yield (48 mg, 0.146 mmol).

$^1$H-NMR (300 MHz, CDCl$_3$): δ=3.75 (s, 3H, OCH$_3$), 3.97 (m, 8H, 4×CH$_2$), 7.06 (d, J=8.82 Hz, 2H, arom H), 7.63 (d, J=8.82 Hz, 2H, arom H), 7.87 (d, J=2.10 Hz, 1H, arom H), 8.64 (d, J=2.07 Hz, 1H, arom H) ppm.

Example 64

2-methoxy-4-(3-morpholinoisothiazolo[4,3-b]pyridin-6-yl)phenol

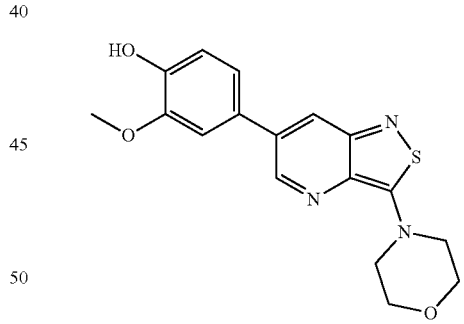

This compound was prepared from 3-morpholino-6-bromo-isothiazolo[4,3-b]pyridine (60 mg, 0.2 mmol) using methoxy-4-(4,4,5,5-tetramethyl-1,3,2-dioxaborolan-2-yl)phenol (0.3 mmol, 75 mg), 1M K$_2$CO$_3$ (0.4 ml) and Pd(PPh$_3$)$_4$ (0.02 mmol, 23 mg). Product was purified using a mixture of cyclohexane/ethyl acetate in a ratio of 3:2, affording the title compound in 44% yield (30 mg, 0.087 mmol).

1H-NMR (300 MHz, CDCl$_3$): δ=3.97 (m, 11H, 4×CH$_2$, CH$_3$), 5.93 (s, 1H, OH), 7.04 (d, J=8.16 Hz, 1H, arom H), 7.14 (d, J=1.95 Hz, 1H, arom H), 7.19 (dd, J=2.04 Hz, J=8.16 Hz, 1H, arom H), 7.87 (d, J=2.07 Hz, 1H, arom H), 8.64 (d, J=2.07 Hz, 1H, arom H) ppm.

Examples 65-76

Synthesis of 3-substituted 6-(3,4-dimethoxyphenyl)isothiazolo[4,3-b]pyridines General Procedure To a solution of 3,6-di-bromo-isothiazolo[4,3-b]pyridine in ethanol was added an appropriate nitrogen nucleophile (3 eq). The reaction was stirred at 75° C. After the reaction was finished, the solvent was evaporated in vacuo and the crude residue was purified by silicagel flash chromatography yielding the 3-substituted-6-bromo-isothiazolo[4,3-b]pyridine derivatives.

To a solution of this 3-substituted-6-bromo-isothiazolo[4,3-b]pyridine in DME (2 ml) was added an appropriate boronic acid (1.5 eq) and potassium carbonate (2 eq, 1M solution in $H_2O$). The reaction mixture was degassed and $Pd(PPh_3)_4$ (10 mol %) was added. The reaction was heated at 80° C. After the completion of the reaction, solvents were evaporated. The crude residue was purified by silicagel flash chromatography, yielding the pure title compounds.

The following compounds were made according to this procedure:

Example 65

1-(6-(3,4-dimethoxyphenyl)isothiazolo[4,3-b]pyridin-3-yl)piperidin-4-one

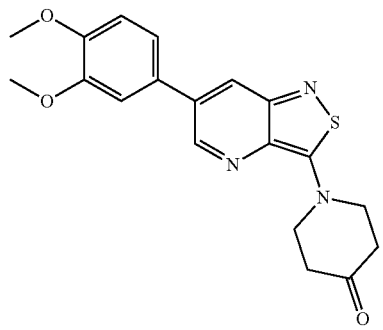 [SMILES: COc1ccc(-c2cnc3c(N4CCC(=O)CC4)snc3c2)cc1OC]

1-(6-bromoisothiazolo[4,3-b]pyridin-3-yl)piperidin-4-one was prepared from 3,6-di-bromo-isothiazolo[4,3-b]pyridine (146 mg, 0.5 mmol), piperidine-4-one hydrochloride (230 mg, 1.5 mmol) and DIPEA (0.256 ml, 1.50 mmol) in EtOH (10 ml). The crude product was purified using a mixture of cyclohexane/ethyl acetate in a ratio of 95:5, affording 1-(6-bromoisothiazolo[4,3-b]pyridin-3-yl)piperidin-4-one in 24% yield (38 mg, 0.121 mmol).

The title compound was prepared from 1-(6-bromoisothiazolo[4,3-b]pyridin-3-yl)piperidin-4-one (38 mg, 0.121 mmol) using 3,4-dimethoxyphenylboronic acid (0.181 mmol, 33 mg), 1M $K_2CO_3$ (0.24 ml) and $Pd(PPh_3)_4$ (0.012 mmol, 14 mg). The product was purified using a mixture of cyclohexane/ethyl acetate in a ratio of 1:1, affording the title compound in 53% yield (24.1 mg, 0.065 mmol).

$^1$H-NMR (300 MHz, $CDCl_3$): δ=2.76 (t, 4H, 2×$CH_2$), 3.97 (s, 3H, $OCH_3$), 3.98 (s, 3H, $OCH_3$), 4.39 (m, 4H, 2×$CH_2$), 7.03 (d, J=8.34 Hz, 1H, arom H), 7.19 (d, J=1.92 Hz, 1H, arom H), 7.25 (dd, J=2.04 Hz, 1H, arom H), 7.92 (d, J=1.92 Hz, 1H, arom H), 8.69 (d, J=1.98 Hz, 1H, arom H) ppm.

Example 66

1-(6-(3,4-dimethoxyphenyl)isothiazolo[4,3-b]pyridin-3-yl)piperidin-4-ol

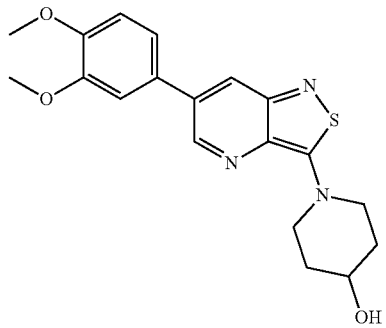 [SMILES: COc1ccc(-c2cnc3c(N4CCC(O)CC4)snc3c2)cc1OC]

1-(6-bromoisothiazolo[4,3-b]pyridin-3-yl)piperidin-4-ol was prepared from 3,6-di-bromo-isothiazolo[4,3-b]pyridine (0.5 mmol, 146 mg) and 4-hydroxypiperidine (1.5 mmol, 151 mg) in EtOH (10 ml). The crude product was purified using a mixture of DCM/MeOH in a ratio of 95:5, affording 1-(6-bromoisothiazolo[4,3-b]pyridin-3-yl)piperidin-4-ol in 82% yield (130 mg, 0.414 mmol).

The title compound was prepared from 1-(6-bromoisothiazolo[4,3-b]pyridin-3-yl)piperidin-4-ol (63 mg, 0.2 mmol) using 3,4-dimethoxyphenylboronic acid (0.3 mmol, 54.5 mg), 1M $K_2CO_3$ (0.4 ml) and $Pd(PPh_3)_4$ (0.02 mmol, 23 mg). The product was purified using a mixture of cyclohexane/ethyl acetate in a ratio of 1:1, affording the title compound in 57% yield (42.8 mg, 0.115 mmol).

1H-NMR (300 MHz, $CDCl_3$): δ=1.83 (m, 2H, $CH_2$), 2.09 (m, 2H, $CH_2$), 3.70 (m, 2H, $CH_2$), 3.94 (s, 3H, $OCH_3$), 3.96 (s, 3H, $OCH_3$), 4.06 (m, 1H, CH), 4.35 (m, 2H, $CH_2$), 6.97 (d, J=8.34 Hz, 1H, arom H), 7.17 (d, J=2.07 Hz, 1H, arom H), 7.24 (dd, J=8.28, J=2.07 Hz, 1H, arom H), 7.86 (d, J=2.01 Hz, 1H, arom H), 8.61 (d, J=2.04 Hz, 1H, arom H) ppm.

Example 67

5-(6-(3,4-dimethoxyphenyl)isothiazolo[4,3-b]pyridin-3-ylamino)pentan-1-ol

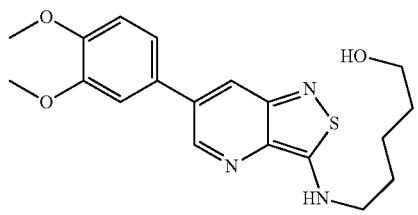 [SMILES: COc1ccc(-c2cnc3c(NCCCCCO)snc3c2)cc1OC]

5-(6-bromoisothiazolo[4,3-b]pyridin-3-ylamino)pentan-1-ol was prepared from 3,6-di-bromo-isothiazolo[4,3-b]pyridine (0.5 mmol, 146 mg) and 5-aminopentan-1-ol (1.5 mmol, 155 mg) in EtOH (10 ml). The product was purified using a mixture of DCM/MeOH in a ratio of 95:5, affording 5-(6-bromoisothiazolo[4,3-b]pyridin-3-ylamino)pentan-1-ol in 74% yield (118 mg, 0.373 mmol).

The title compound was prepared from 5-(6-bromoisothiazolo[4,3-b]pyridin-3-ylamino)pentan-1-ol (63 mg, 0.2 mmol) using 3,4-dimethoxyphenylboronic acid (0.3 mmol, 54.5 mg), 1M K$_2$CO$_3$ (0.4 ml) and Pd(PPh$_3$)$_4$ (0.02 mmol, 23 mg). The crude product was purified using a mixture of cyclohexane/ethyl acetate in a ratio of 1:3, affording the title compound in 12% yield (8.9 mg, 0.024 mmol).

1H-NMR (300 MHz, CDCl$_3$): δ=1.66 (m, 4H, 2×CH$_2$), 1.86 (m, 2H, CH2), 3.42 (m, 2H, CH$_2$), 3.74 (m, 2H, CH$_2$), 3.96 (s, 3H, OCH$_3$), 3.98 (s, 3H, OCH$_3$), 6.36 (t, 1H, NH), 7.02 (d, J=8.34 Hz, 1H, arom H), 7.16 (d, J=2.07 Hz, 1H, arom H), 7.24 (dd, J=8.25, J=2.07 Hz, 1H, arom H), 7.88 (d, J=1.92 Hz, 1H, arom H), 8.57 (d, J=1.95 Hz, 1H, arom H) ppm.

Example 68

1-(6-(3,4-dimethoxyphenyl)isothiazolo[4,3-b]pyridin-3-yl)piperidin-3-ol

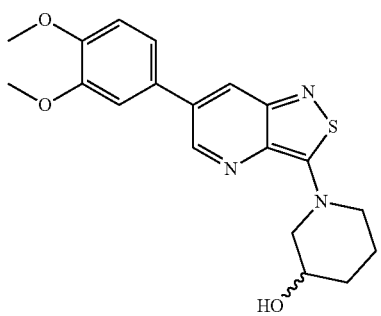 [SMILES: COc1ccc(-c2cnc3c(N4CCCC(O)C4)snc3c2)cc1OC]

1-(6-bromoisothiazolo[4,3-b]pyridin-3-yl)piperidin-3-ol was prepared from 3,6-di-bromo-isothiazolo[4,3-b]pyridine (0.5 mmol, 146 mg) and 3-hydroxypiperidine (1.5 mmol, 151 mg) in EtOH (10 ml). The product was purified using a mixture of cyclohexane/ethyl acetate in a ratio of 1:1, affording 1-(6-bromoisothiazolo[4,3-b]pyridin-3-yl)piperidin-3-ol in 89% yield (140 mg, 0.144 mmol).

The title compound was prepared from 1-(6-bromoisothiazolo[4,3-b]pyridin-3-yl)piperidin-3-ol (62.8 mg, 0.2 mmol) using 3,4-dimethoxyphenylboronic acid (0.3 mmol, 54.5 mg), 1M K$_2$CO$_3$ (0.4 ml) and Pd(PPh$_3$)$_4$ (0.02 mmol, 23 mg). The product was purified using a mixture of cyclohexane/ethyl acetate in a ratio of 1:1, affording the title compound in 24% yield (18 mg, 0.048 mmol).

$^1$H-NMR (300 MHz, CDCl$_3$): δ=1.80-2.1 (m, 5H, CH, 2×CH$_2$), 3.64 (m, 1H, CH), 3.95 (s, 3H, OCH$_3$), 3.97 (s, 3H, OCH$_3$), 4.13 (m, 3H, CH, CH$_2$), 6.99 (d, J=8.34 Hz, 1H, arom H), 7.17 (d, J=2.04 Hz, 1H, arom H), 7.24 (dd, J=8.28, J=2.07 Hz, 1H, arom H), 7.85 (d, J=2.01 Hz, 1H, arom H), 8.61 (d, J=2.04 Hz, 1H, arom H) ppm.

Example 69

6-(3,4-dimethoxyphenyl)-N-(tetrahydro-2H-pyran-4-yl)isothiazolo[4,3-b]pyridin-3-amine

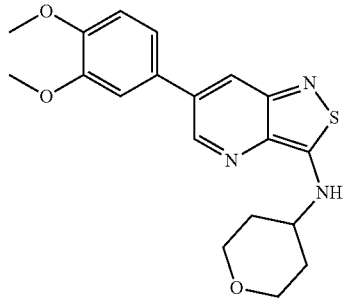 [SMILES: COc1ccc(-c2cnc3c(NC4CCOCC4)snc3c2)cc1OC]

6-bromo-N-(tetrahydro-2H-pyran-4-yl)isothiazolo[4,3-b]pyridin-3-amine was prepared from 3,6-di-bromo-isothiazolo[4,3-b]pyridine (0.5 mmol, 146 mg) and 4-aminopyrane (0.151 ml, 1.5 mmol) in EtOH (10 ml). The product was purified using a mixture of cyclohexane/ethyl acetate in a ratio of 3:1, affording 6-bromo-N-(tetrahydro-2H-pyran-4-yl)isothiazolo[4,3-b]pyridin-3-amine in 40% yield (64 mg, 0.203 mmol).

The title compound was prepared from 6-bromo-N-(tetrahydro-2H-pyran-4-yl)isothiazolo[4,3-b]pyridin-3-amine (64 mg, 0.203 mmol) using 3,4-dimethoxyphenylboronic acid (0.304 mmol, 55.3 mg), 1M K$_2$CO$_3$ (0.406 ml) and Pd(PPh$_3$)$_4$ (0.02 mmol, 23 mg). Product was purified using a mixture of cyclohexane/ethyl acetate in a ratio of 1:1, affording the title compound in 16% yield (5.5 mg, 0.015 mmol).

$^1$H-NMR (300 MHz, CDCl$_3$): δ=1.72 (m, 2H, 2×CH$_2$), 2.25 (m, 2H, CH$_2$), 3.54 (m, 3H, CH, CH$_2$) 3.95 (s, 3H, OCH$_3$), 3.97 (s, 3H, OCH$_3$), 4.12 (m, 2H, CH$_2$), 6.26 (d, J=7.59, 1H, NH) 6.99 (d, J=8.34 Hz, 1H, arom H), 7.16 (d, J=2.04 Hz, 1H, arom H), 7.24 (dd, J=8.28, J=2.04 Hz, 1H, arom H), 7.89 (d, J=1.89 Hz, 1H, arom H), 8.59 (d, J=1.89 Hz, 1H, arom H) ppm.

Example 70

2,2'-(6-(3,4-dimethoxyphenyl)isothiazolo[4,3-b]pyridin-3-ylazanediyl)diethanol

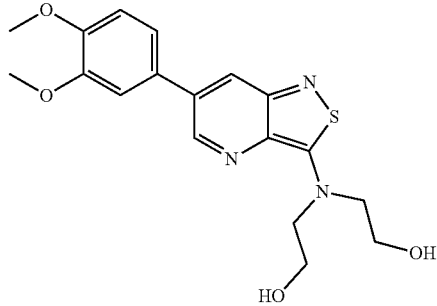 [SMILES: COc1ccc(-c2cnc3c(N(CCO)CCO)snc3c2)cc1OC]

2,2'-(6-bromoisothiazolo[4,3-b]pyridin-3-ylazanediyl)diethanol was prepared from 3,6-di-bromo-isothiazolo[4,3-b]pyridine (0.5 mmol, 146 mg) and diethanolamine (0.145 ml, 1.5 mmol) in EtOH (10 ml). The product was purified using a mixture of DCM/MeOH in a ratio of 95:5, affording 2,2'-(6-bromoisothiazolo[4,3-b]pyridin-3-ylazanediyl)diethanol in 81% yield (129 mg, 0.405 mmol).

The title compound was prepared from 2,2'-(6-bromoiso-thiazolo[4,3-b]pyridin-3-ylazanediyl)diethanol (63.6 mg, 0.2 mmol) using 3,4-dimethoxyphenylboronic acid (0.3 mmol, 54.5 mg), 1M K$_2$CO$_3$ (0.4 ml) and Pd(PPh$_3$)$_4$ (0.02 mmol, 23 mg). The crude product was purified using a mixture of DCM/MeOH in a ratio of 100:1, affording the title compound in 60% yield (45 mg, 0.12 mmol).

$^1$H-NMR (300 MHz, CDCl$_3$): δ=3.96 (s, 3H, OCH$_3$), 3.98 (s, 3H, OCH$_3$), 4.05 (m, 8H, 4×CH$_2$), 4.20 (m, 2H, 2×OH), 7.02 (d, J=8.31 Hz, 1H, arom H), 7.15 (d, J=2.04 Hz, 1H, arom H), 7.24 (dd, J=8.28, J=2.13 Hz, 1H, arom H), 7.86 (d, J=2.04 Hz, 1H, arom H), 8.56 (d, J=2.04 Hz, 1H, arom H) ppm.

Example 71

3-(6-(3,4-dimethoxyphenyl)isothiazolo[4,3-b]pyridin-3-ylamino)propane-1,2-diol

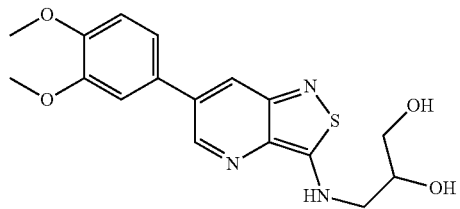 [SMILES: COc1ccc(-c2cnc3c(NCC(O)CO)snc3c2)cc1OC]

3-(6-bromoisothiazolo[4,3-b]pyridin-3-ylamino)propane-1,2-diol was prepared from 3,6-di-bromo-isothiazolo[4,3-b]pyridine (0.5 mmol, 146 mg) and 3-amino-1,2-propanediol (137 mg, 1.5 mmol) in EtOH (10 ml). The product was purified using a mixture of DCM/MeOH in a ratio of 95:5, affording 3-(6-bromoisothiazolo[4,3-b]pyridin-3-ylamino)propane-1,2-diol in 65% yield (99 mg, 0.325 mmol).

The title compound was prepared from 3-(6-bromoisothiazolo[4,3-b]pyridin-3-ylamino)propane-1,2-diol (60.8 mg, 0.2 mmol) using 3,4-dimethoxyphenylboronic acid (0.3 mmol, 54.5 mg), 1M K$_2$CO$_3$ (0.4 ml) and Pd(PPh$_3$)$_4$ (0.02 mmol, 23 mg). Product was purified using a mixture of DCM/MeOH in a ratio of 100:1, affording the title compound in 66% yield (48 mg, 0.132 mmol).

$^1$H-NMR (300 MHz, DMSO): δ=3.30-3.50 (m, 4H, 2×CH2), 3.82 (s, 3H, OCH$_3$), 3.84 (m, 1H, CH), 3.88 (s, 3H, OCH$_3$), 4.74 (t, 1H, OH), 5.05 (d, 1H, OH), 7.07 (d, J=8.76 Hz, 1H, arom H), 7.35 (m, 3H, arom H), 7.92 (s, 1H, arom H), 8.27 (t, 1H, NH), 8.64 (s, 1H, arom H) ppm.

Example 72 ethyl 4-(6-(3,4-dimethoxyphenyl)isothiazolo[4,3-b]pyridin-3-ylamino)piperidine-1-carboxylate

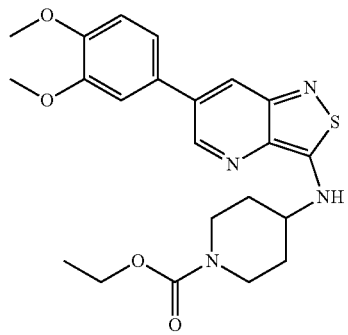 [SMILES: CCOC(=O)N1CCC(Nc2snc3cc(-c4ccc(OC)c(OC)c4)cnc23)CC1]

ethyl 4-(6-bromoisothiazolo[4,3-b]pyridin-3-ylamino)piperidine-1-carboxylate was prepared from 3,6-di-bromo-isothiazolo[4,3-b]pyridine (1.0 mmol, 293 mg) and ethyl 4-amino-1-piperidinecarboxylate (0.53 ml, 3.0 mmol) in EtOH (10 ml). The product was purified using a mixture of cyclohexane/ethylacetate in a ratio of 4:1, affording the ethyl 4-(6-bromoisothiazolo[4,3-b]pyridin-3-ylamino)piperidine-1-carboxylate in 42% yield (162 mg, 0.420 mmol).

The title compound was prepared from ethyl 4-(6-bromoisothiazolo[4,3-b]pyridin-3-ylamino)piperidine-1-carboxylate (162 mg, 0.42 mmol) using 3,4-dimethoxyphenylboronic acid (0.63 mmol, 114 mg), 1M K$_2$CO$_3$ (0.84 ml) and Pd(PPh$_3$)$_4$ (0.042 mmol, 48 mg). Product was purified using a mixture of cyclohexane/ethylacetate in a ratio of 1:1, affording the title compound in 13% yield (25 mg, 0.056 mmol).

$^1$H-NMR (300 MHz, CDCl$_3$): δ=1.27 (t, J=7.05 Hz, J=7.17 Hz, 1H, CH$_3$), 1.65 (m, 2H, CH$_2$), 2.23 (m, 1H, CH$_2$), 3.02 (m, 2H, CH$_2$), 3.47 (m, 1H, CH), 3.93 (s, 3H, OCH$_3$), 3.95 (s, 3H, OCH$_3$), 4.19 (m, 4H, CH$_2$, OCH$_2$) 6.34 (d, J=7.53 Hz, 1H, NH), 6.99 (d, J=8.28 Hz, 1H, arom H), 7.14 (d, 1H, J=1.83 Hz, arom H), 7.20 (dd, J=8.25, J=1.77 Hz, 1H, arom H), 7.86 (d, J=1.53 Hz, 1H, arom H), 8.64 (d, J=1.53 Hz, 1H, arom H) ppm.

Example 73

6-(3,4-dimethoxyphenyl)-3-(pyrrolidin-1-yl)isothiazolo[4,3-b]pyridine

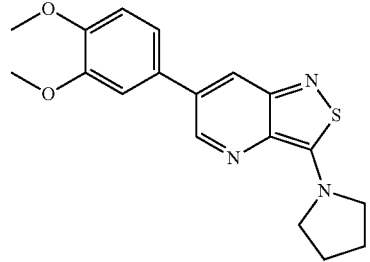 [SMILES: COc1ccc(-c2cnc3c(N4CCCC4)snc3c2)cc1OC]

6-bromo-3-(pyrrolidin-1-yl)isothiazolo[4,3-b]pyridine was prepared from 3,6-di-bromo-isothiazolo[4,3-b]pyridine (0.5 mmol, 146 mg) and pyrrolidine (0.04 ml, 1.5 mmol) in EtOH (10 ml). Product was purified using a mixture of cyclohexane/ethylacetate in a ratio of 4:1, affording the 6-bromo-3-(pyrrolidin-1-yl)isothiazolo[4,3-b]pyridine in 90% yield (128 mg, 0.450 mmol).

The title compound was prepared from 6-bromo-3-(pyrrolidin-1-yl)isothiazolo[4,3-b]pyridine (71 mg, 0.25 mmol) using 3,4-dimethoxyphenylboronic acid (0.375 mmol, 68 mg), 1M K$_2$CO$_3$ (0.50 ml) and Pd(PPh$_3$)$_4$ (0.025 mmol, 29 mg). The product was purified using a mixture of cyclohexane/ethylacetate in a ratio of 3:2, affording the title compound in 63% yield (54 mg, 0.158 mmol).

$^1$H-NMR (300 MHz, CDCl$_3$): δ=2.17 (m, 4H, 2×CH$_2$), 3.87 (m, 4H, 2×CH$_2$), 3.96 (s, 3H, OCH$_3$), 3.98 (s, 3H, OCH$_3$), 7.00 (d, J=8.28 Hz, 1H, arom H), 7.18 (d, 1H, J=2.01 Hz, arom H), 7.26 (dd, J=8.52, J=2.28 Hz, 1H, arom H), 7.82 (d, J=1.95 Hz, 1H, arom H), 8.58 (d, J=1.95 Hz, 1H, arom H) ppm.

Example 74

6-(3,4-dimethoxyphenyl)-N-phenethylisothiazolo[4,3-b]pyridin-3-amine

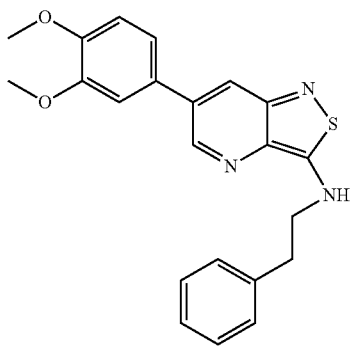 [SMILES: COc1ccc(-c2cnc3c(NCCc4ccccc4)snc3c2)cc1OC]

6-bromo-N-phenethylisothiazolo[4,3-b]pyridin-3-amine was prepared from 3,6-di-bromo-isothiazolo[4,3-b]pyridine (0.5 mmol, 146 mg) and phenethylamine (0.188 ml, 1.5 mmol) in EtOH (10 ml). The product was purified using a mixture of cyclohexane/ethylacetate in a ratio of 4:1, affording the 6-bromo-N-phenethylisothiazolo[4,3-b]pyridin-3-amine in 77% yield (130 mg, 0.389 mmol).

The title compound was prepared from 6-bromo-N-phenethylisothiazolo[4,3-b]pyridin-3-amine (130 mg, 0.389 mmol) using 3,4-dimethoxyphenylboronic acid (0.583 mmol, 106 mg), 1M $K_2CO_3$ (0.78 ml) and $Pd(PPh_3)_4$ (0.038 mmol, 45 mg). Product was purified using a mixture of cyclohexane/ethylacetate in a ratio of 9:1, affording the title compound in 25% yield (39 mg, 0.099 mmol).

$^1$H-NMR (300 MHz, CDCl$_3$): δ=3.11 (t, J=7.05 Hz, 1H, CH$_2$), 3.66 (m, 2H, CH$_2$), 3.95 (s, 3H, OCH$_3$), 3.97 (s, 3H, OCH$_3$), 6.36 (m, 1H, NH) 7.01 (d, J=8.31 Hz, 1H, arom H), 7.15 (d, J=1.89 Hz, 1H, arom H), 7.21-7.37 (m, 6H, arom H), 7.87 (d, J=1.86 Hz, 1H, arom H), 8.66 (d, J=1.83 Hz, 1H, arom H) ppm.

Example 75

6-(3,4-dimethoxyphenyl)-N-(2-methoxyethyl)isothiazolo[4,3-b]pyridin-3-amine

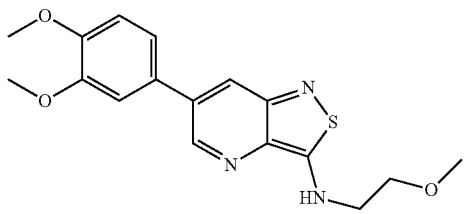

6-bromo-N-(2-methoxyethyl)isothiazolo[4,3-b]pyridin-3-amine was prepared from 3,6-di-bromo-isothiazolo[4,3-b]pyridine (0.5 mmol, 146 mg) and 2-methoxyethylamine (0.13 ml, 1.5 mmol) in EtOH (10 ml). The product was purified using a mixture of cyclohexane/ethylacetate in a ratio of 4:1, affording the 6-bromo-N-(2-methoxyethyl)isothiazolo[4,3-b]pyridin-3-amine in 83% yield (120 mg, 0.416 mmol).

The title compound was prepared from 6-bromo-N-(2-methoxyethyl)isothiazolo[4,3-b]pyridin-3-amine (57 mg, 0.2 mmol) using 3,4-dimethoxyphenylboronic acid (0.3 mmol, 54.5 mg), 1M $K_2CO_3$ (0.40 ml) and $Pd(PPh_3)_4$ (0.02 mmol, 23 mg). Product was purified using a mixture of cyclohexane/ethylacetate in a ratio of 1:1, affording the title compound in 22% yield (15 mg, 0.043 mmol).

$^1$H-NMR (300 MHz, CDCl$_3$): δ=3.40 (s, 3H, OCH$_3$), 3.55 (m, 2H, CH$_2$), 3.58 (m, 2H, CH$_2$), 3.95 (s, 3H, OCH$_3$), 3.97 (s, 3H, OCH$_3$), 6.53 (m, 1H, NH), 6.99 (d, J=8.31 Hz, 1H, arom H), 7.15 (d, 1H, J=1.98 Hz, arom H), 7.21 (dd, J=1.98 Hz, J=8.22 Hz, 1H, arom H), 7.87 (d, J=1.80 Hz, 1H, arom H), 8.60 (d, J=1.80 Hz, 1H, arom H) ppm.

Example 76

N-(cyclopropylmethyl)-6-(3,4-dimethoxyphenyl)isothiazolo[4,3-b]pyridin-3-amine

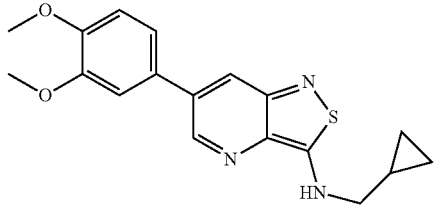 [SMILES: COc1ccc(-c2cnc3c(NCC4CC4)snc3c2)cc1OC]

6-bromo-N-(cyclopropylmethyl)isothiazolo[4,3-b]pyridin-3-amine was prepared from 3,6-di-bromo-isothiazolo[4,3-b]pyridine (0.5 mmol, 146 mg) and aminomethylcyclopropane (0.086 ml, 3.0 mmol) in EtOH (10 ml). The product was purified using a mixture of cyclohexane/ethylacetate in a ratio of 9:1, affording the 6-bromo-N-(cyclopropylmethyl)isothiazolo[4,3-b]pyridin-3-amine in 84% yield (120 mg, 0.422 mmol). The title compound was prepared from 6-bromo-N-(cyclopropylmethyl)isothiazolo[4,3-b]pyridin-3-amine (85 mg, 0.3 mmol) using 3,4-dimethoxyphenylboronic acid (0.45 mmol, 82 mg), 1M $K_2CO_3$ (0.60 ml) and $Pd(PPh_3)_4$ (0.03 mmol, 34 mg). Product was purified using a mixture of cyclohexane/ethylacetate in a ratio of 4:1, affording the title compound in 73% yield (75 mg, 0.210 mmol).

$^1$H-NMR (300 MHz, CDCl$_3$): δ=0.67 (q, 2H, CH$_2$), 0.69 (q, 2H, CH$_2$), 1.25 (m, 1H, CH), 3.24 (q, 2H, NCH$_2$), 3.96 (s, 3H, OCH$_3$), 3.98 (s, 3H, OCH$_3$), 6.36 (t, 1H, NH), 7.02 (d, J=8.34 Hz, 1H, arom H), 7.17 (d, J=2.07 Hz, 1H, arom H), 7.25 (dd, J=8.28, J=2.1 Hz, 1H, arom H), 7.88 (d, J=1.92 Hz, 1H, arom H), 8.59 (d, J=1.95 Hz, 1H, arom H) ppm.

Example 77

Synthesis of 3-bromo-6-(4,5-dimethoxyphenyl)isothiazolo[4,3-b]pyridine

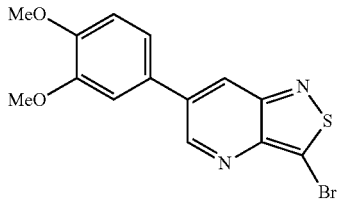 [SMILES: COc1ccc(-c2cnc3c(Br)snc3c2)cc1OC]

To a solution of 3-amino-6-(3,4-dimethoxyphenyl)-isothiazolo[4,3-b]pyridine (1 g, 3.5 mmol) in H Br (20 ml) at 0° C., was added portionwise sodium nitrite (2 eq, 0.48 g). After 30 minutes, CuBr (2 eq, 1.33 g) was added. The reaction mixture was stirred for two hours, at 0° C. and then stirred at room temperature overnight. The mixture was neutralized with solid potassium carbonate and extracted with ethyl acetate (2×50 ml). The combined organic phases were dried over MgSO$_4$ and evaporated in vacuo. The crude residue was purified by silica gel flash chromatography, the mobile phase being a mixture of cyclohexane and ethylacetate (in a ratio of 9:1), yielding the pure title compound (0.38 g, 31%).

$^1$H-NMR (300 MHz, CDCl$_3$) δ=3.96 (s, 3H, OCH$_3$), 3.99 (s, 3H, OCH$_3$), 7.02 (d, J=8.3 Hz, 1H, arom H), 7.20 (s, 1H, arom H), 7.28 (dd, J=2.2; 8.3 Hz, 1H arom H), 8.21 (dd, J=1.0; 2.0 Hz, 1H, arom H), 9.08 (d, J=1.9 Hz, 1H, arom H) ppm.

Examples 78-81

Synthesis of 3-substituted 6-(3,4-dimethoxyphenyl)-isothiazolo[4,3-b]pyridines

General Procedure

To a solution of 3-bromo-6-(4,5-dimethoxyphenyl)isothiazolo[4,3-b]pyridine (100 mg, 0.285 mmol) in ethanol (10 ml) was added an appropriate amine (3 eq, 0.855 mmol). The reaction was stirred overnight at 75° C. The solvent was evaporated in vacuo and the crude residue was purified by silicagel flash chromatography yielding the pure title compounds.

The following compounds were made according to this procedure:

Example 78

6-(3,4-dimethoxyphenyl)-N,N-dimethylisothiazolo[4,3-b]pyridin-3-amine

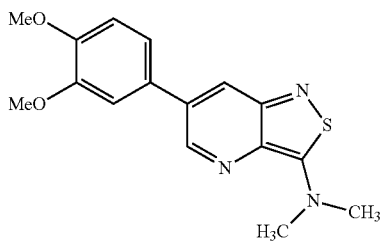 [SMILES: COc1ccc(-c2cnc3c(N(C)C)snc3c2)cc1OC]

This compound was prepared using dimethylamine and was purified using a mixture of cyclohexane and ethylacetate (in a ratio of 1:1), affording the title compound in 98% yield.

$^1$H-NMR (300 MHz, CDCl$_3$) δ=3.49 (s, 6H, 2×CH$_3$), 3.94 (s, 3H, OCH$_3$), 3.99 (s, 3H, OCH$_3$), 6.97 (d, J=8.3 Hz, 1H, arom H), 7.15 (s, 1H, arom H), 7.21 (dd, J=2.1; 8.3 Hz, 1H arom H), 7.80 (d, J=2.0 Hz, 1H, arom H), 8.56 (d, J=2.0 Hz, 1H, arom H) ppm.

Example 79

6-(3,4-dimethoxyphenyl)-N,N-diethylisothiazolo[4,3-b]pyridin-3-amine

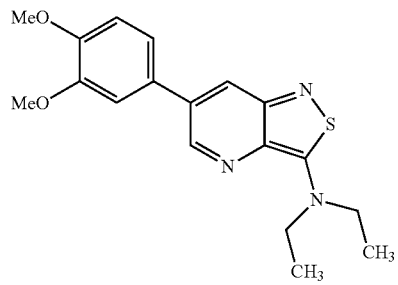 [SMILES: CCN(CC)c1snc2cc(-c3ccc(OC)c(OC)c3)cnc12]

This compound was prepared using diethylamine and was purified using a mixture of cyclohexane and ethylacetate (in a ratio of 1:1), affording the title compound in 80% yield.

$^1$H-NMR (300 MHz, CDCl$_3$) δ=1.34 (t, J=7.1 Hz, 6H, 2×CH$_3$), 3.93 (m, 10H, 2×OCH$_3$, 2×NCH$_2$), 6.97 (d, J=8.3 Hz, 1H, arom H), 7.16 (s, 1H, arom H), 7.22 (dd, J=2.1; 8.3 Hz, 1H arom H), 7.79 (d, J=2.1 Hz, 1H, arom H), 8.56 (d, J=2.1 Hz, 1H, arom H) ppm.

Example 80

(2R,6S)-4-(6-(3,4-dimethoxyphenyl)isothiazolo[4,3-b]pyridin-3-yl)-2,6-dimethylmorpholine

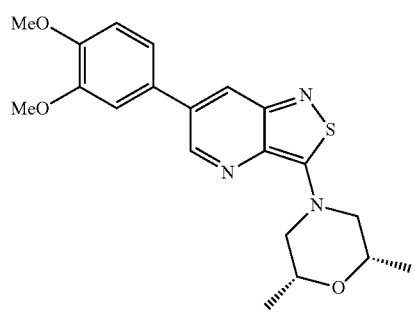 [SMILES: COc1ccc(-c2cnc3c(N4C[C@@H](C)O[C@@H](C)C4)snc3c2)cc1OC]

This compound was prepared using cis-2,6-dimethylmorpholine and was purified using a mixture of cyclohexane and ethylacetate (in a ratio of 1:1), affording the title compound in 78% yield.

$^1$H-NMR (300 MHz, CDCl$_3$) δ=1.31 (d, J=6.3 Hz, 6H, 2×CH$_3$), 2.90 (t, J=11.7 Hz, 2H, 2×NCH), 3.94 (m, 8H, 2×OCH$_3$, 2×OCH), 4.50, (d, J=12.6 Hz, 2×NCH), 6.98 (d, J=8.4 Hz, 1H, arom H), 7.15 (d, J=2.1 Hz, 1H, arom H), 7.23 (dd, J=2.2; 8.3 Hz, 1H arom H), 7.84 (d, J=2.1 Hz, 1H, arom H), 8.62 (d, J=2.1 Hz, 1H, arom H) ppm.

Example 81

8-(6-(3,4-dimethoxyphenyl)isothiazolo[4,3-b]pyridin-3-yl)-1,4-dioxa-8-azaspiro[4.5]decane

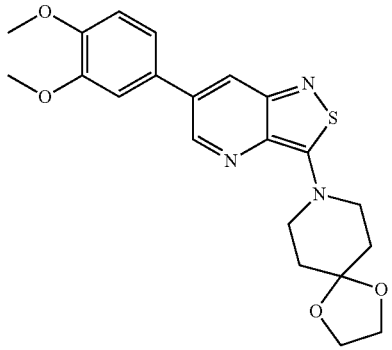 [SMILES: COc1ccc(-c2cnc3c(N4CCC5(CC4)OCCO5)snc3c2)cc1OC]

This compound was prepared using 1,4-dioxa-8-aza-spiro[4.5]decane and was purified using a mixture of cyclohexane and ethylacetate (in a ratio of 1:1), affording the title compound in 65% yield.

$^{1}$H-NMR (300 MHz, CDCl$_{3}$) δ=1.95 (t, J=5.9 Hz, 4H, 2×CCH$_{2}$), 3.93 (s, 3H, OCH$_{3}$), 3.95 (s, 3H, OCH$_{3}$), 4.01, (s, 4H, 2×OCH$_{2}$), 4.08 (t, J=5.8 Hz, 4H, 2×NCH$_{2}$), 6.98 (d, J=8.3 Hz, 1H, arom H), 7.15 (d, J=2.0 Hz, 1H, arom H), 7.22 (dd, J=2.1; 8.3 Hz, 1H arom H), 7.83 (d, J=2.0 Hz, 1H, arom H), 8.61 (d, J=1.9 Hz, 1H, arom H) ppm.

Examples 82-85

Synthesis of 3-aryl-6-(4,5-dimethoxyphenyl)isothiazolo[4,3-b]pyridines

General Procedure

To a solution of 3-bromo-6-(4,5-dimethoxyphenyl)isothiazolo[4,3-b]pyridine (25 mg, 0.067 mmol) in a mixture of dioxane (10 ml) and water (1.5 ml) was added an appropriate arylboronic acid (2 eq), sodium carbonate (2 eq, 16.3 mg) and Pd(dppf)Cl$_{2}$ (0.1 eq, 5.4 mg) The reaction mixture was stirred overnight at 100° C. The reaction mixture was cooled down to room temperature and the reaction was partioned between ethylacetate (30 ml) and brine (15 ml). The aqueous phase was then extracted with ethyl acetate (30 ml). The combined organic phases were dried over MgSO$_{4}$ and evaporated in vacuo. The residue was purified by flash chromatography on silicagel yielding the pure title compounds.

The following compounds were made according to this procedure:

Example 82

6-(3,4-dimethoxyphenyl)-3-phenylisothiazolo[4,3-b]pyridine

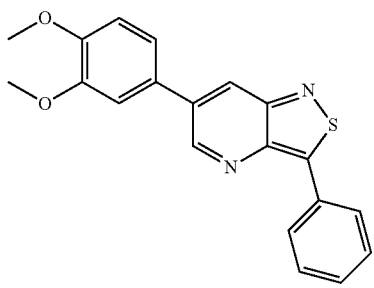 [SMILES: COc1ccc(-c2cnc3c(-c4ccccc4)snc3c2)cc1OC]

This compound was prepared using phenylboronic acid and was purified using a mixture of cyclohexane and ethylacetate (in a ratio of 1:1), affording the title compound in 52% yield.

$^{1}$H-NMR (300 MHz, CDCl$_{3}$) δ=3.96 (s, 3H, OCH$_{3}$), 3.99 (s, 3H, OCH$_{3}$), 7.03 (d, J=8.3 Hz, 1H, arom H), 7.21 (d, J=2.4 Hz, 1H, arom H), 7.30 (dd, J=2.1; 8.3 Hz, 1H, arom H), 7.53 (m, 3H, arom H), 8.19 (m, 3H, arom H), 9.11 (d, J=2.1 Hz, 1H, arom H) ppm.

Example 83

6-(3,4-dimethoxyphenyl)-3-(pyridin-4-yl)isothiazolo[4,3-b]pyridine

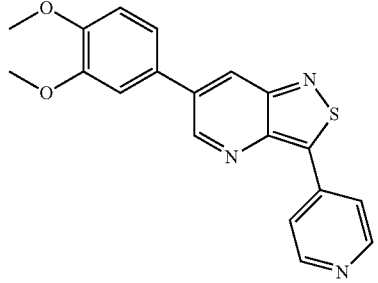 [SMILES: COc1ccc(-c2cnc3c(-c4ccncc4)snc3c2)cc1OC]

This compound was prepared using pyridine-4-boronic acid and was purified using a mixture of cyclohexane and ethylacetate (in a ratio of 1:1), affording the title compound in 48% yield.

$^{1}$H-NMR (300 MHz, CDCl$_{3}$) δ=3.97 (s, 3H, OCH$_{3}$), 3.99 (s, 3H, OCH$_{3}$), 7.03 (d, J=8.3 Hz, 1H, arom H), 7.21 (d, J=2.0 Hz, 1H, arom H), 7.30 (dd, J=1.9; 8.3 Hz, 1H, arom H), 8.13 (d, J=6.0 Hz, 2H, arom H), 8.21 (d, J=1.9 Hz, 1H, arom H), 8.80 (d, J=5.6 Hz, 1H, arom H), 9.16 (d, J=1.9 Hz, 1H, arom H) ppm.

Example 84

6-(3,4-dimethoxyphenyl)-3-(thiophen-3-yl)isothiazolo[4,3-b]pyridine

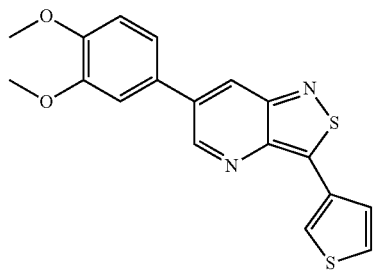 [SMILES: COc1ccc(-c2cnc3c(-c4ccsc4)snc3c2)cc1OC]

This compound was prepared using 3-thienylboric acid and was purified using a mixture of cyclohexane and ethylacetate (in a ratio of 1:1), affording the title compound in 56% yield.

$^{1}$H-NMR (300 MHz, CDCl$_{3}$) δ=3.96 (s, 3H, OCH$_{3}$), 3.99 (s, 3H, OCH$_{3}$), 7.03 (d, J=8.3 Hz, 1H, arom H), 7.21 (d, J=2.1 Hz, 1H, arom H), 7.30 (dd, J=2.1; 8.3 Hz, 1H, arom H), 7.51 (m, 1H, arom H), 7.76 (dd, J=1.2; 5.0 Hz, 1H, arom H), 8.14 (d, J=2.1 Hz, 1H, arom H), 8.52 (t, J=1.8 Hz, 1H, arom H), 9.08 (d, J=2.1 Hz, 1H, arom H) ppm.

Example 85

6-(3,4-dimethoxyphenyl)isothiazolo[4,3-b]pyridine

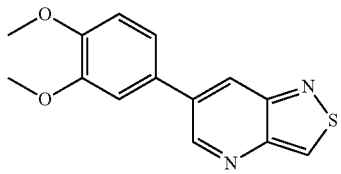 [SMILES: COc1ccc(-c2cnc3csnc3c2)cc1OC]

This compound was isolated as the major compound when using 3,5-dimethylisoxazole-4-boronic acid. The crude residue was purified using a mixture of cyclohexane and ethylacetate (in a ratio of 1:1), affording the title compound in 42% yield.
$^1$H-NMR (300 MHz, CDCl$_3$) δ=3.96 (s, 3H, OCH$_3$), 3.99 (s, 3H, OCH$_3$), 7.02 (d, J=8.3 Hz, 1H, arom H), 7.20 (d, J=2.1 Hz, 1H, arom H), 7.29 (dd, J=2.1; 8.3 Hz, 1H, arom H), 8.22 (s, 1H, arom H), 9.08 (d, J=2.0 Hz, 1H, arom H), 9.49 (s, 1H, arom H) ppm.

Examples 86-87

Synthesis of 3-bromo-6-(2-bromo-4,5-dimethoxyphenyl)isothiazolo[4,3-b]pyridines

General Procedure

To a solution of 3-bromo-6-(2-bromo-4,5-dimethoxyphenyl)isothiazolo[4,3-b]pyridine (50 mg, 0.116 mmol) in ethanol (10 ml) was added amine (3 eq, 0.349 mmol). The reaction was stirred overnight at 75° C. The solvent was evaporated in vacuo and the crude residue was purified by silicagel flash chromatography yielding the pure title compounds.
The following compounds were made according to this procedure:

Example 86

6-(2-bromo-4,5-dimethoxyphenyl)-3-(4-methylpiperidin-1-yl)isothiazolo[4,3-b]pyridine

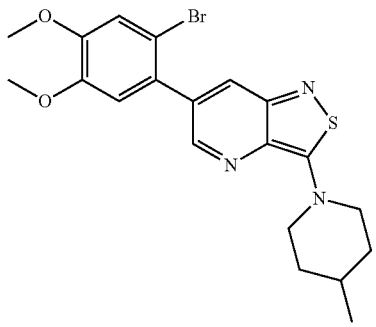 [SMILES: COc1cc(Br)c(-c2cnc3c(N4CCC(C)CC4)snc3c2)cc1OC]

This compound was prepared using 4-methylpiperidine and was purified using a mixture of cyclohexane and ethylacetate (in a ratio of 1:1), affording the title compound in 65% yield.

$^1$H-NMR (300 MHz, CDCl$_3$) δ=1.02 (d, J=6.3 Hz, 3H, CH$_3$), 1.55 (m, 3H, CHCH$_3$, 2×CHCH$_2$), 1.84 (d, J=14.6 Hz, 2H, 2×CHCH$_2$), 2.22 (t, J=12.76 Hz, 2H, 2×NCH$_2$), 3.87 (s, 3H, OCH$_3$), 3.93 (s, 3H, OCH$_3$), 4.69, (d, J=12.9 Hz, 2×NCH$_2$), 6.97 (s, 1H, arom H), 7.15 (s, 1H, arom H), 7.71 (d, J=2.0 Hz, 1H, arom H), 8.40 (d, J=2.0 Hz, 1H, arom H) ppm.

Example 87

6-(2-bromo-4,5-dimethoxyphenyl)-3-ethoxyisothiazolo[4,3-b]pyridine

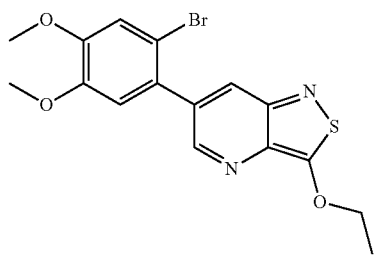 [SMILES: CCOc1snc2cc(-c3cc(OC)c(OC)cc3Br)cnc12]

This compound was isolated as the major compound when using 2-methylpiperidine as nitrogen nucleophile. The crude residue was purified using a mixture of cyclohexane and ethylacetate (in a ratio of 1:1), affording the title compound in 55% yield.
$^1$H-NMR (300 MHz, CDCl$_3$) δ=1.68 (t, J=7.0 Hz, 3H, CH$_3$), 3.88 (s, 3H, OCH$_3$), 3.92 (s, 3H, OCH$_3$), 4.54 (q, J=7.0 Hz, 2H, CH$_2$), 6.87 (s, 1H, arom H), 7.15 (s, 1H, arom H), 7.83 (d, J=1.9 Hz, 1H, arom H), 8.65 (d, J=1.8 Hz, 1H, arom H) ppm.

Example 88

GAK Binding Assay

The compounds of the invention were assayed for their GAK kinase binding affinity using the protocols, as described in Fabian, M. A. et al. A small molecule-kinase interaction map for clinical kinase inhibitors. *Nat. Biotechnol.* 23, 329-336 (2005). Table 1 summarizes the biological data.
Kinase Assays.
T7 kinase-tagged phage strains were grown in parallel in 24- or 96-well blocks in an *E. coli* host derived from the BL21 strain. *E. coli* were grown to log phase and infected with T7 phage from a frozen stock (multiplicity of infection ~0.1) and incubated with shaking at 32° C. until lysis (~90 min). The lysates were centrifuged (6,000 g) and filtered (0.2 μM) to remove cell debris. Streptavidin-coated magnetic beads were treated with biotinylated small molecule ligands for 30 min at 25° C. to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Binding reactions were assembled by combining phage lysates, liganded affinity beads and test compounds in 1×binding buffer (20% SeaBlock, 0.17×PBS, 0.05% Tween 20, 6 mM DTT). Test compounds were prepared as 1,000× stocks in DMSO and rapidly diluted into the aqueous environment (0.1% DMSO final). DMSO (0.1%) was added to control assays lacking a test compound. All reactions were carried out in polystyrene 96-well plates that had been pretreated with blocking buffer in a final volume of 0.1 ml. The assay plates were incubated at 25° C. with shaking for 1 h, long enough for binding reactions to reach equilibrium, and the affinity beads were washed four times with wash buffer (1×PBS, 0.05% Tween 20, 1 mM DTT) to remove unbound phage. After the final wash, the beads were resuspended in elution buffer (1×PBS, 0.05% Tween 20, 2 mM nonbiotinylated affinity ligand) and incubated at 25° C. with shaking for 30 min. The phage titer in the eluates was measured by standard plaque assays or by quantitative PCR.

The compounds were tested at a single concentration of 10 μM. The results of this primary screening are reported as '% Ctrl', where lower numbers indicate stronger hits (Table 1). % Ctrl is calculated using the following equation:

$$\left(\frac{\text{test compound signal} - \text{positive control signal}}{\text{negative control signal} - \text{positive control signal}}\right) \times 100$$

Binding Constant Measurements

For selected compounds where single concentration results at 10 μM had shown % control <5, Kd values were determined.

The equilibrium binding equations yield the following expression for the binding constant for the interaction between the free test compound and the kinase (Kd(test)), assuming that the phage concentration is below Kd(test): $K_{d(test)} = (K_{d(probe)}/(K_{d(probe)} + [\text{Probe}])) \times [\text{test}]_{1/2}$. $K_{d(probe)}$ is the binding constant for the interaction between the kinase and the immobilized ligand, [Probe] is the concentration of the immobilized ligand and $[\text{test}]_{1/2}$ is the concentration of the free test compound at the midpoint of the transition. If [Probe] is below $K_{d(probe)}$ the expression simplifies to $K_{d(test)} = [\text{test}]_{1/2}$. Under these conditions the binding constants measured for the interaction between kinases and test compounds ($K_{d(test)}$) are therefore independent of the affinity of the immobilized ligand for the kinase ($K_{d(probe)}$). T7 phage grow to a titer of $10^8$-$10^{10}$ plaque forming units (PFU)/ml, and the concentration of phage-tagged kinase in the binding reaction is therefore in the low picomolar range. The concentration of the immobilized ligand is kept in the low nanomolar range, below its binding constant for the kinase. Binding data were fit to the equation PFU=L+((H−L)×($K_{d(test)}$/($K_{d(test)}$ [test]))), where L is the lower baseline, H is the upper baseline, $K_{d(test)}$ is the binding constant for the interaction between the test compound and the kinase, and [test] is the free test compound concentration. Binding constants measured in duplicate on the same day as part of the same experiment generally were within twofold. Duplicate measurements performed on separate days generally varied by no more than fourfold. Clustering and visualization was performed with Cluster 3.0 (M. Eisen, Stanford University) and Mapletree software (M. Eisen, Stanford University; L. Simirenko, Lawrence Berkeley National Lab). For kinase/compound combinations where no interaction was observed, the binding constant was arbitrarily set to 1 M.

TABLE 1

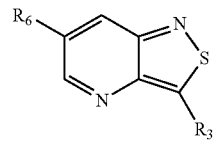

| Example | % Ctrl | Kd (μM) |
|---|---|---|
| 4 | 68 | |
| 7 | 55 | |
| 14 | 87 | |
| 23 | 0.8 | 0.5 |
| 24 | 11 | |
| 25 | 25 | |
| 26 | 0 | 0.052 |
| 27 | 0.1 | 0.042 |
| 31 | 18 | |
| 32 | 2.2 | |
| 33 | 9.4 | |
| 34 | 37 | |
| 28 | 45 | |
| 29 | 0.4 | 0.12 |
| 30 | 0.3 | 0.3 |
| 12 | 62 | |
| 11 | 50 | |
| 3 | 97 | |
| 14 | 100 | |
| 35 | 93 | |
| 36 | 19 | |
| 37 | 22 | |
| 6 | 70 | |
| 5 | 80 | |
| 39 | 88 | |
| 40 | 19 | |
| 38 | 76 | |
| 8 | 61 | |
| 41 | 7.4 | |
| 42 | 72 | |
| 43 | 0.05 | 0.047 |
| 44 | 0.7 | 0.13 |
| 45 | 6.3 | |
| 46 | 2.8 | 0.019 |
| 47 | 0 | 0.018 |
| 48 | 0.2 | 0.072 |
| 49 | 0 | 0.0083 |
| 50 | 0 | 0.0089 |
| 51 | 51 | |
| 52 | 0.15 | 0.2 |
| 53 | 9 | |
| 54 | 0.05 | 0.088 |
| 57 | 2.6 | 0.27 |
| 58 | 0.8 | 0.23 |
| 60 | 1.1 | 0.18 |
| 61 | 0.05 | 0.18 |
| 62 | 0 | 0.082 |
| 63 | 0.6 | 0.14 |
| 64 | 0 | 0.018 |
| 65 | 0 | 0.031 |
| 66 | 0.1 | 0.063 |
| 67 | 0.85 | 0.21 |
| 68 | 0.05 | 0.069 |
| 69 | 0.1 | 0.088 |
| 70 | 4 | 0.32 |
| 71 | 2.6 | 0.33 |
| 72 | 40 | |
| 73 | 0 | 0.1 |
| 74 | 81 | |
| 75 | 0.1 | 0.14 |
| 76 | 0 | 0.027 |
| 78 | 0.1 | 0.19 |
| 79 | 0.05 | 0.21 |
| 80 | 0.1 | 0.11 |
| 81 | 12 | |
| 82 | 0.15 | 0.26 |
| 83 | 0.05 | 0.052 |

TABLE 1-continued

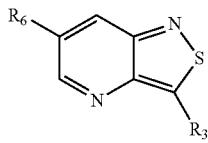

| Example | % Ctrl | Kd (µM) |
|---|---|---|
| 84 | 0 | 0.14 |
| 85 | 31 | |
| 86 | 92 | |
| 87 | 4.3 | 0.33 |

Example 89

Anti-Proliferative Assays

Methodology of the In Vitro Cancer Screen

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions can be made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters can be calculated for each experimental agent. Growth inhibition of 50% (GI50) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

Certain compounds as described in the previous examples were found to inhibit certain human tumor cell lines with at least 50% when measured at a concentration of 10 µM. These human tumor cell lines that are at least 50% growth-inhibited by said compounds include: leukemia cell lines such as K-562 and SR, non-Small Cell Lung cancer cell lines such as HOP-92, Colon cancer cell lines such as KM12 and Melanoma cell lines such as MDA-MB-435.

The invention claimed is:

1. An isothiazolo[4,3-b]pyridine derivative having the general formula I:

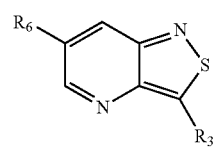

wherein
R$_3$ is selected from the group consisting of halogen, amino, morpholinyl, thiomorpholinyl, pyrrolidinyl, piperazinyl, homopiperazinyl, piperidinyl, (mono- or di-) C$_{1-12}$ alkylamino, (mono- or di-) C$_{2-12}$ alkenylamino, (mono- or di-) C$_{2-12}$ alkynylamino, monoarylamino; diarylamino; (mono- or di-) C$_{3-10}$ cycloalkylamino, C$_{3-10}$ cycloalkylC$_{1-4}$ alkylamino, (mono- or di-) C$_{3-10}$ cycloalkenylamino, (mono- or di-) hydroxy C$_{1-7}$ alkylamino, (mono- or di-) C$_{1-4}$ alkylarylamino, (mono- or di-) arylC$_{1-4}$ alkylamino, mercapto C$_{1-7}$ alkyl, C$_{1-7}$ alkoxy, C$_{1-4}$ alkoxyC$_{1-4}$ alkylamino, alkoxyaryl, C$_{3-10}$ cycloalkoxy, heterocyclic-substituted alkylamino, heterocyclic-substituted arylamino, heterocyclic amino, hydroxy-alkylamino, mercaptoalkylamino, hydroxypiperidinyl, aryl and heteroaryl groups, and, wherein said morpholinyl, thiomorpholinyl, pyrrolidinyl, piperazinyl, piperidinyl, heteroaryl or aryl groups are optionally substituted with one or more substituents selected from the group consisting of halogen, C$_{1-7}$ alkyl, C$_{2-7}$ alkenyl, C$_{2-7}$ alkynyl, halo C$_{1-7}$ alkyl, nitro, hydroxyl, sulfhydryl, amino, C$_{1-7}$ alkoxy, and, wherein one or more carbon atoms in any ring group may be replaced with —C(=O)—;

R$_6$ is selected from the group consisting of halogen, heteroaryl and aryl groups, wherein said heteroaryl or aryl groups are optionally substituted with one or more substituents selected from the group consisting of halogen, C$_{1-7}$ alkyl, C$_{2-7}$ alkenyl, C$_{2-7}$ alkynyl, halo C$_{1-7}$ alkyl, nitro, hydroxyl, sulfhydryl, amino, C$_{1-7}$ alkoxy, C$_{3-10}$ cycloalkoxy, aryloxy, arylalkyloxy, oxyheterocyclic, heterocyclic-substituted alkyloxy, thio C$_{1-7}$ alkyl, thio C$_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino;

and/or a pharmaceutical acceptable addition salt thereof and/or a stereoisomer thereof and/or a solvate thereof.

2. An isothiazolo[4,3-b]pyridine derivative according to claim 1, wherein R$^6$ is selected from the group consisting of 3,4-dimethoxyphenyl; 3-thienyl; phenyl; 2-thienyl; 4-m ethoxy c arb onyl-3 -methoxy-phenyl; 4-acetoxy-3 -methoxyphenyl; 3 -acetoxy-4-methoxyphenyl; 3,5-dimethoxyphenyl; 3,4,5-trimethoxyphenyl, 2,5-dimethoxyphenyl, 3-methoxyphenyl; 4-methoxyphenyl; 3-furanyl; N-methylbenzamide; 2-bromo-4,5-dimethoxyphenyl; 3-methoxy-4-hydroxyphenyl and 4-amino-3-methoxyphenyl.

3. An isothiazolo[4,3-b]pyridine derivative according to claim 1, wherein R$^3$ is selected from the group consisting of morpholinyl, ethanolamino, thiomorpholinyl, piperidinyl, 4-piperidinone, 4-hydroxypiperidinyl, 3-hydroxypiperidinyl, n-pentanolamino, tetrahydropyranyl-4-amino, diethanolamino, 2,3-dihydroxy-propanylamino, pyrrolidinyl, methoxyethylamino, cyclopropylmethylamino, dimethylamino, diethylamino, 2,6-dimethylmorpholinyl, phenyl, pyridinyl, thienyl and ethoxy.

4. An isothiazolo[4,3-b]pyridine derivative selected from the group consisting of:
3-morpholino-6-phenyl-isothiazolo[4,3-b]pyridine;
3-morpholino-6-(4-fluoro-phenyl)-isothiazolo[4,3-b]pyridine;
3-morpholino-6-(3-pyridyl))-isothiazolo[4,3-b]pyridine;
3-morpholino-6-(3,4-dimethoxyphenyl)-isothiazolo[4,3-b]pyridine;
3-morpholino-6-(3-thienyl)-isothiazolo[4,3-b]pyridine;
3-ethanolamino-6-(3-pyridyl)-isothiazolo[4,3-b]pyridine;
3-ethanolamino-6-(3,4-dimethoxyphenyl)-isothiazolo[4,3-b]pyridine;
3-ethanolamino-6-(3-thienyl)-isothiazolo[4,3-b]pyridine;
3-ethanolamino-6-(3-phenyl)-isothiazolo[4,3-b]pyridine;
3-methoxy-6-phenyl-isothiazolo[4,3-b]pyridine;
3-methoxy-6-(4-fluoro-phenyl)-isothiazolo[4,3-b]pyridine;
3-methoxy-6-(3-pyridyl)-isothiazolo[4,3-b]pyridine;
3-methoxy-6-(3,4-dimethoxyphenyl)-isothiazolo[4,3-b]pyridine;
3-methoxy-6-(3-thienyl)-isothiazolo[4,3-b]pyridine;
3-(N-Me-piperazinyl)-6-phenyl-isothiazolo[4,3-b]pyridine;
3-(N-Me-piperazinyl)-6-(3-pyridyl)-isothiazolo[4,3-b]pyridine;
3-(N-Me-piperazinyl)-6-(3,4-dimethoxyphenyl)-isothiazolo[4,3-b]pyridine;
3-(N-Me-piperazinyl)-6-(3-thienyl)-isothiazolo[4,3-b]pyridine;
3-(N-Me-piperazinyl)-6-(4-fluorophenyl)-isothiazolo[4,3-b]pyridine;
3-amino-6-phenyl-isothiazolo[4,3-b]pyridine;
3-amino-6-(3-pyridyl)-isothiazolo[4,3-b]pyridine;
3-amino-6-(3,4-dimethoxyphenyl)-isothiazolo[4,3-b]pyridine;
3-amino-6-(4-fluorophenyl)-isothiazolo[4,3-b]pyridine;
3-amino-6-(3-thienyl)-isothiazolo[4,3-b]pyridine;
4-(6-(Thiophen-2-yl)isothiazolo[4,3-b]pyridin-3-yl)morpholine;
4-(6-(2,5-Dimethoxyphenyl)isothiazolo[4,3-b]pyridin-3-yl)morpholine;
4-(6-(2,4-Dimethoxyphenyl)isothiazolo[4,3-b]pyridin-3-yl)morpholine;
Methyl 2-methoxy-4-(3-morpholinoisothiazolo[4,3-b]pyridin-6-yl)benzoate;
2-Methoxy-4-(3-morpholinoisothiazolo[4,3-b]pyridin-6-yl)phenyl acetate;
4-(6-(3,5-Dimethoxyphenyl)isothiazolo[4,3-b]pyridin-3-yl)morpholine;
4-(6-(3,4,5-Trimethoxyphenyl)isothiazolo[4,3-b]pyridin-3-yl)morpholine;
2-Methoxy-4-(3-morpholinoisothiazolo[4,3-b]pyridin-6-yl)aniline;
4-(6-(Benzo[d][1,3]dioxol-5-yl)isothiazolo[4,3-b]pyridin-3-yl)morpholine;
4-(6-(Furan-3-yl)isothiazolo[4,3-b]pyridin-3-yl)morpholine;
Methyl 4-(3-morpholinoisothiazolo[4,3-b]pyridin-6-yl)benzoate;
N-Methyl-4-(3-morpholinoisothiazolo[4,3-b]pyridin-6-yl)benzamide;
6-bromo-3-(piperidin-1-yl)isothiazolo[4,3-b]pyridine;
6-bromo-3-thiomorpholinoisothiazolo[4,3-b]pyridine;
3-morpholino-6-aryl-isothiazolo[4,3-b]pyridines;
6-(3,4-dimethoxyphenyl)-3-(piperidin-1-yl)isothiazolo[4,3-b]pyridine;
6-(3,4-dimethoxyphenyl)-3-thiomorpholinoisothiazolo[4,3-b]pyridine;
3-bromo-6-(2-bromo-4,5-dimethoxyphenyl)isothiazolo[4,3-b]pyridine;
4-(6-(2-bromo-4,5-dimethoxyphenyl)isothiazolo[4,3-b]pyridin-3-yl)morpholin;
4-(6-(3-methoxyphenyl)isothiazolo[4,3-b]pyridin-3-yl)morpholine;
2-methoxy-5-(3-morpholinoisothiazolo[4,3-b]pyridin-6-yl)phenyl acetate;
4-(6-(4-methoxyphenyl)isothiazolo[4,3-b]pyridin-3-yl)morpholine;
1-(6-(3,4-dimethoxyphenyl)isothiazolo[4,3-b]pyridin-3-yl)piperidin-4-one;
1-(6-(3,4-dimethoxyphenyl)isothiazolo[4,3-b]pyridin-3-yl)piperidin-4-ol;
5-(6-(3,4-dimethoxyphenyl)isothiazolo[4,3-b]pyridin-3-ylamino)pentan-1-ol;
1-(6-(3,4-dimethoxyphenyl)isothiazolo[4,3-b]pyridin-3-yl)piperidin-3-ol;
6-(3,4-dimethoxyphenyl)-N-(tetrahydro-2H-pyran-4-yl)isothiazolo[4,3-b]pyridin-3-amine;

2,2'-(6-(3,4-dimethoxyphenyl)isothiazolo[4,3-b]pyridin-3-ylazanediyl)diethanol;
3-(6-(3,4-dimethoxyphenyl)isothiazolo[4,3-b]pyridin-3-ylamino)propane-1,2-diol;
ethyl-4-(6-(3,4-dimethoxyphenyl)isothiazolo[4,3-b]pyridin-3-ylamino)piperidine-1-carboxylate;
6-(3,4-dimethoxyphenyl)-3-(pyrrolidin-1-yl)isothiazolo[4,3-b]pyridine;
6-(3,4-dimethoxyphenyl)-N-phenethylisothiazolo[4,3-b]pyridin-3-amine;
6-(3,4-dimethoxyphenyl)-N-(2-methoxyethyl)isothiazolo[4,3-b]pyridin-3-amine;
N-(cyclopropylmethyl)-6-(3,4-dimethoxyphenyl)isothiazolo[4,3-b]pyridin-3-amine;
6-(3,4-dimethoxyphenyl)-N,N-dimethylisothiazolo[4,3-b]pyridin-3-amine;
6-(3,4-dimethoxyphenyl)-N,N-diethylisothiazolo[4,3-b]pyridin-3-amine;
(2R,6S)-4-(6-(3,4-dimethoxyphenyl)isothiazolo[4,3-b]pyridin-3-yl)-2,6-dimethylmorpholine;
8-(6-(3,4-dimethoxyphenyl)isothiazolo[4,3-b]pyridin-3-yl)-1,4-dioxa-8-azaspiro[4.5]decane;
6-(3,4-dimethoxyphenyl)-3-phenylisothiazolo[4,3-b]pyridine;
6-(3,4-dimethoxyphenyl)-3-(pyridin-4-yl)isothiazolo[4,3-b]pyridine;
6-(3,4-dimethoxyphenyl)-3-(thiophen-3-yl)isothiazolo[4,3-b]pyridine;
6-(3,4-dimethoxyphenyl)isothiazolo[4,3-b]pyridine;
6-(2-bromo-4,5-dimethoxyphenyl)-3-(4-methylpiperidin-1-yl)isothiazolo[4,3-b]pyridine; and
6-(2-bromo-4,5-dimethoxyphenyl)-3-ethoxyisothiazolo[4,3-b]pyridine.

5. A pharmaceutical composition comprising an isothiazolo[4,3-b]pyridine derivative according to claim 1.

6. A pharmaceutical composition for the treatment of osteosarcoma or prostate cancer in an animal comprising an isothiazolo[4,3-b]pyridine derivative according to claim 1.

7. A pharmaceutical composition for the treatment of Parkinson's disease in an animal comprising an isothiazolo[4,3-b]pyridine derivative according to claim 1.

8. The pharmaceutical composition according to claim 6, wherein said animal is a human being.

9. A pharmaceutical composition comprising a therapeutically effective amount of an isothiazolo[4,3-b]pyridine derivative according to claim 1 and one or more pharmaceutically acceptable excipients.

10. A method of treatment of osteosarcoma or prostate cancer in an animal, comprising the administration of a therapeutically effective amount of an isothiazolo[4,3-b]pyridine derivative according to claim 1, optionally in combination with one or more pharmaceutically acceptable excipients.

11. The pharmaceutical composition according to claim 7, wherein said animal is a human being.

12. The method according to claim 10, wherein said animal is a human being.

* * * * *